US011980545B2

(12) United States Patent
Rafiee et al.

(10) Patent No.: US 11,980,545 B2
(45) Date of Patent: May 14, 2024

(54) ANNULOPLASTY PROCEDURES, RELATED DEVICES AND METHODS

(71) Applicant: Transmural Systems LLC, Andover, MA (US)

(72) Inventors: Nasser Rafiee, Andover, MA (US); Stuart MacDonald, Andover, MA (US); Koosha Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 290 days.

(21) Appl. No.: 16/264,549

(22) Filed: Jan. 31, 2019

(65) Prior Publication Data

US 2019/0240022 A1    Aug. 8, 2019

Related U.S. Application Data

(63) Continuation of application No. PCT/US2018/048172, filed on Aug. 27, 2018, and a
(Continued)

(51) Int. Cl.
*A61B 17/32* (2006.01)
*A61B 17/04* (2006.01)
(Continued)

(52) U.S. Cl.
CPC ........ *A61F 2/2466* (2013.01); *A61B 17/0467* (2013.01); *A61B 17/0469* (2013.01);
(Continued)

(58) Field of Classification Search
CPC ............ A61B 17/0467; A61B 17/0469; A61B 17/06161; A61B 17/320016; A61B 2017/00292; A61B 17/32; A61F 2/2466
See application file for complete search history.

(56) References Cited

U.S. PATENT DOCUMENTS

| | | |
|---|---|---|
| 3,572,325 A | 3/1971 | Bazell et al. |
| 4,917,698 A | 4/1990 | Carpentier et al. |
| (Continued) | | |

FOREIGN PATENT DOCUMENTS

| | | |
|---|---|---|
| EP | 1 022 022 | 11/1999 |
| EP | 2742912 A2 | 6/2014 |
| (Continued) | | |

OTHER PUBLICATIONS

Alfieri, et al., "Future of transcatheter repair of the mitral valve", Abstract ONLY,*American Journal of Cardiology*, vol. 96, No. 12A, pp. 71L-75L, 2005.
(Continued)

*Primary Examiner* — Christopher D. Prone
(74) *Attorney, Agent, or Firm* — DeWitt LLP; Brian R. Pollack, Esq.

(57) ABSTRACT

Devices and methods are disclosed for the treatment or repair of regurgitant cardiac valves, such as a mitral valve. An illustrative annuloplasty device can be placed in the coronary sinus to reshape the mitral valve and reduce mitral valve regurgitation. The disclosure also provides improved techniques for cardiac pacing.

17 Claims, 33 Drawing Sheets

Related U.S. Application Data continuation-in-part of application No. 15/796,344, filed on Oct. 27, 2017, now Pat. No. 10,433,962, said application No. PCT/US2018/048172 is a continuation-in-part of application No. 15/796,344, filed on Oct. 27, 2017, now Pat. No. 10,433,962, which is a continuation-in-part of application No. PCT/US2017/031543, filed on May 8, 2017.

(60) Provisional application No. 62/663,903, filed on Apr. 27, 2018, provisional application No. 62/615,309, filed on Jan. 9, 2018, provisional application No. 62/550,583, filed on Aug. 26, 2017, provisional application No. 62/332,754, filed on May 6, 2016.

(51) Int. Cl.
*A61F 2/24* (2006.01)
*A61B 17/00* (2006.01)
*A61N 1/05* (2006.01)

(52) U.S. Cl.
CPC .. *A61F 2/2451* (2013.01); *A61B 2017/00292* (2013.01); *A61N 2001/0578* (2013.01)

(56) References Cited

U.S. PATENT DOCUMENTS

| | | | |
|---|---|---|---|
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,074,841 A * | 12/1991 | Ademovic | A61B 17/320783 604/22 |
| 5,084,058 A * | 1/1992 | Li | A61B 17/0469 606/139 |
| 5,104,407 A | 4/1992 | Lam et al. | |
| 5,201,880 A | 4/1993 | Wright et al. | |
| 5,290,300 A | 3/1994 | Cosgrove et al. | |
| 5,311,866 A | 5/1994 | Kagan et al. | |
| 5,345,936 A | 9/1994 | Pomeranz et al. | |
| 5,350,420 A | 9/1994 | Cosgrove et al. | |
| 5,387,219 A | 2/1995 | Rappe | |
| 5,476,528 A | 12/1995 | Trimm et al. | |
| 5,972,030 A | 10/1999 | Garrison et al. | |
| 5,989,264 A * | 11/1999 | Wright | A61B 17/22012 606/113 |
| 6,259,938 B1 | 7/2001 | Zarychta et al. | |
| 6,402,781 B1 | 6/2002 | Langberg et al. | |
| 6,485,760 B2 | 11/2002 | Matsuyama | |
| 6,716,459 B2 | 4/2004 | Matsuyama | |
| 6,726,716 B2 | 4/2004 | Marquez | |
| 7,073,511 B2 | 7/2006 | Schroeppel | |
| 7,090,695 B2 | 8/2006 | Solem et al. | |
| 7,235,083 B1 | 6/2007 | Perez et al. | |
| 8,211,171 B2 | 7/2012 | Kim et al. | |
| 8,231,671 B2 | 7/2012 | Kim | |
| 8,632,588 B2 | 1/2014 | Kim | |
| 9,271,833 B2 | 3/2016 | Kim et al. | |
| 9,743,922 B2 | 8/2017 | Kim et al. | |
| 9,943,409 B2 | 4/2018 | Kim et al. | |
| 2002/0128701 A1 | 9/2002 | Winters | |
| 2002/0147391 A1 | 10/2002 | Morency | |
| 2002/0198591 A1 | 12/2002 | Stergiopulos | |
| 2003/0078465 A1 | 4/2003 | Pai et al. | |
| 2003/0083538 A1 | 5/2003 | Adams et al. | |
| 2003/0130731 A1 | 7/2003 | Vidlund et al. | |
| 2004/0098116 A1 | 5/2004 | Callas et al. | |
| 2004/0102840 A1 | 5/2004 | Solem et al. | |
| 2004/0133273 A1 | 7/2004 | Cox | |
| 2004/0220657 A1 | 11/2004 | Nieminen et al. | |
| 2004/0254600 A1 | 12/2004 | Zarbatany et al. | |
| 2005/0027351 A1 | 2/2005 | Reuter et al. | |
| 2005/0027353 A1 | 2/2005 | Alferess et al. | |
| 2005/0038447 A1 | 2/2005 | Huffmaster | |
| 2005/0038506 A1 | 2/2005 | Webler et al. | |
| 2005/0137451 A1 | 6/2005 | Lucas et al. | |
| 2005/0216039 A1 | 9/2005 | Lederman | |
| 2005/0222488 A1 | 10/2005 | Chang et al. | |
| 2005/0256521 A1 | 11/2005 | Kozel | |
| 2006/0106279 A1 | 5/2006 | Machold et al. | |
| 2006/0184242 A1 | 8/2006 | Lichtenstein | |
| 2007/0027392 A1 | 2/2007 | Schwartz | |
| 2007/0073391 A1 | 3/2007 | Bourang et al. | |
| 2007/0123978 A1 | 5/2007 | Cox | |
| 2007/0135826 A1 | 6/2007 | Zaver et al. | |
| 2007/0185500 A1 | 8/2007 | Martin et al. | |
| 2007/0208376 A1 | 9/2007 | Meng | |
| 2007/0249901 A1 | 10/2007 | Ohline et al. | |
| 2007/0276437 A1 | 11/2007 | Call et al. | |
| 2008/0004534 A1 | 1/2008 | Gelbart et al. | |
| 2008/0004697 A1 | 1/2008 | Lichtenstein et al. | |
| 2008/0058800 A1 | 3/2008 | Collins et al. | |
| 2008/0065113 A1 * | 3/2008 | Smith | A61B 17/0483 606/138 |
| 2008/0228171 A1 | 9/2008 | Kugler et al. | |
| 2008/0228267 A1 | 9/2008 | Spence et al. | |
| 2008/0249397 A1 | 10/2008 | Kapadia | |
| 2008/0306499 A1 | 12/2008 | Katoh et al. | |
| 2009/0112244 A1 | 4/2009 | Freudenthal | |
| 2009/0171274 A1 | 7/2009 | Harlev et al. | |
| 2010/0114299 A1 | 5/2010 | Ben Muvhar et al. | |
| 2011/0054597 A1 | 3/2011 | Kim | |
| 2011/0112632 A1 | 5/2011 | Chau et al. | |
| 2011/0313434 A1 | 12/2011 | Kocaturk | |
| 2012/0029629 A1 | 2/2012 | Kim | |
| 2013/0211510 A1 | 8/2013 | Lederman et al. | |
| 2015/0157459 A1 | 6/2015 | Macoviak et al. | |
| 2015/0342600 A1 | 12/2015 | Kim et al. | |
| 2016/0081798 A1 | 3/2016 | Kocaturk | |
| 2016/0193043 A1 | 7/2016 | Kim | |
| 2017/0119489 A1 | 5/2017 | Kim | |
| 2017/0150964 A1 | 6/2017 | Kim | |
| 2017/0209686 A1 | 7/2017 | Kim | |

FOREIGN PATENT DOCUMENTS

| | | |
|---|---|---|
| RU | 134785 | 11/2013 |
| WO | 1994006357 A1 | 3/1994 |
| WO | WO 95/006447 | 3/1995 |
| WO | 1999048429 A1 | 9/1999 |
| WO | WO 01/054618 | 8/2001 |
| WO | WO 02/100240 | 12/2002 |
| WO | WO 03/037171 | 5/2003 |
| WO | WO 04/045378 | 6/2004 |
| WO | WO 2005/046520 | 5/2005 |
| WO | 2006105008 A1 | 10/2006 |
| WO | WO 06/116129 | 11/2006 |
| WO | WO 06/132880 | 12/2006 |
| WO | 2008060553 | 5/2008 |
| WO | 2008070262 A2 | 6/2008 |
| WO | 2008089044 | 7/2008 |
| WO | 20120243898 | 4/2012 |
| WO | 2014191924 | 12/2014 |
| WO | 2015005690 A1 | 1/2015 |
| WO | 2015028986 A1 | 3/2015 |
| WO | 2015167194 A1 | 11/2015 |
| WO | 2015178612 A1 | 11/2015 |
| WO | 2015194754 A1 | 12/2015 |
| WO | 2016013763 A1 | 1/2016 |
| WO | 2016013765 A1 | 1/2016 |
| WO | 2016024710 A1 | 2/2016 |
| WO | 2016032177 | 3/2016 |
| WO | 2016032177 A1 | 3/2016 |

OTHER PUBLICATIONS

Block, "Percutaneous transcatheter repair for mitral regurgitation", Abstract Only, *Journal of Interv. Cardiology*, vol. 6, pp. 547-551, 2006.

Chinzei, et al., "MR Compatibility of Mechatronic Devices: Design Criteria", *Int. Conj Med. Image Comput. Assist Interv.*, vol. 2, pp. 1020-1031, 1999.

(56) References Cited

OTHER PUBLICATIONS

De Silva, et al., "X-Ray Fused With Magnetic Resonance Imaging (XFM) to Target Endomyocardial Injections", *Circulation*, vol. 114, pp. 2342-2350, 2006.
Maniu, et al., "Acute and chronic reduction of functional mitral regurgitation in experimental heart failure by percutaneous mitral annuloplasty", *Journal of American Coll. Cardiol.*, vol. 44, No. 8, pp. 1652-1661, 2004.
Maselli, et al., "Percutaneous Mitral Annuloplasty: An Anatomic Study of Human Coronary Sinus and Its Relation With Mitral Valve Annulus and Coronary Arteries", *Circulation*, vol. 114, pp. 377-380, 2006.
Webb, et al., "Percutaneous Transvenous Mitral Annuloplasty: Initial Human Experience With Device Implantation in the Coronary Sinus", *Circulation*, vol. 113, pp. 851-855, 2006.
International Search Report and Written Opinion for International Application No. PCT/US2017/017367, 8 pages, dated May 25, 2017.
Extended European Search Report for corresponding European Patent Application No. 17793543.4, dated Nov. 26, 2019.
International Search Report and Written Opinion dated Nov. 24, 2011, for International Patent Application PCT/US2011/051748.
International Preliminary Report on Patentability dated Mar. 19, 2013, for International Patent Application PCT/US2011/051748.
Federal Institute of Industrial Property/RU Search Authority. International Search Report and Written Opinion dated Aug. 24, 2017, regarding related International Patent Application No. PCT/US2017/031543, 9 pages.
June-Hong Kim et al. "Mitral Cerclage Annuloplasty, A Novel Transcatheter Treatment for Secondary Mitral Valve Regurgitation." Journal of the American College of Cardiology, vol. 54, No. 7, pp. 638-651 (2009).

\* cited by examiner

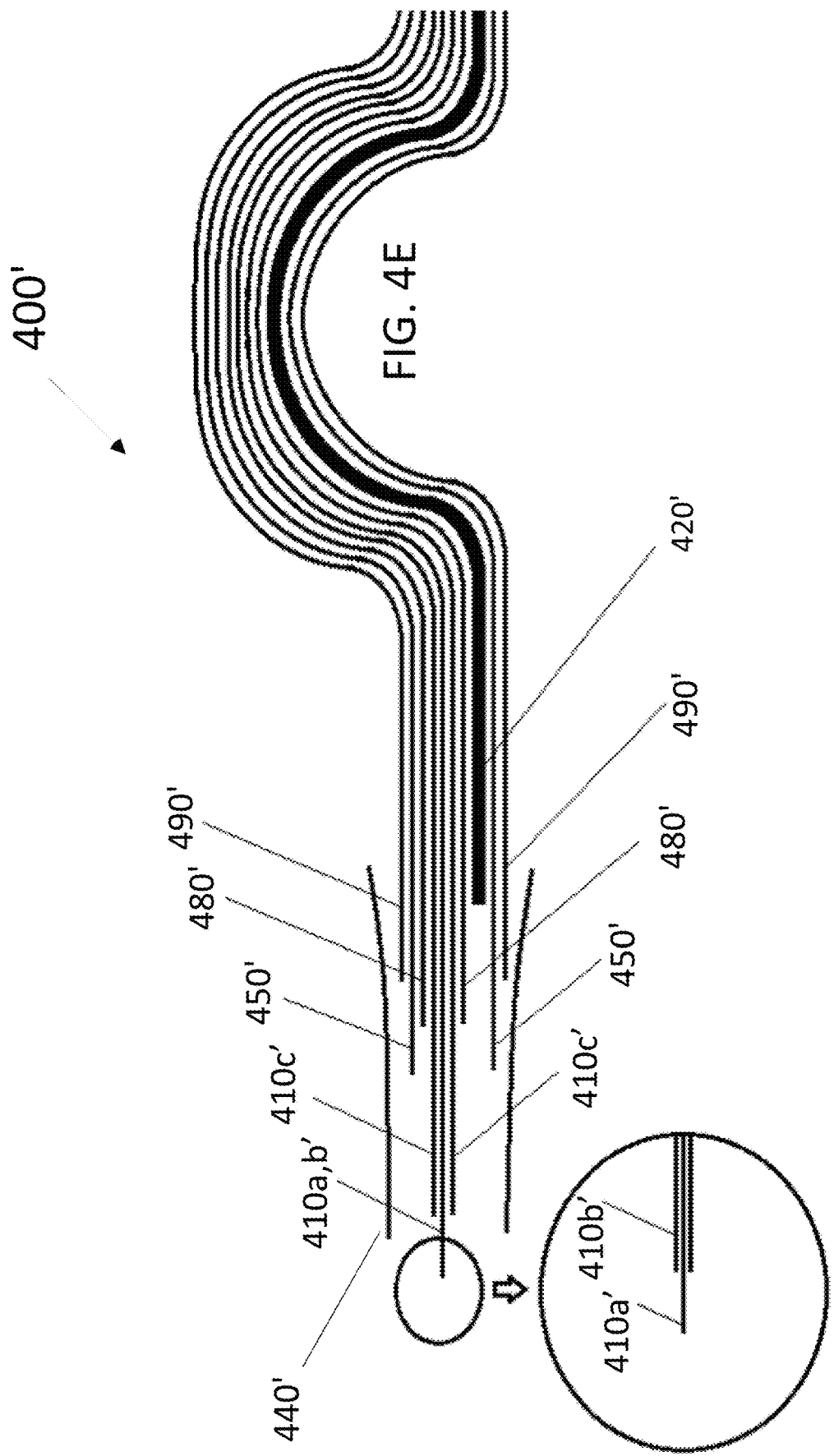

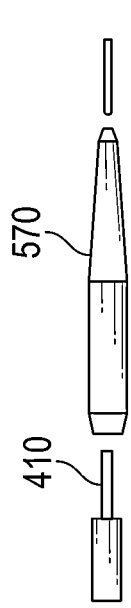
FIG. 5D
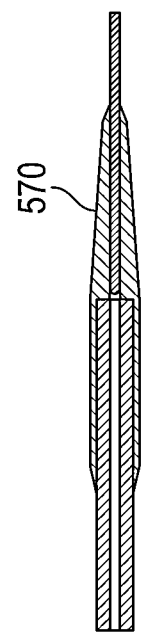
FIG. 5E
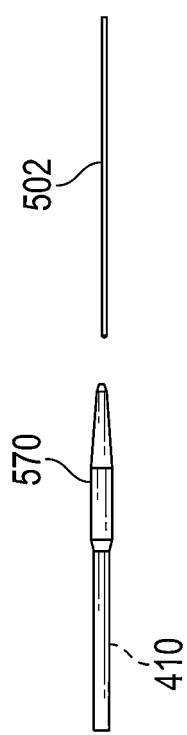
FIG. 5A
FIG. 5B
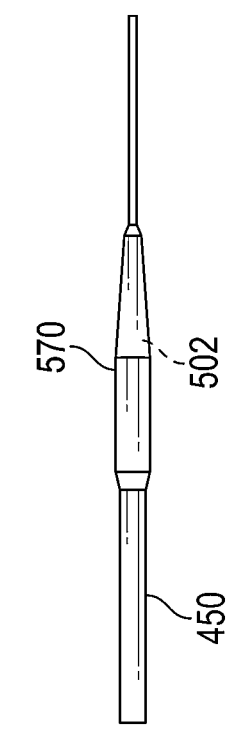
FIG. 5C
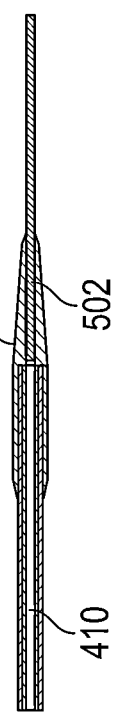

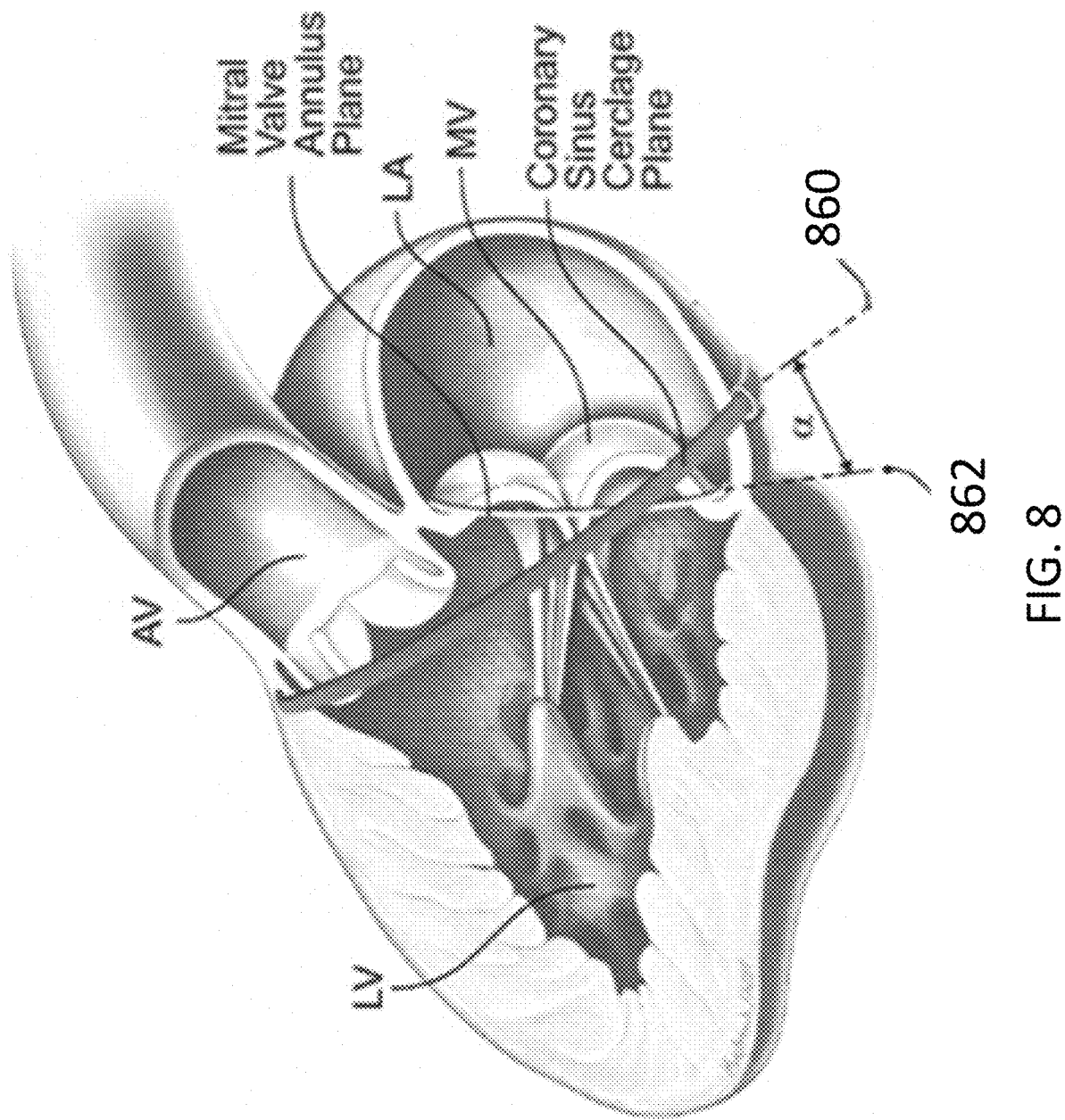

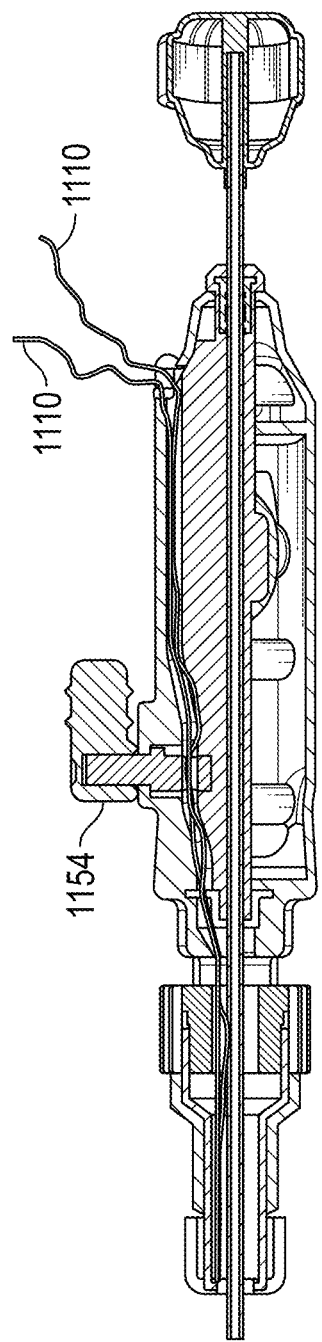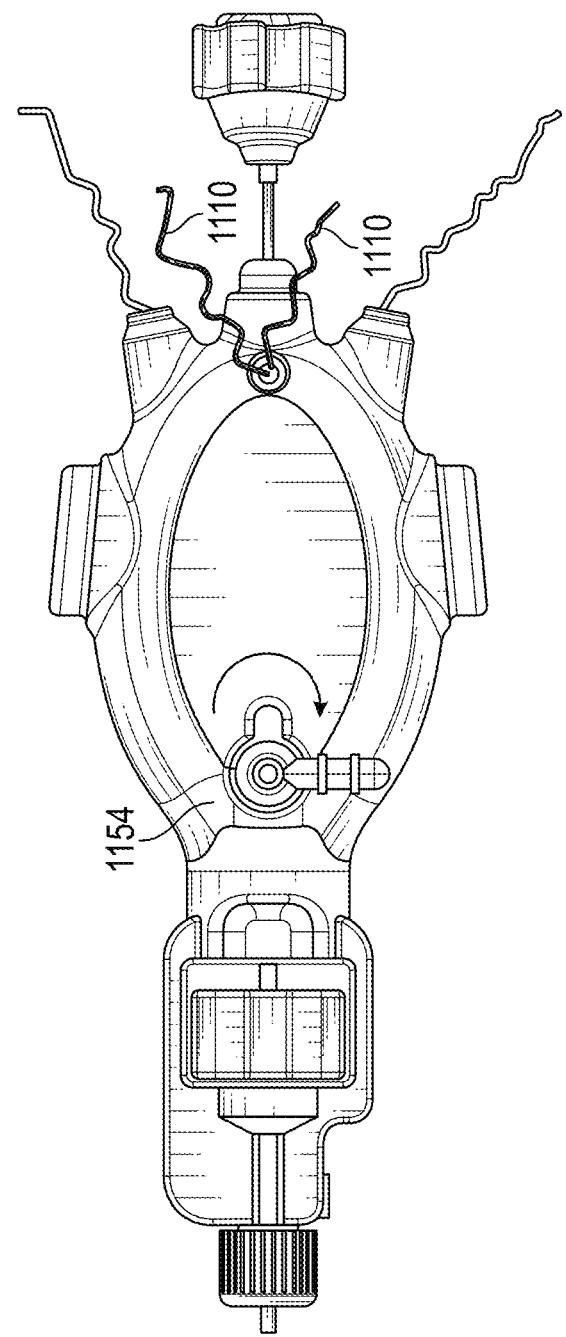
FIG. 11A
FIG. 11B

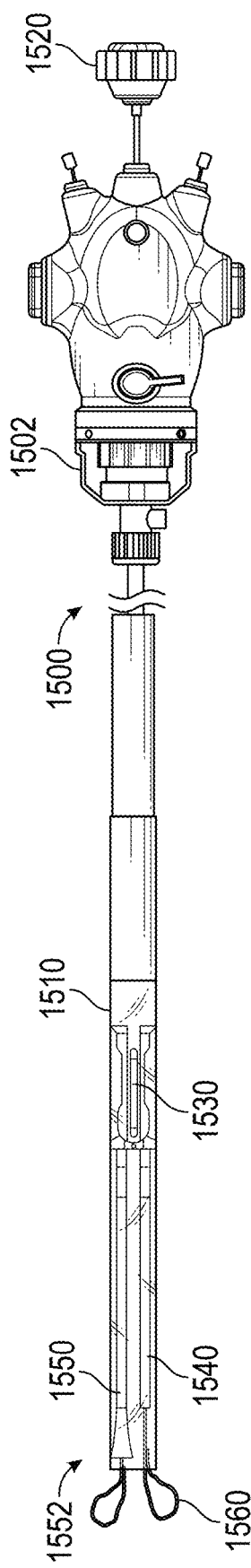
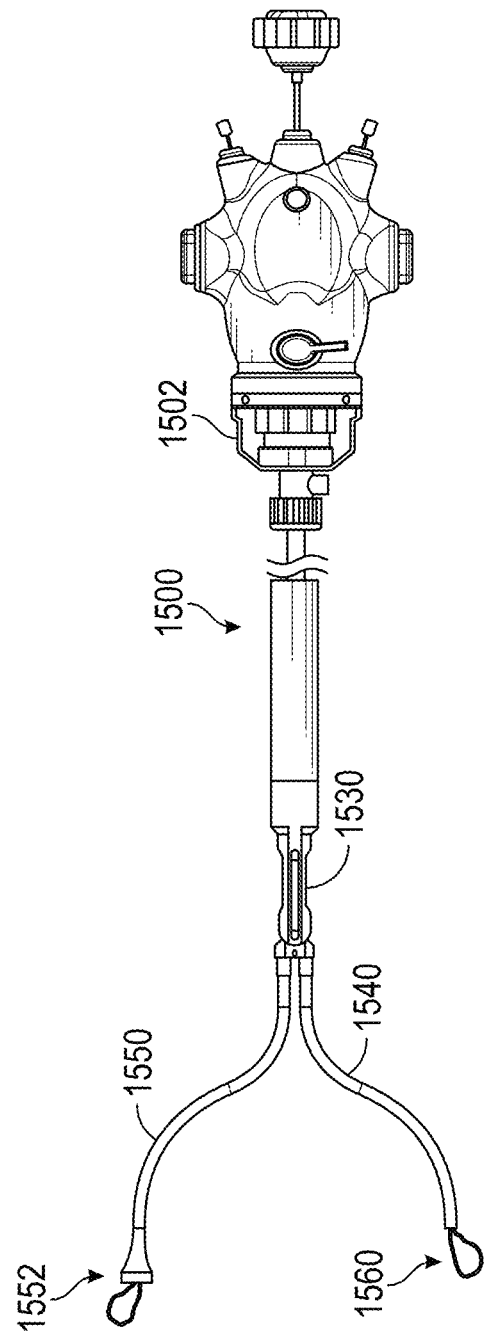
FIG. 15A
FIG. 15B

ANNULOPLASTY PROCEDURES, RELATED DEVICES AND METHODS

CROSS-REFERENCE TO RELATED APPLICATIONS

The present patent application is a continuation of and claims the benefit of priority to International Application No. PCT/US18/48172, filed Aug. 27, 2018, which in turn claims the benefit of priority to U.S. patent application Ser. No. 15/796,344, filed Oct. 27, 2017, U.S. Provisional Patent Application Ser. No. 62/663,903, filed Apr. 27, 2018, U.S. Provisional Patent Application Ser. No. 62/550,583, filed Aug. 26, 2017, and U.S. Provisional Patent Application Ser. No. 62/615,309, filed Jan. 9, 2018. The present patent application is a continuation-in-part of and claims the benefit of priority to U.S. patent application Ser. No. 15/796,344, filed Oct. 27, 2017, which in turn is a continuation-in-part of and claims the benefit of priority to PCT/US2017/031543, filed May 8, 2017, which in turn claims the benefit of priority to U.S. Provisional Patent Application Ser. No. 62/332,754, filed May 6, 2016. The disclosure of each of the foregoing patent applications is expressly incorporated by reference herein for any purpose whatsoever.

FIELD OF THE DISCLOSURE

The present disclosure relates to annuloplasty techniques and devices in which tensioning elements (e.g., tethers) are placed in the coronary sinus to perform mitral valve annuloplasty and treat mitral valve regurgitation.

BACKGROUND

Traditional mitral valve annuloplasty requires open heart surgery with a sternotomy or thoracotomy and cardiac arrest and cardio-pulmonary bypass. For example, the annuloplasty procedure is performed through a surgical incision in which the effective size of the valve annulus is reduced by attaching a prosthetic annuloplasty ring to the left atrial aspect of the mitral valve annulus. A variety of rigid and flexible annuloplasty rings have been developed for this purpose, such as those shown in U.S. Pat. Nos. 4,917,698; 5,041,130; 5,061,277; 5,064,431; 5,104,407; 5,201,880; and 5,350,420. Although very effective, this open-heart procedure is accompanied by substantial morbidity and prolonged convalescence. As a result, the procedure often is not offered to patients who are insufficiently symptomatic to justify the surgical risk and morbidity, or to patients who suffer advanced disease, or to patients with substantial co-morbidity.

Percutaneous approaches to mitral valve repair have been developed to reduce the clinical disadvantages of the open-heart procedures. But, these procedures suffer from various drawbacks. International Application No. PCT/US2017/031543, filed May 8, 2017, related to the present disclosure, presents considerable improvements over the state of that prior art. In some aspects, the present disclosure provides still further improvements over the prior art.

In other aspects, the present disclosure provides improvements in the area of pacing. Since a pacemaker was first introduced by Furman and Rovinson in 1958, the pacemaker has been used as an important device for treating patients with bradyarrythmia. Pacemakers are usually used in treatments for arrhythmia such as complete atrioventricular block, high degree atrioventricular block, and sinus node dysfunction accompanied by symptoms. A treatment using a pacemaker is a method that artificially provides an electrical stimulus when an electrical stimulus is not normally transmitted to a heart, and/or when an incorrect stimulus is transmitted to the heart.

FIGS. 1A-1C are views of a conduction system of a human heart, in which FIG. 1A shows a flow in a conduction system, FIG. 1B shows a waveform in an electrocardiogram, and FIG. 1C illustrates the relationship between a conduction process and a waveform. As discussed in U.S. patent application Ser. No. 15/328,046, filed Jun. 16, 2015 (incorporated by reference herein in its entirety for any purpose whatsoever), an electrical stimulus is transmitted to the overall ventricles through a conduction pathway after passing through a sinoatrial (SA) node, an atrioventricular (AV) node in the atriums and then passing through the bundle of His and a bundle branch in the ventricles.

In an electrocardiogram, a QRS-complex is generated by a depolarization process of ventricular muscles. The first downward wave following a P-wave is called a Q-wave, the first upward wave is called an R-wave, and the downward wave following the R-wave is called an S-wave. The width of the QRS indicates the time taken for electricity to be conducted throughout the ventricles. The width of the QRS is typically within about 0.12 seconds (around about 90 ms) in a normal state, but when it is 0.12 seconds or more, it indicates the presence of an interventricular conduction defect.

A pacemaker is generally composed of a generator and a lead. The generator supplies power and includes a controller with processing circuitry as well as detection circuitry for detecting operational aspects of the heart. The pacemaker typically supplies power or suspends power, depending on the state of operation of the heart. Power is selectively applied to the heart by way of the lead, which terminates in an electrode. Pacemakers typically operate in a bipolar manner, meaning that the lead actually includes two electrodes—one for delivering electrons (anode) and one for absorbing electrons (cathode). However, the cathode is typically considered to be the hot lead for purposes of convention. In the event the anode breaks or ceases to function, the pacemaker controller will detect this and then operate the device as a monopolar device, wherein the anode becomes the casing and the "hot" lead continues to act as a cathode.

According to a common treatment that is performed by a pacemaker at present, the tip of the lead of a pacemaker is inserted and fixed in the apex of the right ventricle (RV apex) of ventricles and then electrical stimulus is provided. This is called right ventricular apical pacing (RVAP). In RVAP, the electrical stimulus at the RV apex is not transmitted through the conduction system of the heart that quickly transmits electrical stimulus in a ventricle. It is instead transmitted through cardiomyocytes of the ventricle that relatively slowly transmit electrical stimulus. Consequently, it can take a relatively long time for the electrical stimulus to spread through the entire ventricle. This can be expected to (and typically does) result in an increase of QRS width, which results in ventricular desynchronization, and reduces the pumping efficiency of the heart. Ideally, the ventricles are contracted at the same time for better efficiency.

To address this, attempts have been made to position the electrode of the pacemaker lead at a right ventricular basal septum and applying electrical stimulus around the nerve bundles that precipitate ventricular contraction. This is referred to as right ventricular septal pacing (RVSP). The RVSP is most usually used at the interventricular septum of a right ventricular outflow tract (RVOT). RVSP theoretically compensates for the defects of the RVAP, but in the actual operation it is difficult to accurately position the lead of a pacemaker at the interventricular septum around the RVOT and the lead may be separated or moved, so the operation itself is difficult and accordingly it is not generally used. The RVSP has another characteristic that positions the lead tip at an interventricular septum, but stimulates not the inside, but the outer side of the interventricular septum, and it is known that the RVSP is less effective than the method of stimulating the endocardium or the center of an interventricular septum.

Another method of obtaining a narrower QRS is applied to a case when a patient with heart failure accompanied by ventricular insufficiency has a wide QRS in an electrocardiogram. This method uses two leads, and positions a lead at an RV apex and applies electrical stimulus and positions the other lead at a left lateral vein and applies electrical stimulus to a side of the left ventricle. This treatment seeks to obtain a narrower QRS by simultaneously applying electrical stimulus to the RV apex and the side of the left ventricle. This is referred to as "Cardiac Resynchronization Therapy (CRT)". CRT is a very effective treatment when a patient with heart failure has LBBB (left bundle branch block). However, CRT has a deficiency in that it needs to use two leads for stimulating ventricles in order to obtain a narrower QRS.

Intraseptal pacing that can apply direct electrical stimulus to an interventricular septum has been attempted. For example, methods by forcibly positioning the lead of a pacemaker into the interventricular septum directly through the left ventricle from the right ventricle have been disclosed in US2010/0298841 and US 2013/0231728. These methods have high invasion depth that causes an artificial loss of interventricular septum between the left and right ventricles, have a high possibility of tearing surrounding tissues during the operation, and have a high possibility of causing an embolism due to air or blood clots. Further, these methods have many dangers and limits, for example, it can locally approach the middle portion or the apex of ventricles rather than the base which is preferable. U.S. Ser. No. 15/328,046 attempts to improve on the state of the art by a further approach intended to address the deficiencies in the aforementioned approaches. The present disclosure provides additional improvements over the state of the art.

SUMMARY OF THE DISCLOSURE

In a majority of humans, the coronary vein crosses over the left circumflex ("LCx") artery, which has limited the usefulness of coronary sinus annuloplasty. Some techniques for addressing this are described, for example, in U.S. Pat. No. 9,271,833, and U.S. patent application Ser. No. 15/056,599, filed Feb. 29, 2016, each of which is incorporated by reference herein in its entirety for any purpose whatsoever. Further improvements are detailed in U.S. patent application Ser. No. 15/796,344. The present disclosure provides still further improvements in such techniques and related devices to enhance the reliability and efficacy of cerclage procedures.

In particular embodiments, the disclosure provides implementations of an implant that includes a bridge having a proximal end, a distal end, and an arched portion defined between the proximal end and the distal end of the bridge. The bridge defines an upwardly facing surface from the proximal end to the distal end of the bridge. The implant further includes an elongate inner tether disposed on the upwardly facing surface from the proximal end to the distal end of the bridge. The elongate inner tether is coupled to the bridge to maintain the relative position of the elongate inner tether to the bridge. The implant further includes an outer sheath material surrounding and encasing the bridge and elongate inner tether.

If desired, at least one of the elongate inner tether and the outer sheath material can include radiopaque material along its length. The radiopaque material within the elongate inner tether can include a radiopaque wire disposed within a length of heat shrunk polymeric tube that resides within a hollow core of the elongate inner tether. The elongate inner tether can be coupled to the bridge by a polymeric tube that is shrunk around and in direct physical contact with the bridge and the inner elongate tether, the polymeric tube extending axially beyond the proximal end and the distal end of the bridge. The outer sheath material can include a hollow suture material that extends proximally and distally beyond the polymeric tube. Portions of the polymeric tube can extend beyond the proximal end and the distal end of the bridge act as a strain relief to provide a transition in stiffness of the implant from the bridge to the outer sheath material. The outer sheath material can include a hollow suture material that extends proximally and distally beyond the bridge. If desired, the implant can further include a strain relief tube shrunk around the proximal and distal ends of the bridge, wherein the strain relief tubes hold the inner tether in place with respect to the bridge.

In various implementations, the bridge can be formed from shape memory material and can be configured to facilitate vertical compression of the arch portion of the bridge to lower the profile of the bridge from a first height to a second, lower height to facilitate introduction of the bridge into a percutaneous delivery system, wherein the arch portion of the bridge is configured to self-expand to the first height after it is deployed from the delivery system. For example, the shape memory material can be in the shape of a flat wire.

If desired, the implant can further include a selectively removable proximal delivery tube disposed over the outer sheath material, a distal end of the proximal delivery tube abutting near a proximal end region of the bridge, and/or a selectively removable distal delivery tube disposed over the outer sheath material, a proximal end of the distal delivery tube abutting near a distal end region of the bridge. The implant can further include an implant lock, wherein opposite ends of the outer sheath material are directed through the implant lock, and further wherein the implant lock is configured to maintain the length of the outer sheath material when installed in a heart. The implant lock can define at least one distal opening therein. The at least one distal opening can be connected to two distally extending tubular limbs for guiding the outer sheath material therethrough. A first of the tubular limbs can be configured to traverse the tricuspid valve and can include an atraumatic distal tip formed thereon for distributing axially applied stress across a surface of a native septum after traversing the tricuspid valve. The first tubular limb can be configured to permit the outer sheath material to pass therethrough. A second of the tubular limbs can be configured to traverse the coronary sinus and is configured to permit the outer sheath material to pass therethrough. The first and second tubular limbs can each be polymeric tubes preformed with a curvature of about 90 degrees along their lengths to approximate the vascular anatomy that they traverse to reduce applied thereto. At least one of the limbs can be an adjustable limb having an adjustable length, wherein the length of said at least one adjustable limb can be adjusted while it is being urged against native anatomy. If desired, at least one of said tubular limbs can include a detachable portion that can be replaced with a different detachable portion of a different length. In some embodiments, a distal region of the outer sheath material can be crimped to a distal end of the distal delivery tube by a crimp that compresses the distal delivery tube against the outer sheath material.

The disclosure further provides a method of implanting an implant as set forth herein, including directing a distal end of a guidewire at least partially through a coronary sinus of a heart and over a coronary artery and into the right ventricle or the right atrium, withdrawing the distal end of the guidewire from the patient such that the proximal and distal ends of the guidewire are outside the patient, and the guidewire traverses a loop shaped path through the heart by way of the coronary sinus to surround a native mitral valve, and crimping the crimp of an implant as set forth herein to a proximal end of the guidewire. The method can further include advancing the implant until the arched portion of the bridge of the implant straddles the LCx artery by manipulating the delivery tubes, withdrawing the delivery tubes from the outer sheath material. fixating the implant in place to maintain the length of the sheath by advancing a re-fastenable lock along opposing ends of the outer sheath material, through the patient's vasculature and into the patient's heart, wherein the lock is fastened within the patient's heart, and cutting excess outer sheath material that passes through a proximal portion of the lock.

If desired, the method can further include implanting a transcatheter prosthetic mitral valve within a native mitral valve region, wherein the prosthetic mitral valve applies an outward expansion force on myocardium underlying the coronary artery, and further wherein the bridge inhibits application of compressive pressure to the coronary artery by the prosthetic mitral valve. The method can further include loading the implant into an implant loader to reduce the profile of a bridge, and then introducing the implant into a delivery system prior to introducing the implant into the patient. The method can further include withdrawing a distal sheath of the delivery system to permit the bridge of the implant to expand.

The disclosure further provides an implant that includes an elongate inner tether having a proximal end and a distal end, an outer sheath material surrounding the elongate inner tether, a selectively removable proximal delivery tube disposed over or within the outer sheath material and surrounding a proximal portion of the elongate inner tether, a distal end of the proximal delivery tube being located within a central region of the outer sheath, and a selectively removable distal delivery tube disposed over or within the outer sheath material and surrounding a distal portion of the elongate inner tether, a proximal end of the distal delivery tube being located within the central region of the outer sheath.

If desired, the method can further include implanting a transcatheter prosthetic mitral valve within the native mitral valve region, wherein the prosthetic mitral valve applies an outward expansion force on myocardium underlying the coronary artery, and further wherein the bridge (or other stiffened portion of the implant) inhibits application of compressive pressure to the coronary artery by the prosthetic mitral valve. The method may include releasing the tension in the sheath material of the implant, repositioning the implant, and reapplying the tension to the sheath material. Any suitable amount of tension can be applied to the implant in order to effectuate the desired outcome.

The disclosure still further provides embodiments of a snare catheter that includes an elongate core member having a proximal end and a distal end, an elongate intermediate tubular member having a proximal end, a distal end and defining an elongate lumen therethrough for slidably receiving the elongate core member therein, a collapsible tubular perforated body formed from a plurality of parallel, radially inwardly collapsible elongate members attached at a proximal end thereof to the distal end of the elongate intermediate tubular member, and at a distal end thereof to the distal end of the elongate core member, wherein relative axial displacement of the distal end of the elongate intermediate tubular member toward the distal end of the elongate core member causes the elongate members to expand radially outwardly and to mutually separate, and relative axial displacement of the distal end of the elongate intermediate tubular member away from the distal end of the elongate core member causes the elongate members to collapse radially inwardly and to collapse together. The snare catheter can further include a target wire disposed within a central region of the collapsible elongate members that extends along the elongate core member and has a proximal end attached to the elongate intermediate tubular member and a distal end attached to the elongate core member. The target wire can be configured to assume a first generally straight configuration when the collapsible elongate members is collapsed radially inwardly, and a second substantially non-linear configuration when the collapsible elongate members are expanded radially outwardly. The snare catheter can further include an elongate tubular longitudinally displaceable sheath having a proximal end, a distal end and defining an elongate lumen therethrough for slidably receiving the elongate core member, elongate intermediate tubular member, collapsible elongate members, and target wire therein when the collapsible elongate members are in a generally radially collapsed state.

If desired, the elongate core member of the snare catheter can be a tubular member defining a guidewire lumen therethrough. The snare catheter can be provided with an atraumatic distal tip formed from compliant material that is attached to the distal end of the elongate core member. The snare catheter (or any device described herein) can further include radiopaque marker bands disposed near the distal end of the catheter and the distal end of the elongate intermediate tubular member. If desired, the snare catheter can include a plurality of radiopaque marker bands formed on the target wire. The target wire can be formed at least in part from radiopaque material. The collapsible tubular perforated body can be formed at least in part from radiopaque material.

In some implementations, the target wire can include at least one loop and/or undulation formed therein when it is longitudinally contracted. If desired, the target wire can include a plurality of loops and/or undulations formed therein when it is longitudinally contracted. The target wire and loop (and/or undulation) can substantially lay in a single plane parallel to a longitudinal axis of the catheter when the target wire is longitudinally contracted. The target wire and loop(s) and/or undulation(s) can define a three dimensional geometry when the target wire is longitudinally contracted. If desired, a plurality of target wires can be provided having one or more loops and/or undulations when the target wires are longitudinally contracted. The target wire can include composite wire, such as a wire that includes a core portion made from a first material, and a cladding portion made from a second material different from the first material.

The disclosure further provides a lock delivery catheter that includes an elongate inner tubular member having a proximal end and a distal end, an elongate outer tubular member having a proximal end, a distal end and defining an elongate lumen therethrough for slidably receiving the elongate inner tubular member therein, and a deployable lock attached to the lock delivery catheter including a lock body and a wedge, the wedge being configured to wedge against the lock body when the lock body and wedge are pressed together.

The lock body is typically detachably attached to the distal end of the elongate outer tubular member, and the wedge is typically detachably attached to the distal end of the elongate inner tubular member. The lock delivery catheter can further include at least one guiding suture routed between the lock body and the wedge and extending proximally through the elongate inner tubular member. The at least one guiding suture can be a snare suture including a loop formed at a distal end thereof for attaching to a second suture (e.g., one or both ends of the implant) to facilitate drawing the second suture through the lock delivery catheter. The lock body can include a pin that spans the lock body, and the pin can pass through a portion of the wedge to couple the lock body to the wedge. The pin can pass through a longitudinal groove formed into the wedge, such that the lock body and wedge can slide with respect to each other along the longitudinal groove. The wedge can include a proximal portion defining a proximal opening that extends into a central passage in the proximal portion that divides into two passages that terminate at two distal openings defined in two surfaces that lay on either side of an elongate portion of the wedge that defines a longitudinal slot therein. Each of the two distal openings each can include a suture passing therethrough that extend proximally through the elongate inner tubular member and distally between the lock body and the wedge. The lock body can define a distal opening for routing at least one suture therethrough. The distal opening of the lock body can include at least one distally extending sleeve disposed therein for guiding a suture therethrough. The distal opening of the lock body can include two distally extending sleeves disposed therein for guiding a suture therethrough. At least one of the sleeves can include two concentric sleeves that cooperate to form a telescoping sleeve capable of being adjustable to more than one length. At least one of the sleeves can include an atraumatic distal tip formed thereon. If desired, at least one of the sleeves can include an opening formed through a wall thereof configured to permit a tether to pass therethrough, rather than having the tether traverse the full length of the sleeve.

In some implementations, the lock delivery catheter can further include a handle attached to a proximal portion of the outer tubular member that can be provided with one or more actuators. The lock delivery catheter can be provided with a tether loop routed through a portion of the lock body and extending proximally to a tether clamp, the tether loop being configured to hold the lock body fast against a distal end of the outer tubular member. The handle can be provided with at least one spring loaded clamp configured to selectively maintain tension on a tether of an implant, or on any other desired filament. In some implementations, the distal end of the outer tubular member can be configured to interdigitate with the lock body so that the outer tubular member can transmit torque to the lock body. If desired, the distal end of the outer tubular member can be shaped to guide the lock body into the distal end of the outer tubular member.

The disclosure further provides a cutting catheter that can include an elongate inner member having a proximal end and a distal end with a distally facing blade mounted on the distal end, and an elongate outer tubular member having a proximal end, a distal end and defining an elongate lumen therethrough for slidably receiving the elongate inner tubular member therein, wherein the elongate outer tubular member defines a pair of laterally offset holes therethrough near the blade for receiving a suture material therethrough, wherein distal advancement of the elongate inner member with respect to the elongate outer tubular member passes the blade past the suture to cut the suture. If desired, the distally facing blade can be mounted on a generally planar distal region of the elongate inner member that is configured to slide within a flattened distal portion of the elongate outer tubular member. A stylet may also be provided that is fed through the pair of laterally offset holes for initially capturing the suture material, the end of the implants, or other tether.

The disclosed devices may be used in methods of improving the function of a mitral valve in a subject in which an annuloplasty element, for example an element that exerts compressive tensile remodeling forces on the mitral valve (such as a tensioning element), is introduced at least partially around the mitral valve, for example at least partially through the coronary sinus and over a coronary artery. The protective device is placed between the annuloplasty element and the coronary artery, with the annuloplasty element separated from the underlying coronary artery by the bridge of the device. Reinforcing core elements can then be removed from the device and a lock can be introduced over the device and advanced to a location where it can maintain tension on the implant.

Compressive remodeling forces are exerted by the annuloplasty device (for example by applying tension on a tensioning element to alter the shape or configuration of the mitral valve annulus to reduce its circumference) while supporting the annuloplasty element on the bridge to inhibit application of pressure to the coronary artery. The function of the mitral valve in the patient is thereby improved without impairing coronary blood flow.

In one example of a method in accordance with the disclosure, a catheter is introduced into the great cardiac vein, and a guidewire or other penetrating device (such as a needle, radiofrequency energy ablation device or laser ablation device) into a basal blood vessel such as the first septal coronary vein. From there the penetrating device directly traverses under imaging guidance the septal myocardium or annulus fibrosis and reenters the right ventricle or right atrium. The guidewire is then retrieved using, for example, a snare catheter as disclosed herein. The snare catheter is then collapsed to draw the guidewire into a body of the target catheter, and the guidewire is percutaneously withdrawn from the patient, resulting in both ends of the guidewire being exposed. The distal end of the implant is then crimped onto the proximal end of the guidewire, and the implant is advanced into the body until the bridge portion of the implant straddles a coronary artery, such as the left circumflex ("LCx") artery. The location of the LCx artery can be identified, for example, by radiocontrast angiography or by fusion of prior computed tomography angiography and live X-ray or using intravascular ultrasound. In an alternative approach, coronary veins are entered in the other direction from the right atrium or right ventricle under imaging guidance into a branch of the coronary sinus.

At this point, the proximal end of the guidewire and the crimp attaching the guidewire to the distal end of the implant are preferably externalized with respect to the patient's body, as well as the proximal end of the implant. The distal and proximal delivery tubes are then preferably removed, leaving behind the implant, wherein the sheath material is long enough to extend out of the patient. A lock can then be threaded over both proximal and distal sheath portions of the implant that respectively contact the bridge portion using a lock delivery catheter, and the lock can be advanced into the patient's heart. Tension can be imposed in the sheath of the implant to achieve the desired anatomical change. Tension is preferably applied to the proximal and distal sheath portions under imaging guidance until the desired degree of mitral annular circumferential reduction is accomplished, or until the mitral valve regurgitation is reduced, or until other deleterious endpoints are achieved such as mitral valve inflow obstruction. The lock can be locked via manipulation of the lock delivery catheter, which then in turn can be removed, and a cutting catheter can be advanced over the proximal and distal sheath portions of the implant. The sheath portions are preferably internal to the lock and lock catheter. Excess sheath can be removed using the cutting catheter as disclosed herein, and the cutting catheter can both be removed from the patient, completing the procedure.

In accordance with further aspects, the disclosure provides an implantable pacing system configured and arranged to circumnavigate a loop path in a heart. The system includes an elongate inner tether having a proximal end and a distal end, an outer sheath material surrounding the elongate inner tether having a proximal end and a distal end, at least one electrical conductor disposed along or within at least one of the elongate inner tether and the outer sheath, a cardiac pacing controller including a power source, a pulse generator, and control circuitry operably coupled to the at least one electrical conductor, at least one cardiac pacing electrode configured and arranged to be implanted in cardiac tissue, the at least one cardiac pacing electrode being electrically coupled to the cardiac pacing controller by way of the at least one electrical conductor, and a lock securing the proximal end and distal end of the outer sheath material.

In some implementations, the lock can be coupled to the cardiac pacing controller. The at least one electrical conductor is disposed at least partially within the elongate inner tether. If desired, the lock can include cardiac pacing lead routed therethrough. Electrical communication can be established with the cardiac pacing lead by engaging a portion of the lock. In some implementations, the pacing system can further include at least one lumen along a length of the outer sheath for receiving a pacing lead, wherein the pacing system can be slid along the pacing lead into the coronary sinus. The at least one lumen can be configured to direct the pacing lead toward the cardiac pacing controller. In some embodiments, the system can include a protective bridge for spanning the LCx artery when in the coronary sinus near the septal wall as described elsewhere herein. In some embodiments, at least a portion of the cardiac pacing controller can be disposed within the outer sheath.

The pacing system can further include an electrical battery that is at least partially disposed within the outer sheath. The pacing system can further include a circuit board that is at least partially disposed within the outer sheath. The pacing system can further include communications circuitry that is at least partially disposed within the outer sheath.

If desired, the pacing system can further include at least one sensor circuit that is at least partially disposed within the outer sheath, the at least one sensor module including at least one sensor (e.g., sensing circuitry) for sensing at least one biological parameter. For example, the at least one sensor circuit/module can include at least one pressure sensor for detecting blood pressure, or at least one of a chemical sensor, a distance sensor, a sensor having circuitry to detect electro physiological data, a movement sensor, and a location sensor.

In some implementations, the at least one electrical conductor can terminate at the lock. If desired, the system can further include at least one pacing lead (and/or electrical sensor for sensing cardiac electrical signals) formed into a surface of the outer sheath. The at least one pacing lead can be configured and arranged to interface with the Right Atrium. If desired, a further pacing lead can be configured and arranged to interface with the Right Ventricle, or a cardiac vein such as the septal vein. If desired, the controller can be configured and arranged to provide at least one of pacing, defibrillation, measurement and control.

In some implementations of the pacing system the inner elongate tether can include a loop antenna that conducts signals to and from the controller. In further implementations, the pacing system (or other system) can further include a reservoir for containing a beneficial agent coupled to a dispenser controlled by the controller. For example, the beneficial agent can include a medication, a gene therapy material, and/or living cells for seeding at least one location of the heart that is damaged.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 4E-4F are views of a further embodiment of an implant in accordance with the present disclosure.

FIGS. 5A-5E illustrate various aspects of a crimp in accordance with the present disclosure used to connect a distal end of an illustrative implant to a proximal end of a guide wire that has been directed through a patient's vasculature.

FIG. 8 is a rear perspective view of the heart showing the tilted plane of the coronary sinus cerclage annuloplasty. The drawing schematically illustrates a smaller traditional surgical mitral valve annuloplasty ring over the mitral valve annular plane and the larger coronary artery cerclage in a plane that is tilted to the mitral plane so as to encompass the left ventricular outflow tract.

FIGS. 11A and 11B illustrate aspects of a lock delivery system in accordance with the disclosure.

FIGS. 15A-15E illustrate aspects of a further embodiment of a lock and lock delivery system in accordance with the present disclosure.

DETAILED DESCRIPTION OF ILLUSTRATIVE EMBODIMENTS

I. Explanation of Terms

Figure 1B:
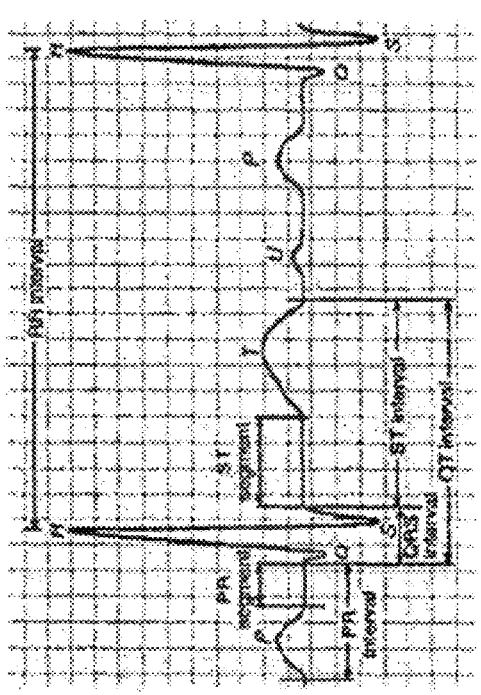
FIGS. 1A-1C illustrate aspects of cardiac pacing in accordance with the present disclosure.
Figure 1C:
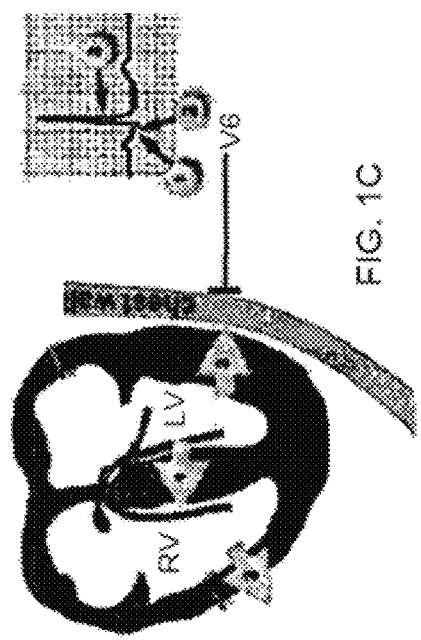
Figure 1A:
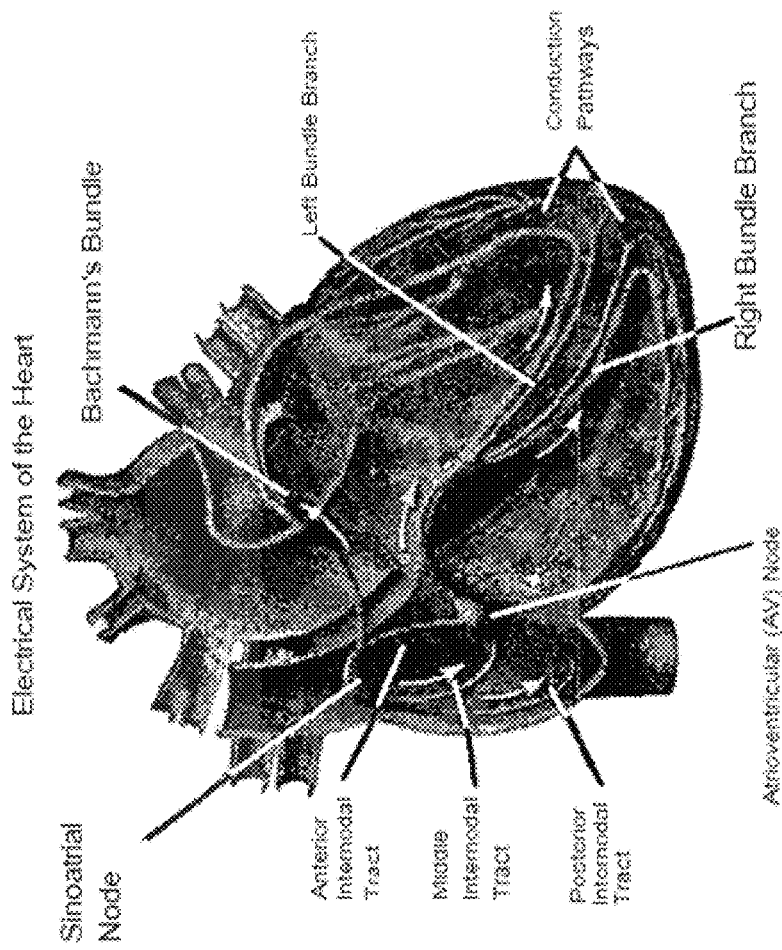

Unless otherwise noted, technical terms are used according to conventional usage. In order to facilitate review of the various embodiments of the disclosure, the following explanation of terms is provided:

"Annuloplasty element" refers to a device that induces reshaping of an annulus of the heart to repair valvular insufficiency. Such devices include those that are placed in the coronary sinus and exert their action by compressive forces on the annulus, for example by expansion of a resilient annuloplasty element, or placement of the annuloplasty element under tension, as in cerclage annuloplasty.

The term "comprises" means "includes without limitation." Thus, "comprising a guiding catheter and a guide wire" means "including a guiding catheter and a guide wire," without excluding additional elements.

The term "guide wire" refers to a simple guide wire, a stiffened guide wire, or a steerable guide-wire catheter that is capable of puncturing and/or penetrating tissue. The guide-wire also can deliver energy to augment its ability to penetrate tissue, for example by puncturing it, delivering radiofrequency ablative energy or by delivering laser ablative energy.

These are examples of a "penetrating device," which is a device capable of penetrating heart tissue, such as the myocardium.

As used herein, the term "ligature" is meant to encompass any suitable tensioning material and is not limited to only suture material. The term "tensioning material" or "ligature" includes sutures and annuloplasty wires.

A "mitral valve cerclage annuloplasty" refers to an annuloplasty procedure in which a tensioning element is placed through at least a portion (and preferably all) of the coronary sinus so that the circumferential tension is delivered around the mitral valve annulus and so that a tensioning element can be placed under selective degrees of tension to perform the annuloplasty. An example of cerclage annuloplasty is disclosed in co-pending prior application Ser. No. 11/127,112 (U.S. Patent Publication No. 2005/0216039), and the disclosure of the description of that technique is incorporated herein by reference for any purpose whatsoever. However, the mitral valve cerclage annuloplasty technique also includes other cerclage trajectories, such as those disclosed herein, including a trajectory through a proximal coronary septal perforator vein and myocardium or annulus fibrosis interposing between that vein and the right ventricle or right atrium to create circumferential cerclage annuloplasty tension.

The protective (or protection) device disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and nonmagnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

"Tensioning material" is any material suitable to perform a coronary sinus mitral valve cerclage annuloplasty, in which an encircling material is placed under tension to remodel the mitral valve annulus. Examples of suitable tensioning materials are preferably a sheath material (e.g., made from a woven polymeric material) as described herein.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

II. Protection Devices to Protect Coronary Arteries

Coronary sinus mitral valve cerclage annuloplasty is an example of a percutaneous mitral valve repair procedure for which the disclosed protective device can be used. Although the device and methods of its use are broadly applicable to any prosthetic annuloplasty element placed in the coronary sinus, the methods will be described in connection with the particular example of cerclage annuloplasty. This specific example should not be construed to limit the procedure to use with cerclage annuloplasty, but only to illustrate its use in a particular embodiment.

Cerclage annuloplasty percutaneous repair carries a lower risk or morbidity than conventional mitral valve surgery, and thus can be used in patients who have less severe or more severe valvular dysfunction. Placing cerclage tethers, or ligatures, at least partially through the coronary sinus takes advantage of the proximity of the coronary sinus to the mitral valve annulus, and of the ready catheter access to the coronary sinus and tributary veins. These approaches also have limiting drawbacks, however, in that compression of nearby coronary artery branches is a serious risk in a majority of human subjects. The coronary sinus usually runs superficial to the circumflex coronary artery and its marginal branches near the great cardiac vein, and therefore trans-sinus annuloplasty can transmit pressure sufficient to constrict or occlude the coronary artery or its branches. Devices and methods that prevent this compression of the coronary artery, such as those disclosed herein, can dramatically increase the safety and efficacy of trans-sinus mitral cerclage annuloplasty.

An exemplary transcatheter-mitral-valve-cerclage annuloplasty involves the introduction of a tensioning material or device around the mitral valve annulus using a guiding catheter and a secondary catheter, such as a steerable microcatheter directing coaxial guide wires or canalization catheter. Access to the area around the mitral-valve annulus can be accomplished using a variety of percutaneous approaches, including access from and through the coronary sinus. In particular embodiments, a tensioning material that constitutes a portion of an implant is applied around the mitral-valve annulus along a pathway that, in certain embodiments, includes an extra-anatomic portion. For example (and without limitation), the tensioning material can traverse a region between the anterobasal-most portion of the coronary sinus and the coronary-sinus ostium. As another non-limiting example, such tensioning material can be applied across the atrial aspect of the mitral valve from the posterolateral aspect to the anterior aspect of the coronary sinus, or from the septal aspect to the lateral aspect of the mitral-valve annulus. This procedure reduces the mitral annular cross-sectional area and septal-lateral wall separation, thereby restoring a line of coaptation of the mitral valve.

Because it has been found that mitral annuloplasty via the coronary sinus unintentionally transmits pressure sufficient to constrict or occlude the underlying coronary artery, the devices disclosed herein have been developed to increase the safety and efficacy of the procedure. The disclosed improved devices and related methods protect an underlying vessel from compression during mitral annuloplasty in which a cerclage ligature extends at least partially through the coronary sinus over a coronary artery. As discussed in U.S. patent application Ser. No. 15/056,599, filed Feb. 29, 2016, a coronary protection element is disclosed for use with a cerclage device. However, the presently disclosed embodiments provide significant improvements over that disclosure.

Figure 2:
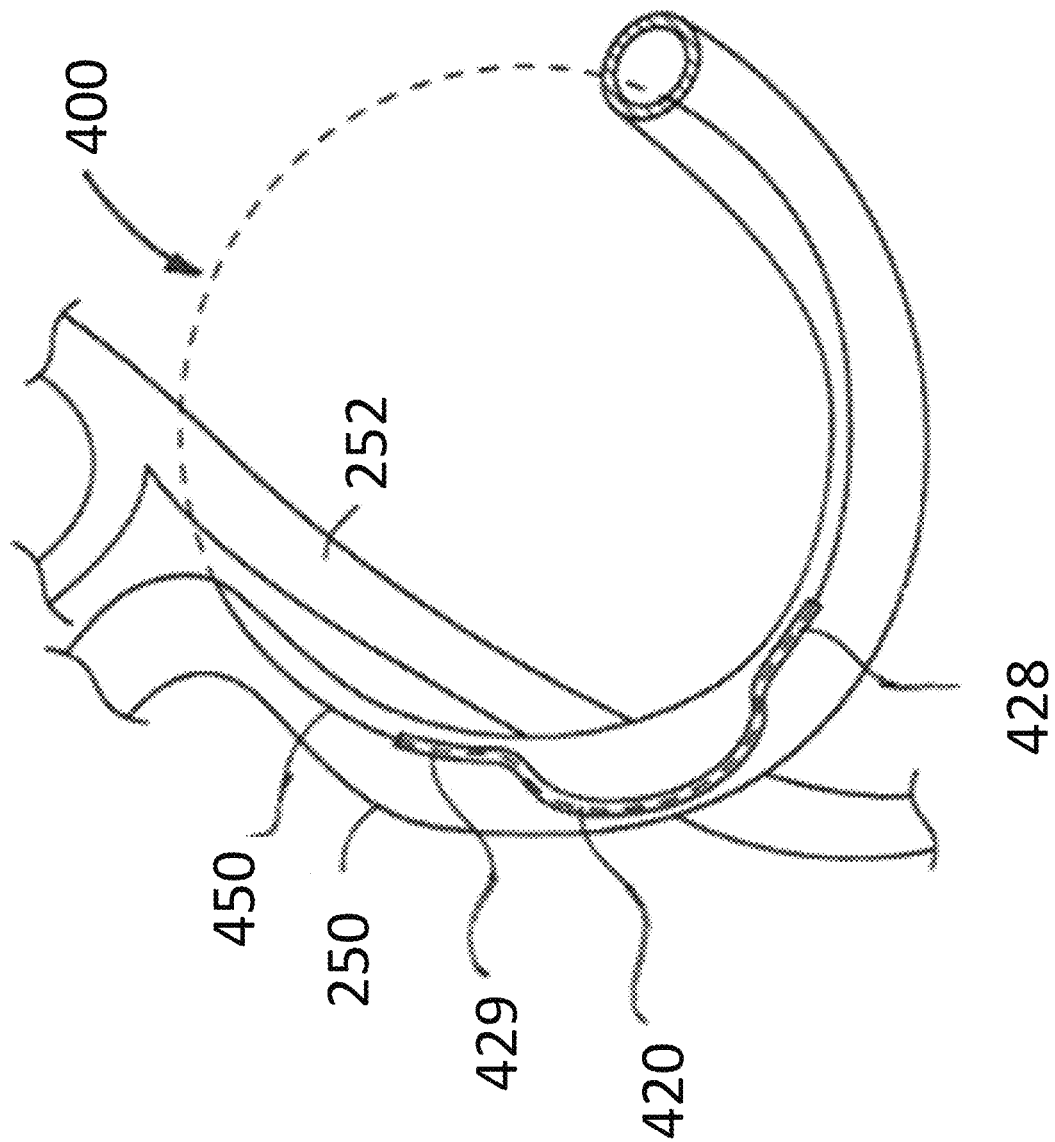
FIG. 2 is a schematic view showing an exemplary coronary protective device in position during a cerclage annuloplasty procedure.

FIG. 2 schematically illustrates the use of implant 400 using a protection device 420 in a mitral valve cerclage annuloplasty procedure. FIG. 2 depicts sheath material 450 used as a tensioning element (in a preferred embodiment, braided suture material) extending through a portion of the coronary sinus 250 over a circumflex coronary artery 252. FIG. 2 shows implant 400 positioned within coronary sinus 250 with protection element 420 extending over coronary artery 252, and proximal and distal portions 428, 429 being located on either side of coronary artery 252. As tension is placed on the tether portion 450 of implant 400, the proximal and distal portions 428, 429 are held in place on either side of coronary artery 252 and transmit compressive forces to the wall of coronary sinus 250 instead of on to underlying coronary artery (LCx) 252.

FIGS. 3A, 3B, 3C and 3D provide an alternative view of the function of cerclage annuloplasty protection device 400.

Figure 3A:
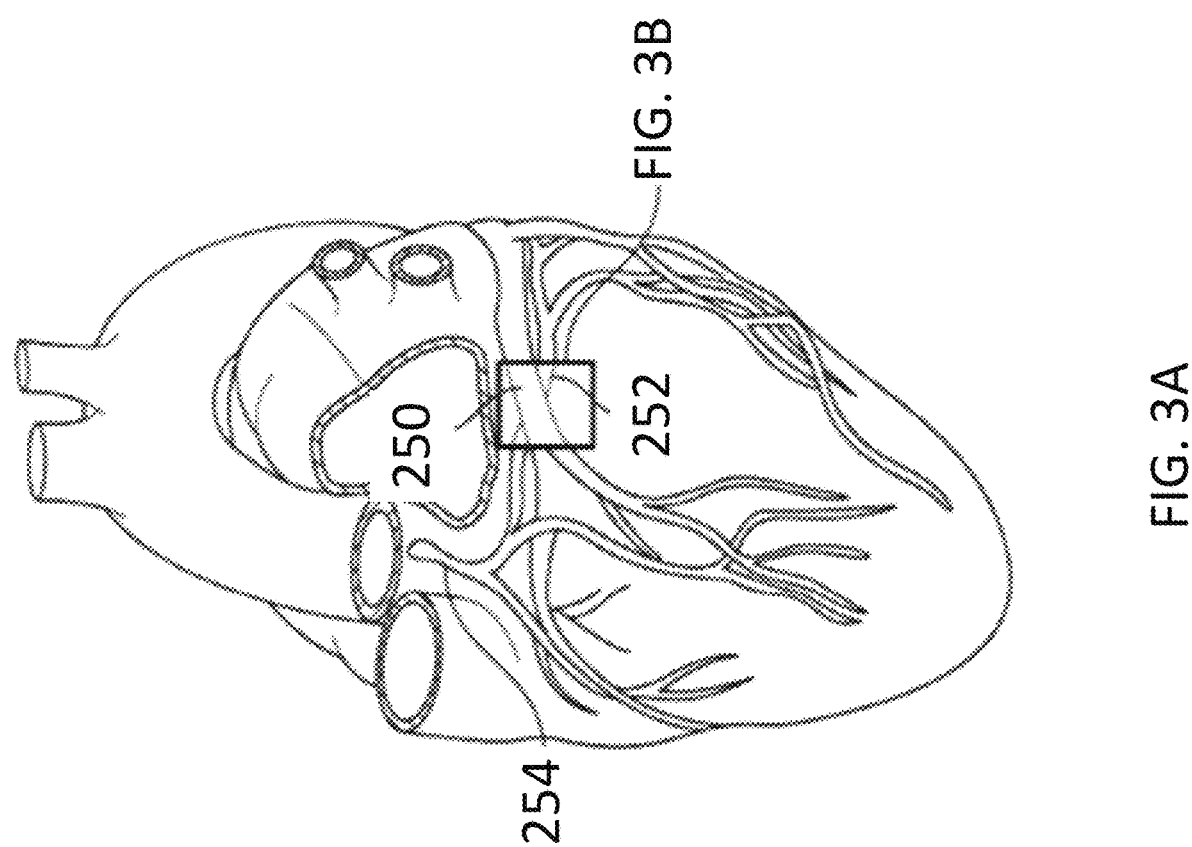
FIG. 3A is a left lateral external perspective view of the heart showing the lateral coronary artery branching from the ascending aorta, the branch of the lateral circumflex artery, and the great cardiac vein.
Figure 3D:
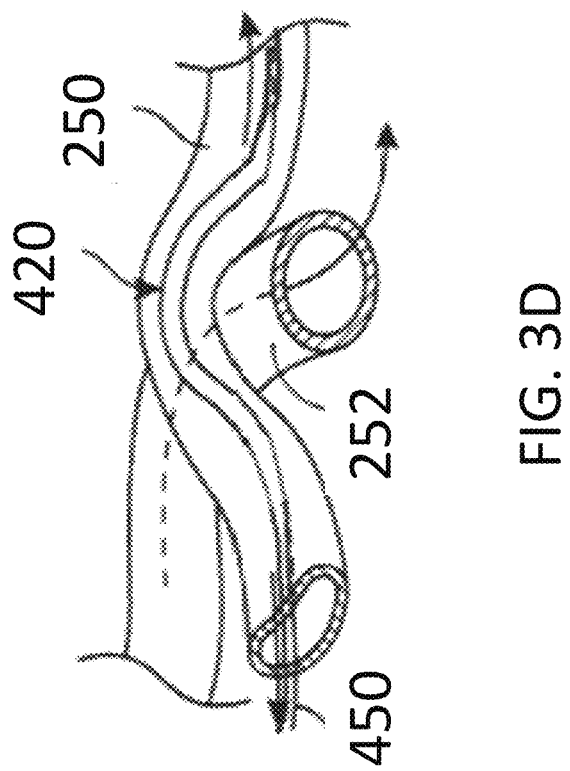
FIG. 3D is an enlarged view of this same structure showing placement of the protective device over the ligature within the coronary sinus superficial to the coronary artery.
Figure 3B:
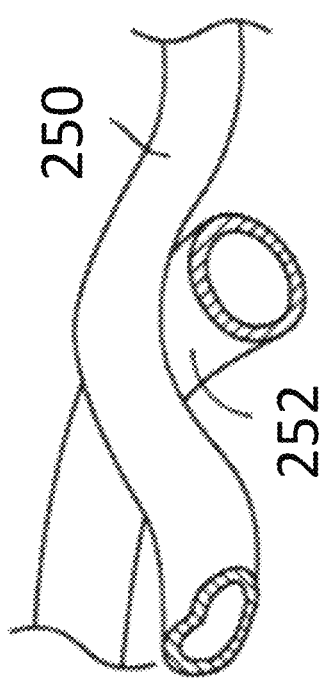
FIG. 3B is an enlarged view of a section of the arteries showing the coronary sinus crossing superficial to the left circumflex coronary artery at the level of the great cardiac vein.
Figure 3C:
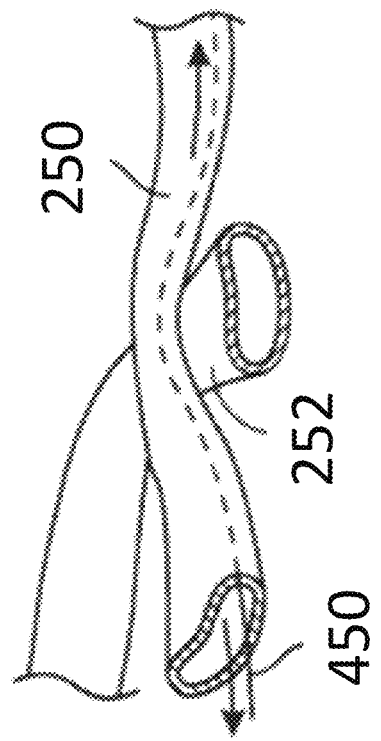
FIG. 3C is a view similar to FIG. 3B but showing placement of a ligature (for example, and without limitation, a wire or suture) during annuloplasty without the protective device in place. When the ligature is tightened during the annuloplasty procedure, pressure is exerted on the branch of the coronary artery, restricting blood flow and myocardial perfusion.

FIG. 3A shows the external anatomy of the heart, with coronary sinus 250 extending over a circumflex branch 252 of a left coronary artery 254. FIG. 3B shows an enlarged view of the overlapping relationship of coronary sinus 250 to coronary artery 252. FIG. 3C illustrates hollow tether 450 placed under tension during cerclage annuloplasty which is compressing underlying coronary artery 252 and interfering with myocardial perfusion. FIG. 3D shows hollow tether 450 extending through protection device 420 which is inhibiting the application of compressive force to coronary artery 252 which therefore remains patent and able to normally perfuse myocardial tissue.

It will be appreciated that the bridge/protection device (e.g., 400) can assume a variety of shapes and configurations that support the hollow tether material 450 away from an underlying coronary artery (e.g., LCx). The protection device/bridge 420 can be pre-shaped to the desired configuration, or it can be made of a memory alloy material that is generally linear when being advanced through the vasculature but assumes the desired protection device shape once it is fully deployed. The bridge 420 can have curvature in three dimensions, as desired, to conform to a unique anatomy of an individual.

FIGS. 4A-4D illustrate an embodiment of an implant 400 that includes a protection bridge 420. A distal end of the implant 400 is connected to a crimp 570 to facilitate its delivery as set forth below. A distal delivery tube 440 is slipped over a distal portion of a sheath 450 that houses various components of the implant 400. The crimp 570 is crimped at its proximal end around the distal end of the sheath and components inside the sheath at the distal end of the implant 400.

As illustrated in FIGS. 4A-4D, the implant 400 includes an arch-shaped protection element 420. A hollow tether 410, such as a small diameter braided polyester suture, is laid on top of the protective arch 420, and secured in place, for example, by suture loops (not shown), or one or more pieces of shrink tubing (not shown). In one implementation, a piece of shrink tubing is slid over tether 410 and protective arch 420, and shrunk in place, holding tether 410 in place on the upper surface of the arch 420 from end to end. If desired, this shrink tubing can extend beyond the ends of the protection element 400 to act as a strain relief to provide a gentler transition in stiffness at the ends of the element 420. Also, if desired, additional or alternative strain reliefs 430 can also be provided at the ends of the protective element 420, also surrounding the tether 410. A sheath 450, such as a larger diameter braided suture, is then fit over the assembly of elements 410, 420, and 430, for example. Sheath 450 narrows in the regions where the protective element 420 is not present. A distal delivery tube 440 is slid over the distal region of the sheath 450, and a proximal delivery tube 470 is slid over the proximal region of the sheath 450, and if desired, crimped in place at the distal and proximal ends of the implant, respectively.

Figure 4A:
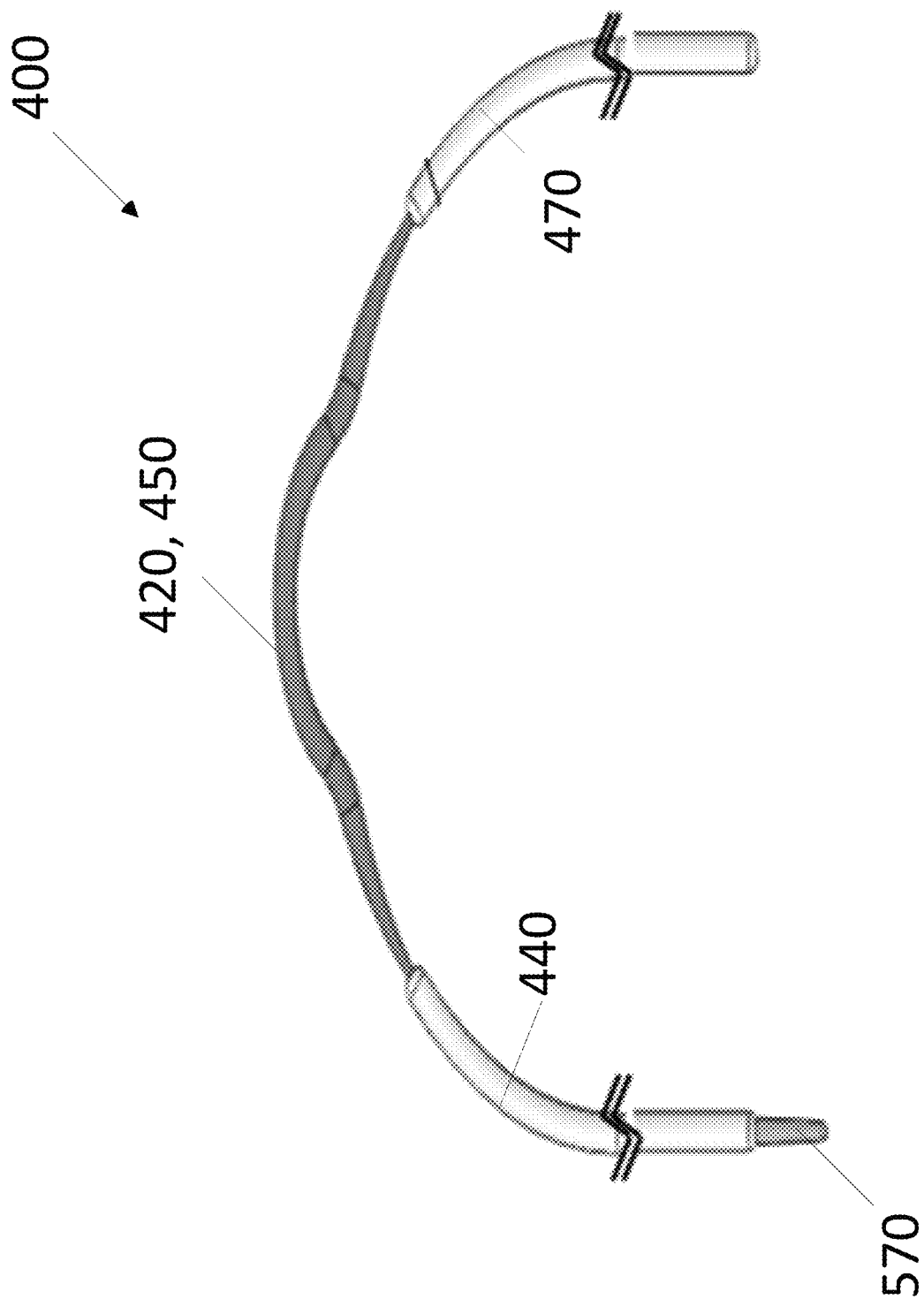
FIG. 4A is a schematic view of a portion of an implant in accordance with the present disclosure.
Figure 4B:
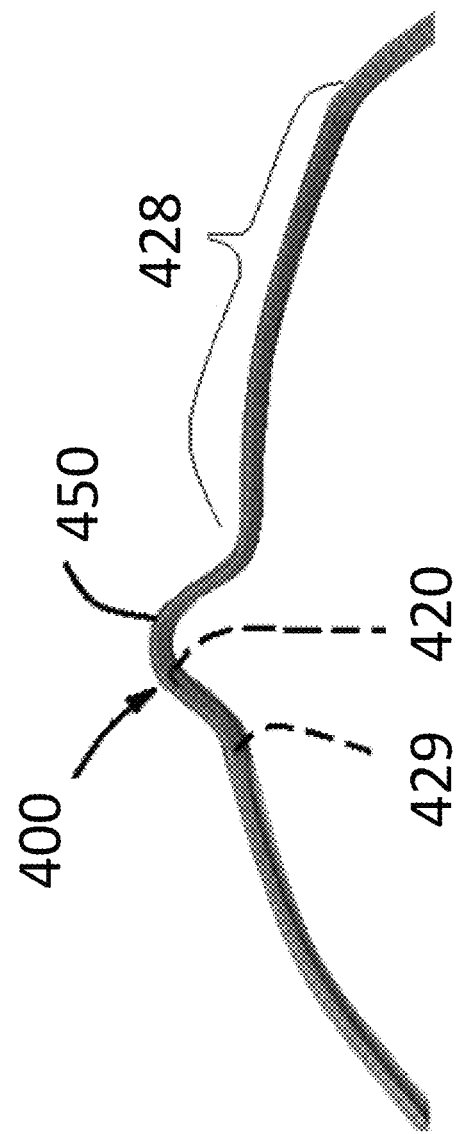
FIG. 4B is a side view of an illustrative protection element in accordance with the present disclosure.

FIG. 4B illustrates an embodiment of a protection device 420, or arch, that has a significantly elongated proximal portion 428 that forms a "landing zone", or stiff, stable structure when implanted within the coronary sinus. This landing zone can then serve as a location for implanting a replacement valve after the transcatheter annuloplasty procedure has been completed. Specifically, having a relatively rigid surface within the heart provided by the landing zone created by elongated proximal portion 428 facilitates anchoring of such a replacement valve to the native tissue. The proximal portion 428, if provided, can thus have any suitable length between, for example, 3 and 80 mm, and in any desired increment of 1 mm therebetween. The distal portion 429, if provided, can have any suitable length between 0.5 mm and about 10 mm, and in any desired increment of 0.5 mm therebetween.

The protection element 420 can be made from rolled wire that is radiopaque, such as 0.020 inch by 0.070 inch Ni Ti alloy shape memory wire, but it will be appreciated that other materials can be used of similar or differing dimension. Being made from a shape memory material allows the bridge 420 to be deformed (for example toward a linear configuration) that is adaptable to introduction through the vascular system. However, the shape memory material returns to the arched configuration shown in the drawings after the device is deployed.

The arch 420 may have a round cross section or rectangular cross section having a diameter, or respective height and width between about 0.010 inches to about 0.080 inches and in any desired increment of 0.001 inches between those values. As illustrated, the ends of the protection element 420 are preferably rounded so as to not cause trauma to the wall of the coronary sinus as it is advanced. The protection device 420 preferably has an arcuate, or semi-circular shape of sufficient radius to extend closely over an underlying coronary artery (e.g., the LCx) to inhibit the transmission of compressive forces from the tension element to the underlying artery. The compressive forces are instead distributed on and along the protection device to protect the artery from compression that impairs myocardial perfusion. Protection element end portions 428, 429 effectively form "feet" that can rest against a wall of the coronary sinus while straddling a coronary artery to retain protection device 420 in position over the left circumflex artery and bear and distribute the compressive forces that are applied by the sheath 450 when the under tension after the delivery tubes 440, 470 are removed.

Figure 4C:
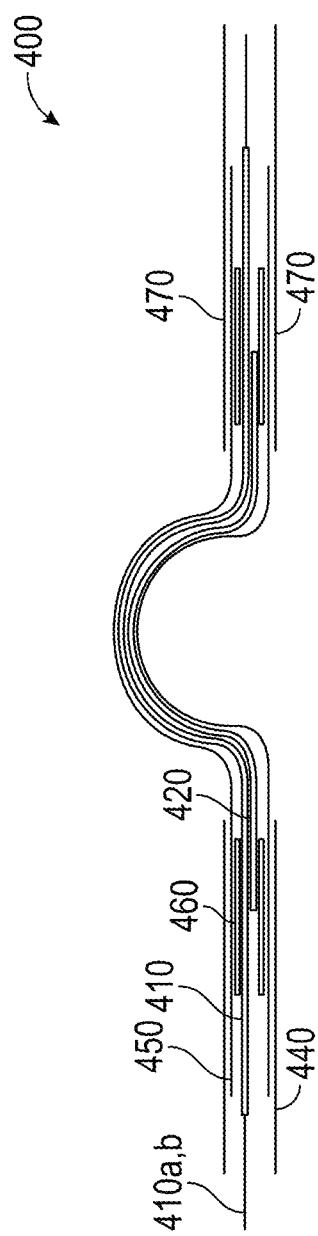
FIG. 4C is a cross-sectional schematic view of an illustrative implant in accordance with the present disclosure.

The embodiment of FIG. 4C preferably has a central arch bridging a linear distance at its
base of from about 0.4 inches to about 0.7 inches, for instance, in any desired increment of 0.01 inches therebetween. The illustrated central arch has a height h from about 0.10 inches to about 0.20 inches high, for instance, in any desired increment of 0.01 inches therebetween.

The proximal and distal portions of the exterior sheath and the delivery tubes 440, 470 are preferably coated with a lubricious hydrophobic or hydrophilic material, such as PTFE, PVDF, other suitable fluoropolymer or PVP, for example.

Figure 4D:
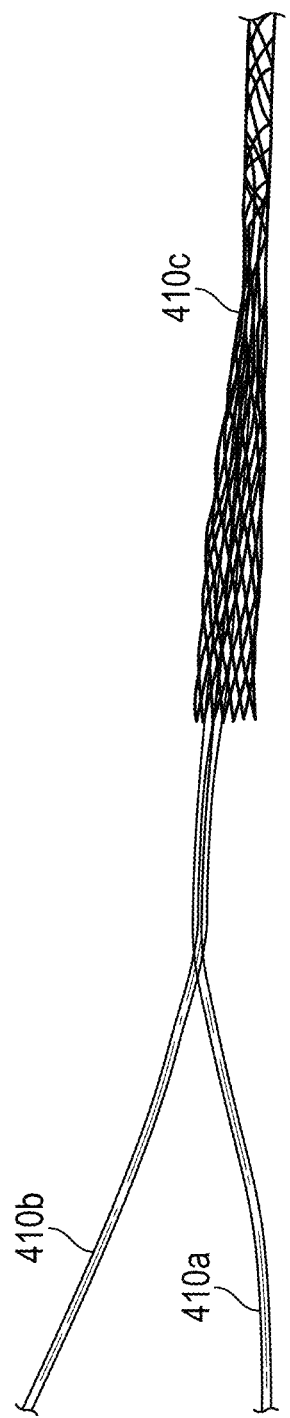
FIG. 4D is a view of an inner tether suitable for use in the implant of FIG. 4C.

As illustrated in FIG. 4D, the inner tether 410 can be composed of a plurality of sub-components. The illustrated embodiment of inner tether 410 can be composed of an innermost metallic, radiopaque wire 410a (e.g., platinum), surrounded by a heat shrunk tubing 410b (e.g., PTFE, PET). These nested components can then accordingly be housed within braided suture 410c. Preferably, the lengths of components 410a, 410b, 410c are coextensive with sheath 450 and crimped to sheath 450 at the proximal and distal ends of the implant 400.

Preferably, the inner tether is 410 radiopaque along its entire length to enhance visualization thereof during and after installation. While radiopacity of inner tether 410 can be enhanced by the presence of a metallic (e.g., platinum) wire, the wire, or filament, can be formed from a tungsten loaded polymer, a tantalum loaded polymer, and/or the braided suture material 410c can be used that is impregnated in one manner or another (e.g., by incorporation into the underlying polymer, or into the woven material) with one or more of bismuth, tungsten, tantalum, barium sulfate, and the like.

The delivery tubes 440, 470 are disposed over the sheath 450, and may abut, or be located near, the proximal and distal ends of the protection bridge 420. The removable delivery tubes are assembled over the continuous outer tether 450 on each side, running from the protection bridge to the exchange crimp (as illustrated in FIG. 4A) to aid in exchanging out the guide wire for the cerclage implant. Alternatively, they can be routed underneath the outer sheath 450. The removable delivery tubes can be made from polymeric material, for example, such as PEEK, HDPE, or the like, as desired. When the implant is in place, the removable delivery tubes can be removed by pulling them out. The sheath 50 surrounding the structure can, in turn, include a lubricious coating along at least a portion of its length or all of its length, such as a hydrophobic coating (e.g., PTFE, PVDF) or a hydrophilic coating (e.g., PVP). This can be provided, for example, in the form of one or more additional layers or adjacent and/or overlapping tubes of PTFE shrink tubing. The overlap regions can act as a strain relief to help provide regions of transitioning stiffness. The shrink tubing can be a multi-layer co-extrusion as described elsewhere herein that can include an intermediate braided layer formed from polymeric or metallic material, and may include radiopaque material.

In some implementations, sheath 450 can be made from a 1-2 mm ultra high molecular weight polyethylene ("UHMWPE") coreless round braid from DSM, Dyneema or Teleflex. In some embodiments, the tether/sheath 450 can be loaded with at least 20% bismuth by weight to enhance radiopacity. For example, the sheath may be loaded with between about 20 and about 70% bismuth or barium sulfate, or to any degree therebetween in increments of about 1% by weight. Additionally or alternatively, additional or alternative radiopaque materials can be incorporated into the sheath material, such as tungsten, tantalum, and barium sulfate. These materials can be incorporated, for example, as drawn metallic (e.g., platinum, or other radiopaque material) wires incorporated into the braiding, such as by weaving, or by directing the drawn wire along a central channel defined within the tether.

FIGS. 5A-5E depict various views of a crimp 570 that provides a transition region from a proximal end 502 of a guidewire to a distal end of the implant 400. A second crimp at the proximal end of the implant 400, if provided, can provide an alternative or additional structural attachment location for affixing the proximal end of the sheath 450 to a proximal end of the inner tether 410. As illustrated, the crimp 570 includes an external proximal tapering generally conical surface, an external distal tapering generally conical surface and two intermediate tapering external conical surfaces. The distal end of the crimp is smaller in diameter than the proximal end of the crimp 570 to define a relatively large proximal bore for receiving the distal end of the implant 400 housed within and including distal end of sheath 450, and a relatively narrow, intersecting distal bore that is sized to receive the proximal end 502 of a guidewire. The crimp 570 is preferably made from a deformable metallic material that is initially affixed to the distal end of the implant 400. Once the guidewire is introduced and has been properly routed through the heart and out of the body (discussed in further detail below), the crimp 570 of implant 400 is then crimped onto the guidewire (e.g., with a hand crimper), and the implant 400, including the proximal and distal delivery tubes, protection element 420 and sheath 450 are advanced through the vasculature until the protection element straddles the LCx artery. It will be appreciated that the protection element 420 can be omitted from the implant, and, for example, replaced with a relatively straight structural element (or no stiff element at all) for patients having anatomy that does not require the arched protection element.

Figure 4F:
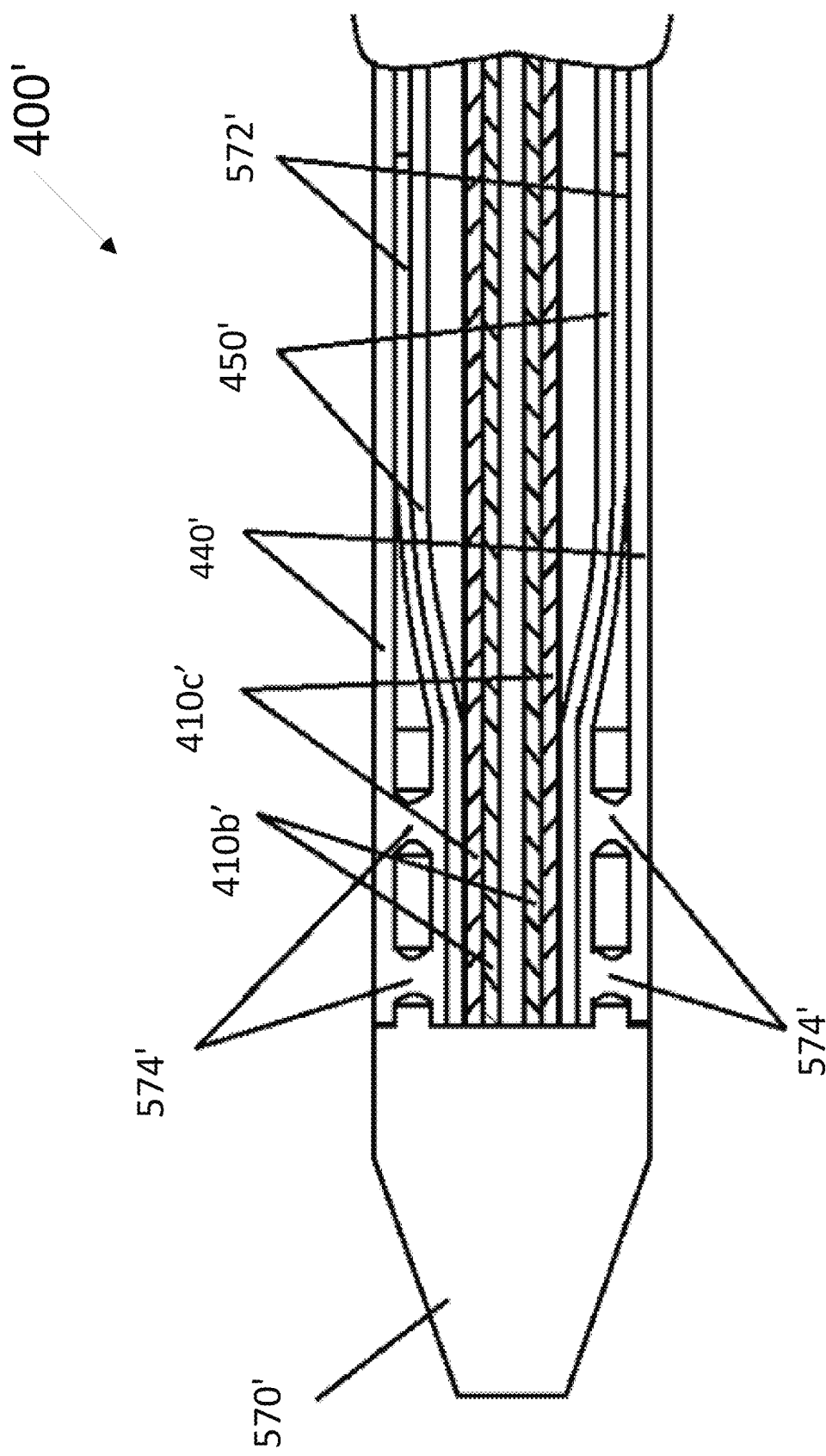

FIGS. 4E and 4F illustrate a further embodiment of an implant 400' in accordance with the present disclosure. FIG. 4E illustrates a distal and central portion of implant 400'. Implant 400' includes an innermost core wire (e.g., of platinum) 410a' that is preferably housed within an elongate Pebax tube 410b'. The assembly of components 410a', 410b' are then introduced into a tubular (e.g., 0.5 mm) braided suture 410c'. This collection of components is then introduced into a shorter tube 480', preferably also of Pebax or other suitable thermoplastic material. Tube 480' is preferably only several inches long and sufficient to span the full length of protective bridge 420'. Components 410a', 410b', 410c' and 480' are then heat shrunk in a heating operation. The heating operation causes the Pebax material to melt in between the fibers of the braided suture 410', enhancing its stiffness in the region of the protective bridge 420'. The heat fused assembly of components 410a', 410b', 410c' and 480' are then laid over the upper surface of bridge 420', and then introduced into a further (e.g., 1 mm diameter) braided polymeric suture 450'. The suture 450 holds the assembly of components 410a', 410b', 410c' and 480' in place on the upper surface of bridge 420'. Next, an outer tubular layer 490' of Pebax or other suitable thermoplastic material is fitted over the portion of the outer sheath 450' that straddles the bridge 420'. This collection of components is then heat shrunk again to cause the polymeric material of components 480' and 490' to fuse into the fibers of braided sheath 450', further enhancing stiffness, and also providing a smooth surface with superior stress transition aspects along the length of the implant 400'. Inner radiopaque wire 410a' preferably does not traverse the entire length of the implant, but instead preferably occupies a central region that is between about 100 cm and 200 cm long (e.g., about 170 cm long) with roughly equal lengths on either side of bridge 420'.

As further illustrated in FIG. 4E, a distal delivery tube 440' is also presented, and also preferably made from a thermoplastic polymer (preferably thermoplastic elastomer "TPE") such as Pebax. As illustrated, delivery tube 440' includes a flared proximal end suitable for abutting or even partially overlapping the distal end of bridge 420'. A proximal delivery tube 470' (not specifically illustrated) can similarly be provided with a distal flare that similarly abuts or overlaps the proximal end of the bridge 420'.

FIG. 4F shows a distal region of implant 400' showing how it is affixed to a distal crimp 570' in cross-section. Distal crimp 570' includes a distal passage for receiving a guidewire (not shown) and a proximal passage for receiving a plurality of nested tubular components. The innermost component illustrated in FIG. 4F includes Pebax tube 410b' which is nested inside braided suture 410c'. Core wire 410a' does not extend all the way to the crimp in this embodiment, although it could if desired. Component 410c' is disposed within outer sheath, or braided suture 450'. The distal end of suture 450' is in turn disposed within a short (e.g., 2-3 cm) section 572' of polymeric tube, such as Pebax. The distal end of tub 572' is fit into a cylindrical opening in the proximal face of crimp 570'. Outer delivery tube 440 is then slid over an exterior proximal portion of crimp 570', which may be recessed. Proximal portion of crimp 570' includes a plurality of holes, or windows 574', formed therethrough. Once the components are assembled, the assembly is heat shrunk to cause the polymers in the distal tip of delivery tube 440' to fuse with tube 572' through windows 574', thereby affixing crimp 570' to implant 400'. The distal end of tube 440' may initially be outwardly flared to help with initially fitting the components into or onto crimp 570'. While not shown, the proximal end of the implant 400' can be constructed similarly and fused without a crimp, for example, by heat shrinking the proximal end of the proximal delivery tube 470' to the interior components.

The disclosure also provides a version of implant 400' that does not include a protective bridge. The construction this embodiment is the same as implant 400', except that in the central region where the bridge 420' would otherwise be, the bridge 420' is not present, and tube 480' is not included. Instead, the assembly of components 410a', 410b' and 410c' are heat fused, and introduced into outer sheath 450'. In order to indicate the location of the center of the implant 400', a marker band is slid to that location over sheath 450' and held in place by sliding another polymeric tube, preferably of Pebax, over the marker, and heat shrinking it into place. If desired, a further piece of heat shrink tubing can be shrunk over the marker that may also be at least partly radiopaque to both enhance radiopacity but also to increase the thickness at the center of the implant to prevent it from being pulled through the lock as a safety feature during implantation.

III. Percutaneous Mitral Valve Cerclage Annuloplasty

A. Mitral Regurgitation

Regurgitation (leakage) of the mitral valve or tricuspid valve can result from many different causes, such as ischemic heart disease, myocardial infarction, acquired or inherited cardiomyopathy, congenital defect, traumatic injury, infectious disease, and various forms of heart disease. Primary heart muscle disease can cause valvular regurgitation through dilation, resulting in expansion of the valvular annulus leading to malcoaptation of the valve leaflets through overstretching, degeneration, or rupture of the papillary muscle apparatus, or through dysfunction or malpositioning of the papillary muscles. This regurgitation can cause heart rhythm abnormalities such as atrial fibrillation, which itself can cause inexorable deterioration in heart muscle function. Such deterioration can be associated with functional impairment, congestive heart failure and significant pain, suffering, lessening of the quality of life, or even premature death.

A less dangerous, minimally invasive procedure, such as percutaneous annuloplasty, permits more patients to undergo mechanical treatment of valvular regurgitation.

B. Percutaneous Cerclage Annuloplasty

Because the risks and complications of surgery are reduced (compared with open-heart surgery), catheter-based heart-valve procedures are suitable for a broader population of patients. Disclosed herein are improved devices and methods for catheter-based valve repair that can be used to repair damaged or malfunctioning cardiac valves, for instance, by re-apposing valve leaflets by percutaneous-cerclage annuloplasty (reconstruction or augmentation of the ring or annulus of a defective cardiac valve). In some instances, percutaneous cerclage annuloplasty is used to deliver circumferential or radial tensioning devices. Examples of some of these procedures are described in detail in WO2004/045378 and US 2005/0216039, which are incorporated herein by reference in their entireties for any purpose whatsoever.

In general, the system used to carry out an annuloplasty procedure can include a guiding catheter (GC), such as a preformed transjugular balloon-tipped guiding catheter which is introduced into the coronary (venous) sinus. A retrograde coronary radiocontrast venogram pressurizes and visualizes the great cardiac vein and septal perforator veins. A high performance guidewire designed for coronary artery recanalization may be steered using a deflectable microcatheter, for example, into the great cardiac vein and thereafter into a basal septal perforator vein.

In general, an annuloplasty procedure also can include using an imaging system to image the internal bodily tissues, organs, structures, cavities, and spaces of the subject being treated. For example, transmitter or receiver coils can be used to facilitate active-device navigation using an imaging system, such as magnetic-resonance imaging (MRI). This imaging can generally be conducted along arbitrary or predetermined planes using various imaging methods based on X-ray technologies, X-ray fluoroscopy, MRI, electromagnetic-positron navigation, video technologies (such as endoscopy, arthroscopy, and the like), ultrasound, and other such technologies. In some embodiments, real-time MRI (rtMRI), intracardiac ultrasound, or electromagnetic guidance is employed. A particularly useful adjunct in cerclage annuloplasty is XFM, in which X-Ray is used with MRI to target myocardial structures, for example to help guide the annuloplasty wire in its trajectory through the structures of the heart. The XFM technique is disclosed, for example, in de Silva et al., *Circulation* 114:2342-2350 (2006). The guiding catheter enables percutaneous access into a subject's body, for example, percutaneous access to the heart, such as a chamber of the heart through an arm, neck, or leg vein. In some embodiments, the guiding catheter is designed for access to the ventricle and/or atrium of the heart. The guiding catheter permits introduction of one or more secondary catheters, including a valve-manipulation catheter or microcatheter or canalization-needle catheter, for example. The secondary catheter (or catheters) is used to treat, affect, or manipulate an organ, tissue, or structure of interest in the subject's body, such as the heart or particular structures within the heart. If the guiding catheter is used for percutaneous (or other) access to the heart, the guiding catheter permits introduction of one or more secondary catheters, such as a valve-manipulation catheter, into the heart while maintaining hemostasis. The secondary catheters may be coaxial or adjacent to each other, or may be introduced from multiple points of access outside the body.

Guiding catheters are available in different shapes to suit the appropriate component of the mitral-valve-repair procedure. For example, guiding catheter shapes can be provided to suit different coronary sinuses with different radii of curvature, to suit different coronary veins, transaortic as well as transseptal access routes, or to suit atria and ventricles of different calibers. All such shapes can be accommodated with appropriate primary, secondary, and tertiary curves. Examples of catheter configurations suitable to perform percutaneous transvascular mitral valve annuloplasty are known in the art and are described in detail in U.S. Patent Publication No. 2005/0216039, which is incorporated by reference herein in its entirety for any purpose whatsoever.

Figure 7A:
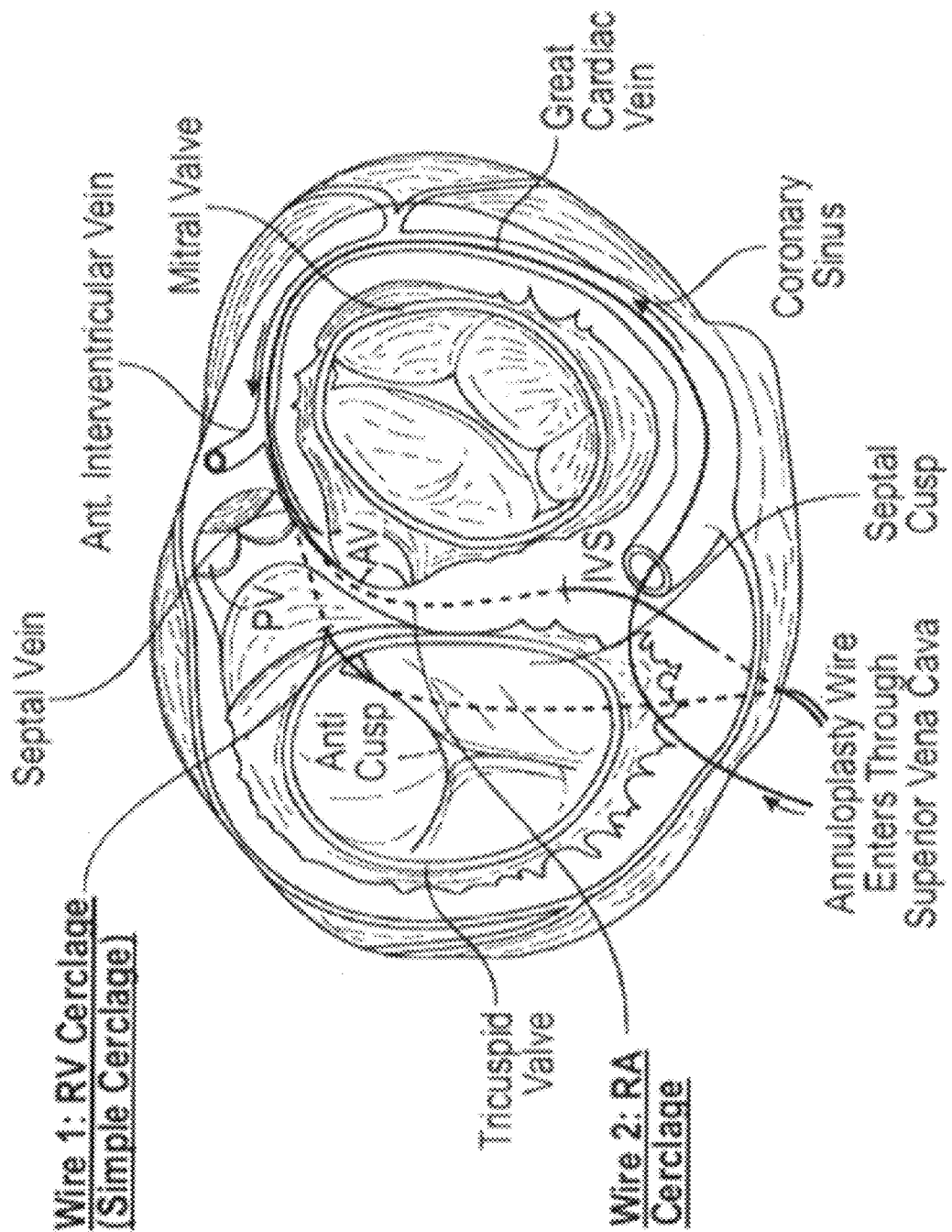
FIG. 7A is a schematic top view of a human heart, taken at the level of the atrioventricular valves, showing in dashed lines two alternative trajectories of the cerclage annuloplasty ligature around the mitral valve.
Figure 7B:
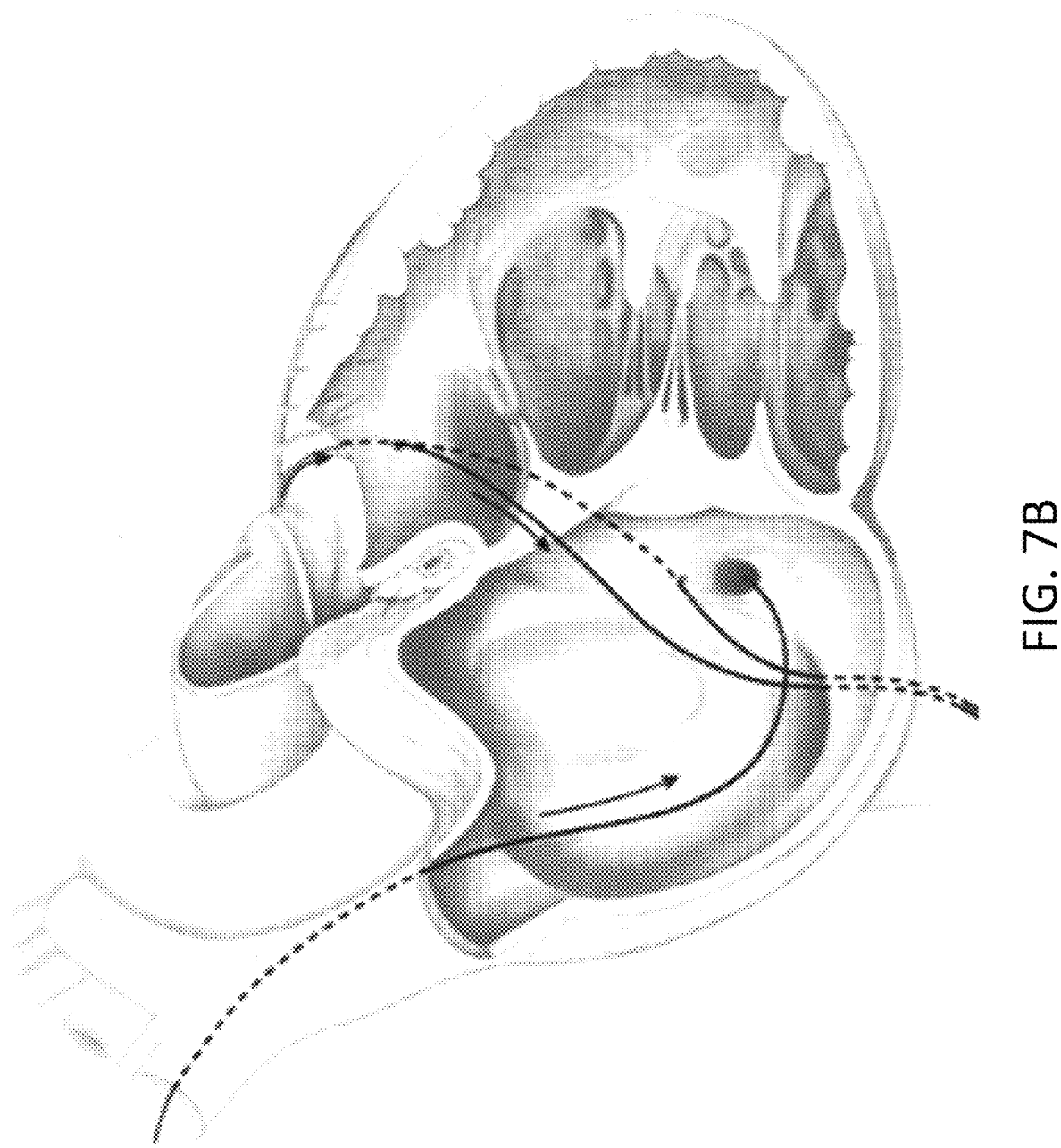
FIG. 7B is a front perspective view of the heart with portions of the myocardial wall broken away to show the cerclage annuloplasty trajectories of FIG. 7A.

Although any available approach to the coronary sinus may be used, a venous approach is preferred, for example through the jugular vein. As yet another example, the guiding catheter can be introduced into a vein, such as the femoral or jugular vein, and guided through the inferior or superior vena cava into the right ventricle of the heart. Two examples of trajectories for cerclage annuloplasty are shown in FIG. 7A and FIG. 7B. The first trajectory (labeled a "simple" or "RV" trajectory) is one in which the annuloplasty wire enters the right atrium through the superior vena cava and is then introduced through the coronary ostium into the coronary sinus. The wire is advanced through the great cardiac vein into a basal blood vessel, such as a basal septal perforator vein. The wire then exits the septal perforator vein through myocardial interstitium into the right ventricle, re-entering the right atrium along the septal tricuspid valve commissure (at the intersection of the anterior cusp and the septal cusp).

The guidewire is then retrieved using, for example, a vascular snare. Any suitable instrument can be used to capture the distal end of the guidewire and withdraw it through the vasculature until it is exposed outside the body. An illustrative preferred and improved snare system to facilitate guidewire retrieval is also described further herein at FIGS. 6A-6C.

Figure 6A:
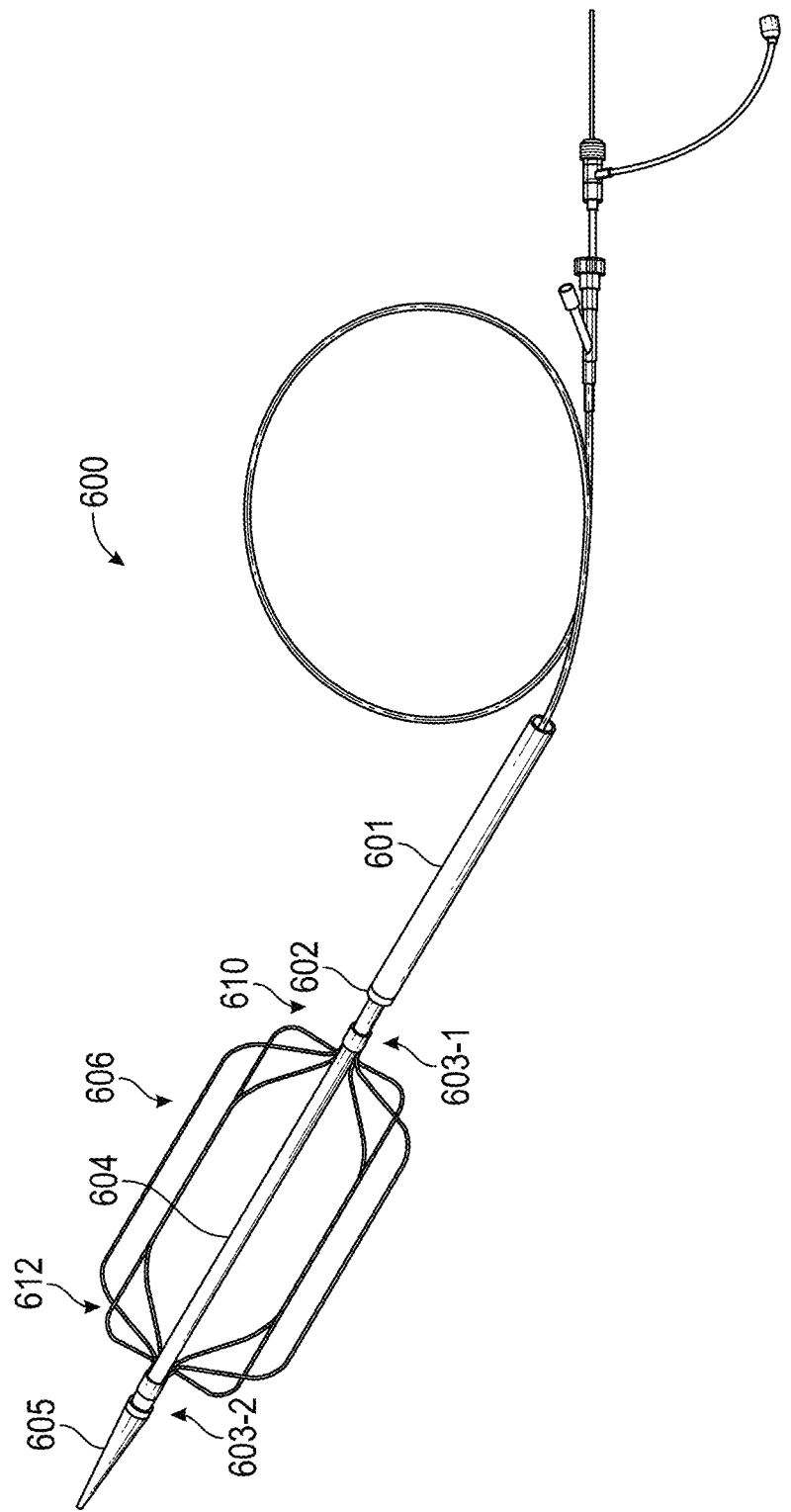
FIG. 6A is a schematic diagram of an embodiment of a snare catheter in accordance with the present disclosure.

For purposes of illustration, and not limitation, FIG. 6A illustrates an exemplary snare catheter 600 for capturing a guidewire, in accordance with the disclosure. As illustrated in FIG. 6A, the snare catheter 600 is defined by an elongate outer tubular member, or sheath, 601 that slidably receives an intermediate tubular member 602 therein along its length. The intermediate tubular member 602, in turn, includes a further elongate inner tubular member 604, such as a hypotube, slidably disposed therein along its length. Relative axial displacement of tubular members 602, 604 causes a wire snare basket 606 (e.g., a collapsible body) to expand or collapse. Snare basket 606 is defined by a plurality of pre-shaped wires, and has a proximal end 610 attached to the distal end of intermediate tubular member 602, and a distal end 612 attached to the distal end of inner tubular member 604. As such, when the ends 612, 610 are pulled away from each other by sliding tubular member 602 distally with respect to tubular member 604, the pre-shaped wires of the basket 606 are elongated and collapse radially inwardly, permitting basket 606 to then be pulled proximally with respect to outer tubular member or sheath 601. Inner tubular member 604 is preferably a metallic member, such as a stainless steel or nickel-titanium alloy hypotube that defines a further lumen along its length that can accommodate a guidewire therethrough. An atraumatic conically tapering atraumatic distal tip 605 is preferably formed over the distal end of the inner tubular member 604 and the distal end portion 612 of the snare basket 606.

Each of the wires comprising the snare basket 606 can be pre-shaped to expand radially outward when the snare basket 106 is in a generally expanded state. For instance, as illustrated in FIG. 6A, each of the pre-shaped wires extends along a plane parallel to a longitudinal axis of the elongate core member 604, and extends radially outward in a direction orthogonal to the elongate core member 604 in the expanded state. When the snare basket 606 is in the expanded state, the distance with which each wire extends radially outward from the elongate core member 604 is uniform and defined by the geometric shape of the pre-shaped wires. Further axial displacement of the distal end of the elongate intermediate tubular member 602 toward the distal end of the elongate core member causes the geometric shape of snare basket 606 to change, via a change in the shape of each respective pre-shaped wire. For instance, displacement of intermediate tubular member 602 toward tip 605 causes each of the plurality of pre-shaped wires to curve in a direction orthogonal to the plane parallel to the elongate core member (e.g., to curve radially outward). Conversely, displacement of intermediate tubular member 602 in a direction opposite of tip 605 causes each of the plurality of pre-shaped wires to contract radially inward toward elongate core member 604.

Thus, the snare catheter 600 can include elongate outer tubular member, or sheath, that slidably receives an intermediate tubular member therein along its length. The intermediate tubular member, in turn, includes a further elongate inner tubular member, such as a hypotube, slidably disposed therein along its length. Relative axial displacement of tubular members causes the snare basket filaments to expand or collapse. The snare "basket" as illustrated is formed from pre-shaped wires as illustrated in FIG. 6A. As described with regard to FIG. 6A, each of the pre-shaped wires of the snare basket has a proximal end attached to the distal end of intermediate tubular member, and a distal end attached to distal end of the inner tubular member. As such, when the ends of the inner and intermediate tubular members are pulled away from each other by relative sliding linear displacement, the pre-shaped wires of the basket are elongated and collapse radially inwardly, permitting the basket to then be pulled proximally with respect to the outer tubular member or sheath and pulled into the distal end of the sheath. The inner tubular member is preferably a metallic member, such as a stainless steel or nickel-titanium alloy hypotube that defines a further lumen along its length that can accommodate a guidewire therethrough. An atraumatic conically tapering atraumatic distal tip is preferably formed over the distal end of the inner tubular member (FIG. 6A) and the distal end portion of the snare basket. The distal tip can be overmolded over the aforementioned components, or it may be pre-formed and adhered to the system, such as with UV activated adhesive and the like.

Preferably, the distal tip defines a distal opening therethrough to permit a guidewire to pass therethrough after traversing the lumen defined inside inner tubular member. The distal tip of the device 600 may be made from polymeric material such as PEBAX polymer, 35D Nylon material, or any other suitable atraumatic material or other material, and may be provided with a lubricious hydrophobic or hydrophilic coating as described elsewhere herein (e.g., PVP). Having the distal tip made from atraumatic material facilitates passage of snare catheter 600 through tortuous vasculature including sharp turns to arrive in the right ventricle proximate the pulmonary valve to intercept the guidewire passing through the septum wall after passing through the wall of the coronary sinus, or passing the guidewire between the target septal perforator vein and the Right Ventricular Outflow Tract (RVOT). The inner tubular member may traverse substantially the entire length of the distal tip of the device 600, but preferably stops short of the distal end of tip to permit the tip to flex as it passes through vasculature.

Figure 6B:
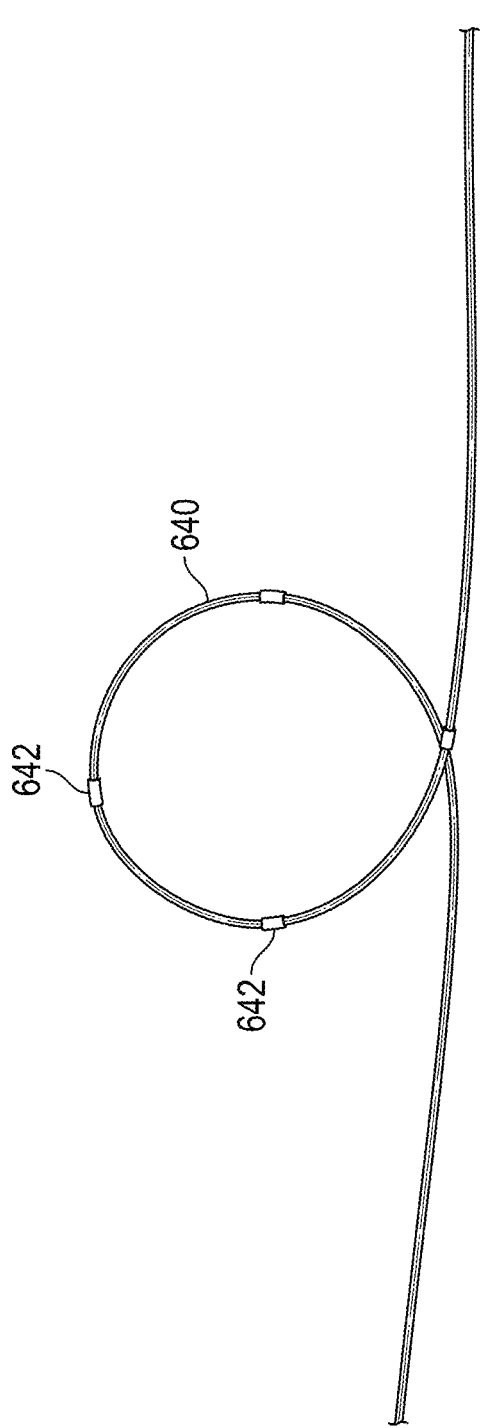
FIGS. 6B-6C are illustrations of target wires for use with the snare catheter of FIG. 6A.
Figure 6C:
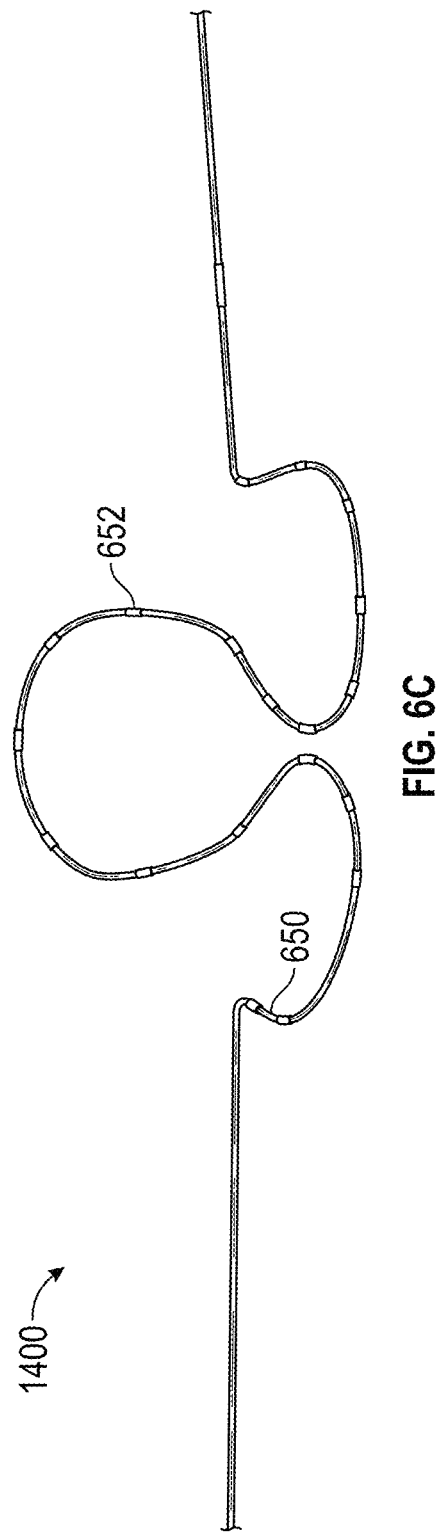

Marker bands are preferably formed on the distal end portions of the inner, intermediate, and outer tubular members respectively. Also, as illustrated in FIGS. 6B-6C, if desired, an inner target filament, or wire 640, 650, may be provided having a two dimensional (FIG. 6B) or three dimensional (FIG. 6C) looped geometry to facilitate capture of the distal end of a guidewire passed through the wall of the septum into the region of the right ventricle near the pulmonary valve. Each target wire 640, 650 has a proximal end attached to the distal end of the intermediate tubular member and a distal end attached to the distal end of the inner tubular member of catheter 600. The target wire 640, 650 further defines one or more wire loops therein laying in one or more planes. When the basket is elongated by virtue of longitudinally displacing the distal ends of relative longitudinal motion of the intermediate and inner tubular members, the target wire 640, 650 similarly lengthens and the loop(s) collapse.

FIG. 6B illustrates a target wire 640 having a single loop. In either case, the wire 640 essentially lies in a single plane. FIG. 6C illustrates a variation of the wire 650 wherein three loop-like undulations are provided that mimic the loop of the wire 640 in FIG. 6B, but are formed in more than one plane using a single filament. As depicted, two of the undulations lay in the same plane, and are separated by a third undulation that is in a second plane that is offset by about ninety degrees with respect to the plane of the other two undulations. The wires 640, 650 can be made from a variety of materials, such as nitinol or other material, and may be provided with a plurality of marker bands 642, 652. In one embodiment, wires 640, 650 are formed from a composite wire, such as DFT® wire, available from Fort Wayne metals.

After snaring the guidewire and removing the distal end thereof from the patient, the implant (e.g., 400) is exchanged for the guidewire by crimping the implant onto the proximal end of the guidewire via crimp (e.g., 570). The implant (e.g., 400) can then be advanced along the path of the guidewire as the guidewire is withdrawn from the patient until the distal end (e.g., 249) of the protection device or bridge (e.g., 420) is proximate the septum wall and the bridge is traversing the LCx artery. The location of the jeopardized coronary artery is confirmed, for example, by radiocontrast angiography. In an alternative approach, coronary veins are entered in the opposite direction from the right atrium or right ventricle under imaging guidance into a branch of the coronary sinus.

An alternative or "complex" right atrial cerclage trajectory shown in FIGS. 7A and 7B extends further posterior through the basal septal myocardium into the right atrium near the coronary sinus. The wire traverses deep tissue of the septum moving in a posterior direction and exits above the opening of the coronary sinus. The plane of the resulting cerclage annuloplasty is shown in FIG. 8C to be related to and in the plane of the coronary sinus 860 such that annuloplasty remains uniquely feasible even if the coronary sinus is remote from the mitral valve annuloplasty. As the figure indicates, the plane of cerclage 860 enhances mitral valve coaptation, even when the coronary sinus is geometrically remote from the mitral valve annulus, because it is "tilted" toward the left ventricular outflow tract. The illustrated angle $\alpha$ between the cerclage plane 860 and the plane of the mitral valve annulus 862 is therefore advantageous. Moreover, the illustrated trajectories of the cerclage annuloplasty induces reciprocal mitral valve coaptation and left ventricular outflow tract relaxation during ventricular systole.

The guide wire is dimensioned to operate with the guiding catheter and is usually longer than the guiding catheter. For example, a guide wire of about 100 to about 250 centimeters in length and about 0.1 to about 2 mm in diameter can be used with the guiding catheter described above. If a secondary catheter, such as a tension delivery catheter, is intended for use with the guiding catheter, that secondary catheter also is dimensioned to operate with the guiding catheter and is usually longer than the guiding catheter.

The guiding catheter can be made of any suitable material or combination of materials that provide both the strength and flexibility suitable to resist collapse by external forces, such as forces imposed during bending or twisting. Exemplary materials include, but are not limited to: polymers, such as polyethylene or polyurethane; carbon fiber; ceramic; or metals, such as nitinol, platinum, titanium, tantalum, tungsten, stainless steel, copper, gold, cobalt-chromium alloy, or nickel. The guiding catheter optionally can be composed of or reinforced with fibers of metal, carbon fiber, glass, fiberglass, a rigid polymer, or other high-strength material. In particular embodiments, the guiding catheter material is compatible with MRI, for example, braided nitinol, platinum, tungsten, gold, or carbon fiber. Additionally, the exterior surfaces of the guiding catheter can be coated with a hydrophobic material or substance, such as Teflon® or other lubricous material, such as a hydrophilic material (e.g., PVP) that aids with the insertion of the guiding catheter into the body of the subject and/or aids in the movement of the guiding catheter through the subject's body.

Additionally, the guiding catheter can include a deflectable tip, such as a simple deflectable tip having a single degree of axial freedom. Exemplary (non-limiting) fixed-fulcrum and moveable-fulcrum-deflectable-tip catheters are commercially available, such as the deflectable-tip catheters described in U.S. Pat. Nos. 5,397,321; 5,487,757; 5,944,689; 5,928,191; 6,074,351; 6,198,974; and 6,346,099, each of which being incorporated by reference herein in its entirety for any purpose whatsoever. Thus, any suitable fixed-fulcrum or moveable-fulcrum deflectable-tip catheter can be adapted for use as a guiding catheter disclosed herein. The guiding catheter also can include structures or mechanisms for aiding in the rotation of the catheter about its longitudinal axis.

The guiding catheter can include a guide collar, handgrip, handle, and other structures or devices at its proximal end that aid in operation of the guiding catheter. Various control mechanisms, including electrical, optical, or mechanical control mechanisms, can be attached to the catheter via a guide collar. For example, a guide wire can be included as a mechanical control mechanism. The guide collar can include additional operational features, such as a grip for aiding manual control of the guiding catheter, markers indicating the orientation of the guiding catheter lumen or subdivided lumens, markers to gauge the depth of guiding catheter advancement, instruments to measure guiding catheter operation or physiological signs of the subject (for example, a temperature gauge or pressure monitor), or an injector control mechanism coupled to the guiding catheter lumen for delivering a small, precise volume of injectate. In some embodiments, the guide collar contains instrumentation electrically coupled to metallic braiding within the guiding catheter, thus allowing the guiding catheter to simultaneously be used as a receiver coil for MRI.

A guide wire used with the system for guiding the guiding catheter into and through a subject's body can be composed of any suitable material, or combination of materials, including the materials described above in relation to the guiding catheter. Exemplary (non-limiting) guide wires are composed of material having the strength and flexibility suitable for use with the device, such as a strand of metal (for example, surgical stainless steel, nitinol, platinum, titanium, tungsten, copper, or nickel), carbon fiber, or a polymer, such as braided nylon. Particular (non-limiting) guide wires are composed of a strand of Nitinol or other flexible, kink-resistant material. The guiding catheter or guide wire can include an image-enhancing feature, structure, material, or apparatus, such as a radiopaque marker (for example, a platinum or tantalum band around the circumference of the guide wire) adjacent its distal end. As another example, the guide wire can include etchings or notches, or be coated with a sonoreflective material to enhance images obtained via intravascular, intracardiac, transesophogeal, or other ultrasound-imaging methods. As another example, the guide wire can be coated with a T1-shortening or T2-shortening agent to facilitate passive visualization using MRI. As yet another example, a fiber-optic secondary catheter can be inserted into and through a secondary-catheter lumen of the guiding catheter to assist in visualizing the position of the guide wire within the subject as a guide wire is deployed through the distal guide-wire lumen port. In some embodiments, the guide wire and/or guiding catheter includes a structure, apparatus, or device at its distal tip useful for penetrating tissue, such as myocardial skeleton, muscle, or connective tissue. For example, the distal tip of the guide wire can be sharpened to a point for puncturing through tissue, or a secondary catheter having a coring mechanism or forceps at its distal tip can be used in conjunction with the guiding catheter. In alternative embodiments, the guide wire can deliver radiofrequency or laser ablative energy to assist with traversal of tissue. However, in alternative embodiments, the distal end of the guide wire is bent to provide a J-shaped or a pigtail-shaped tip to protect against perforation of tissue by the guide wire during manipulation. In still other alternative embodiments, the guide wire itself has a deflectable tip to facilitate traversal of tissue irrespective of natural tissue planes. One or more secondary catheters can be deployed within the lumen of the guiding catheter. Like the guiding catheter, each secondary catheter has a proximal end and a distal end; however, not all secondary catheters have a lumen. For example, non-lumen secondary catheters can include various probes, such as temperature probes, radiofrequency or cryogenic ablation probes, or solid needles.

An exemplary non-limiting secondary catheter is a canalization needle catheter, which can be deployed through the guiding catheter and into a chamber of the heart to place cerclage annuloplasty ligature through the coronary sinus around the mitral valve. A canalization-needle catheter is a type of secondary catheter that can be used to apply a suture to a bodily tissue, organ, or structure of interest.

C. Application of Tension

Tension is applied via the annuloplasty cerclage through the sheath material (e.g., 450), which is preferably a hollow braided suture material as described above. Tension can be applied to both ends of the sheath (e.g., 450) as they are externalized at the point of vascular access in concert with a lock delivery catheter as described in further detail below that directs both ends of the suture through a lock mounted at the end of the lock delivery catheter.

Figure 19:
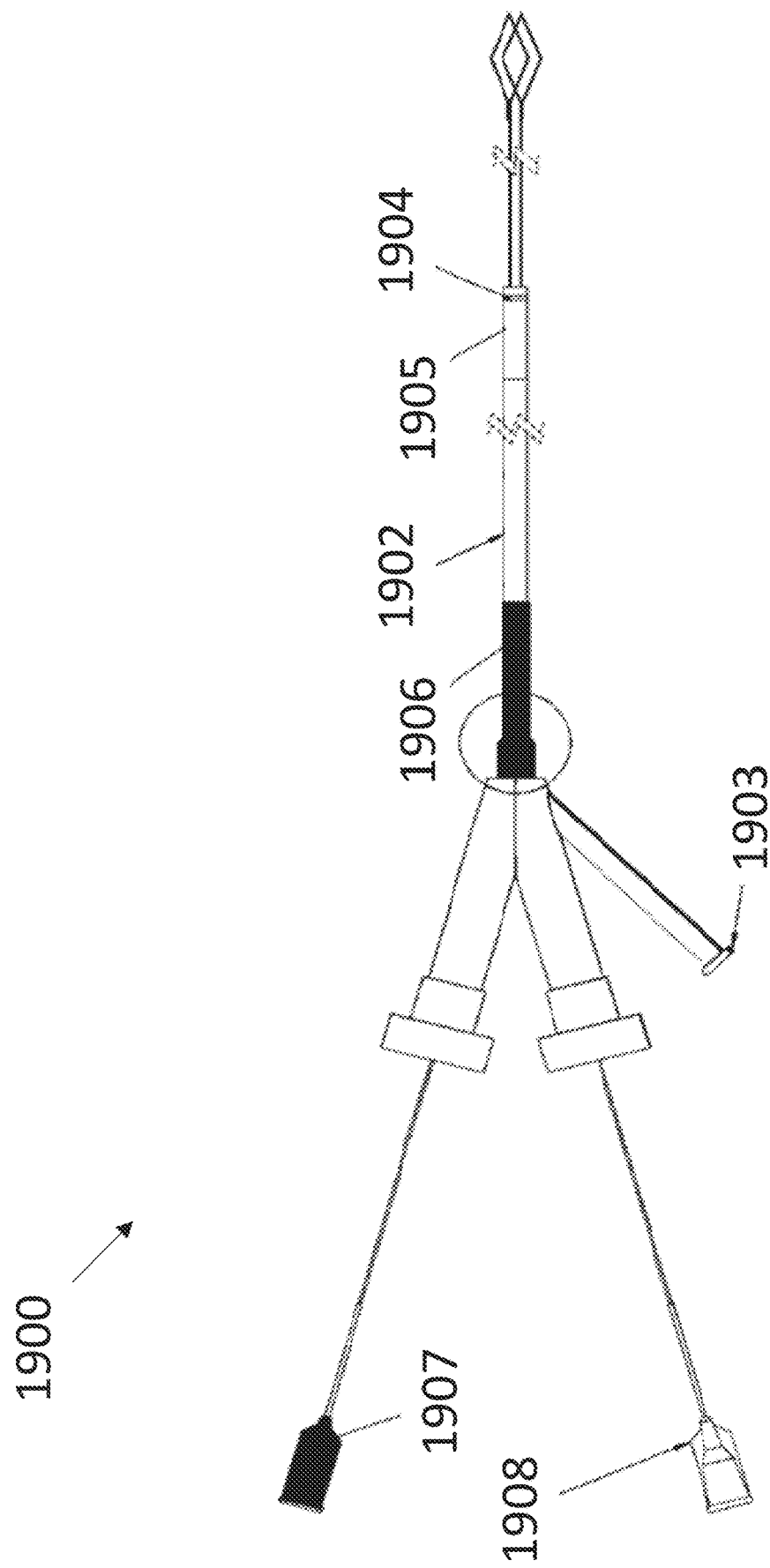
FIG. 19 illustrates a straightening, or disentangling catheter in accordance with the present disclosure.

In some procedures, it is possible for the ends of the tether 450 (the ends of the implant that are externalized) to become twisted about each other. This can complicate the delivery of the lock over the ends of the tether. To help ensure against this, after the ends of the tether 450 are externalized (e.g, via the jugular or other access point), a straightening, or disentangling catheter 1900 as set forth in FIG. 19 can be used to separate the ends of the tether so that they are parallel and not twisted, thereby greatly simplifying delivery of the lock over the ends of the tether 450 into the heart. Catheter 1900 includes a plurality of snares 1901. In use, each end of tether 450 is fed into one of the snares which terminates in a distal loop. Each snare can have a body made, for example from stainless steel wire or hypotube. The proximal end of each snare is attached to a respective snare hub 1907, 1908. Snares 1901 are slidably disposed through a dual lumen shaft 1902, made, for example, from Pebax material. A double hemostasis valve with gaskets 1903 is also provided at a proximal end of shaft 1902, and one or more marker bands 1904 (e.g., of platinum-iridium), to help visualize the location of the distal end of catheter 1900, are provided (held in place by a heat shrink cover 1905 made of Pebax). A strain relief 1906 is also provided that is heat shrunk about the proximal end of shaft 1902. Various components can be held in place by suitable adhesives. After the tethers 450 are loaded into the catheter, the hubs 1907, 1908 can be pulled proximally to advance dual lumen shaft 1902 into the body and down to the location in the heart where the lock is to be delivered. The operator can visualize the procedure under fluoroscopy, and can visually detect locations where the tethers are twisted as long as the tethers 450 are radiopaque or include a radiopaque filament, such as a platinum wire described elsewhere herein.

Once the tethers 450 are externalized and untangled, tension can be applied under imaging guidance to the tethers through the lock at a distal end of the lock delivery catheter until the desired degree of mitral annular circumferential reduction is accomplished, or until the mitral valve regurgitation is reduced, or until other deleterious endpoints are achieved such as mitral valve inflow obstruction. Tension in the sheath (e.g., 450) can then be secured by locking the lock of the lock delivery catheter such as that described in copending U.S. patent application Ser. No. 14/074,517, filed Nov. 7, 2013, or the lock delivery catheter described below. Alternatively, a knot may be tied and pushed through a guiding catheter. The lock or knot, as desired, can be located at the right atrium or right ventricle where the two cerclage trajectories cross, or at the point of vascular access, or in between the two. Tension can thus be delivered, if desired, by counterpressure against the fixation device, for example, applied through a delivery catheter. Before fixation, tension can be released or reduced, for example, to reposition the protection device or to achieve a lower degree of mitral annular circumferential reduction.

As tension is applied, valvular regurgitation is preferably assessed repeatedly and non-invasively by an appropriate imaging technique. Such imaging techniques include X-ray angiography, electromagnetic position detection, MRI, external or intracavitary or intravascular ultrasound, X-ray computed tomography, pressure transducers in an affected chamber such as the left atrium or the pulmonary vein or the pulmonary artery, or a "fusion" or combination of any of the above. After the valvular regurgitation has been reduced (or even eliminated) and a desired tension is achieved, the tension is fixed using a lock or knot delivery system as mentioned above, and the excess sheath material proximal to the lock or knot can be cut and removed in any desired manner. In accordance with one aspect of the disclosure a cutting instrument can be used as described further below with reference to FIGS. 14A-14I herein.

If the resulting circumferential sheath (e.g., 450) is knotted to form a closed loop, the sheath 450 essentially becomes a cerclage suture. Without further elaboration, it is believed that one skilled in the art can, using this description, utilize the present discoveries to their fullest extent.

The use of the implant with protective device (e.g., 420) has been disclosed for use in a cerclage annuloplasty technique. However, the disclosed implants can be used with any other annuloplasty device that extends even partially through the coronary sinus in a region that crosses an underlying coronary artery. For example, the protective device (e.g., 420) can be used to protect against compression of coronary arteries with any coronary sinus annuloplasty device, such as the coronary sinus device in U.S. Pat. No. 7,090,695 or the inflatable coronary sinus device shown in U.S. patent Ser. No. 10/787,574 (U.S. Patent Publication No. 2004/0254600). Although these devices are designed for endovascular delivery, the protection device disclosed herein can also be used with annuloplasty devices that are implanted using an open-chest surgical repair instead of a catheter based approach. The problem of coronary artery compression is also encountered with these devices, and the protective device disclosed herein may be used to avoid that problem. Hence the presently disclosed embodiments are not limited to a protective device for use with cerclage annuloplasty, nor is it limited to use of the device with catheter based delivery techniques.

When used with a coronary sinus annuloplasty implant of any kind, the protective device (e.g., 420) can be provided as an integral part of the implant (e.g. 400) or as a separate device suitable for placement between the implant and an underlying coronary artery to be protected. When provided as an integral part of the implant, the implant is positioned in the coronary sinus so that the arch of the support extends over the underlying coronary artery. In alternative embodiments the protection device can be provided as a separate device that is advanced through a catheter system until it is positioned over the coronary artery to be protected.

A mitral cerclage annuloplasty device, as described herein, can push heart tissue radially inwardly and create a retaining structure projecting into the heart near the native mitral valve region to allow implantation and securement of a prosthetic transcatheter mitral valve (TMV). As used herein, the terms prosthetic mitral valve, transcatheter mitral valve, TMV, prosthetic mitral device, prosthetic mitral implant, and the like, include any prosthetic device implantable within or adjacent to the native mitral valve region, including valved devices and as well as devices that do not include a valve component (e.g., frames, stents, rings, fasteners, tethers, portions of a valved device, etc.). In some embodiments, cerclage annuloplasty can create an internal ridge, landing zone (as described herein above), fixation plane, etc. (referred to herein generally as a "retaining structure") for a TMV to be secured.

The TMV secured to the retaining structure within the heart can comprise a radially compressible and radially expandable prosthetic device that is delivered into the heart in a radially compressed state using a transcatheter, transvascular delivery approach, for example. Once inside the heart, the TMV can expand, either using applied expansion force (e.g., an inflatable balloon) or using intrinsic self-expanding materials (e.g., nitinol) that cause the TMV to self-expand upon removal of a compressive force applied during delivery. Upon expansion, the TMV can become secured to the retaining structure created by the mitral cerclage annuloplasty device to inhibit the TMV from migrating out of position within the heart. For example, the TMV can comprise a tubular frame that expands around both sides of the retaining structure and/or clamps onto the retaining structure.

When expanded, the implanted TMV can apply a radially outward force on the heart tissue. This radially outward force can undesirably compress blood vessels in the heart tissue and cause constriction and reduced blood flow. At the same time, the radially inward force applied by the mitral cerclage annuloplasty device can also undesirably compress blood vessels in the heart tissue from the outside. This dual compression on the cardiac blood vessels can exacerbate the risk of ischemia, heart attack, and other complications. Of particular concern are the circumflex coronary artery and its marginal branches near the great cardiac vein, which can between the implanted TMV and the surrounding mitral cerclage annuloplasty device. Accordingly, protection devices as disclosed herein can help protect such blood vessels from compression from both the outside-in (via the mitral cerclage annuloplasty device) and from inside-out (via the TMV).

Figure 9:
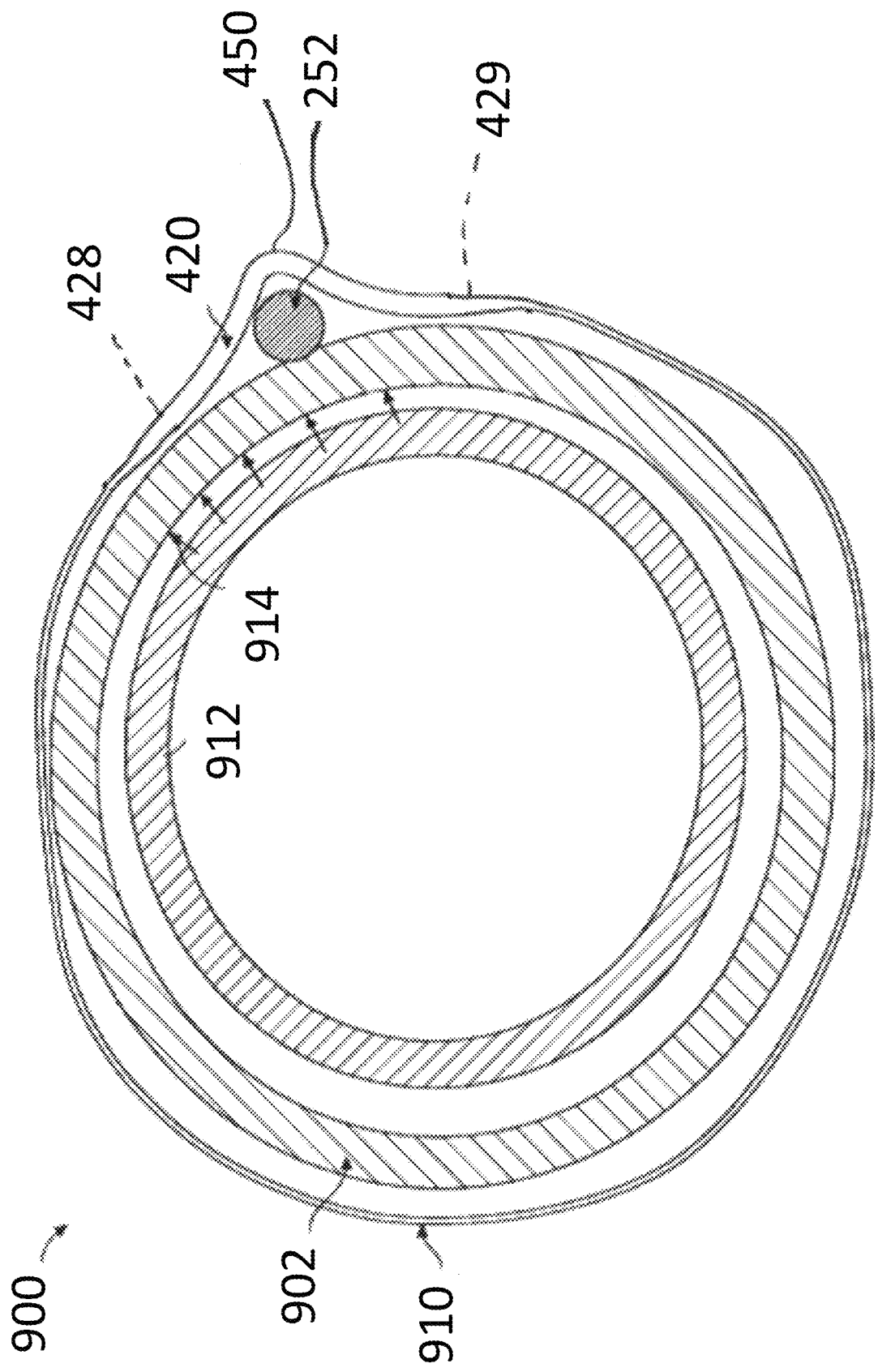
FIG. 9 is a schematic cross-sectional view of the mitral valve region of a heart wherein a prosthetic heart valve is positioned within the mitral valve region and applies an outward expansion force and a mitral cerclage implant in accordance with the disclosure is positioned around the mitral valve region and applies an inward force, and a coronary protection device in accordance with the disclosure is positioned along the mitral cerclage device to protect the coronary artery from being compressed.

FIG. 9 is a schematic cross-sectional view of the mitral valve region of a heart showing an exemplary implant system 900 that includes an implanted TMV 912 positioned within the heart wall 902 and a mitral cerclage annuloplasty device 910 positioned around the heart wall. The device 910 includes an arched protection device 420 spanning over a coronary artery 252 to protect the artery from compression applied by both the device 910 from the outside and outward expansion force 914 applied on the inside of the heart wall 902 by the TMV 912. The exemplary protection device 420 includes an arched portion extending between two flattened, generally coplanar proximal and distal segments 428, 429. The bridge, or protective device 420 can have any combination of features and dimensions described herein with regard to other exemplary protection devices.

Figure 10:
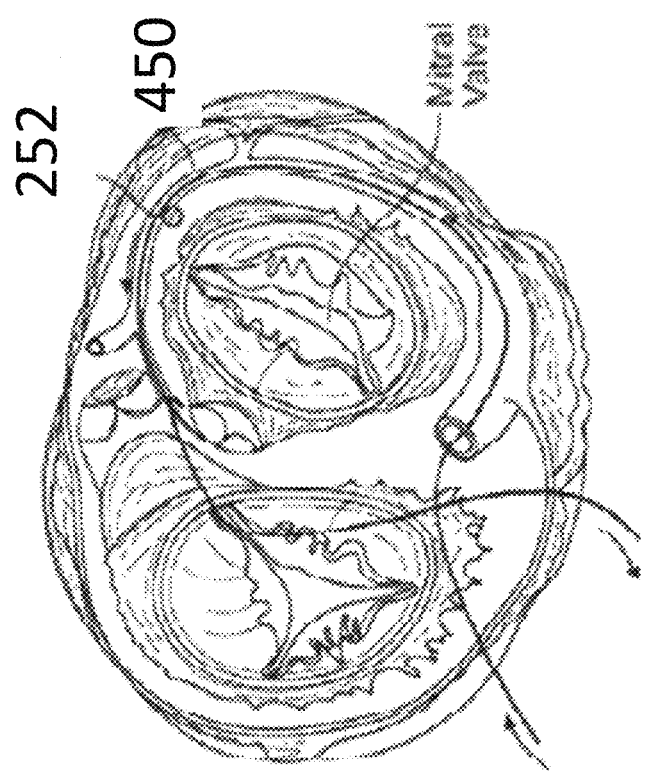
FIG. 10 is a cross-sectional view of a heart with a mitral cerclage device being delivered through the coronary sinus and around the mitral valve.

FIG. 10 shows a tensioning suture (e.g., 450) extending through the coronary sinus 250 partially around the mitral valve without the inclusion of the disclosed protection device. Consequently, the circumflex coronary artery 252 is entrapped under the tensioning suture as the coronary sinus overlaps the artery, applying unwanted compression on the artery. When a TMV is also implanted within the mitral valve, it can apply additional inside-out compression force on the artery 252. Without the protection device, the artery 252 can collapse and/or be pinched by the opposing forces.

FIGS. 11A and 11B illustrate aspects of a lock delivery system in accordance with the disclosure. For purposes of illustration, and not limitation, the lock delivery system 1110 includes a delivery catheter having a proximal end and a distal end with a lock attached to its distal end. More specifically, lock delivery system 1110 includes an outer tubular member having an inner tubular member disposed therein.

The inner tubular member can be made from any suitable material, preferably a polymeric material such as PEEK. The outer tubular member is preferably provided as a braided catheter material, such as a polymeric co-extrusion including a braided layer. The threaded connection between fastener portion and inner tubular member permits attachment of the two components to each other to thereby permit remote opening and closing of the lock, as well as permitting the lock to be removed and retrieved, if desired, even after full deployment of the lock. As depicted, this embodiment of a lock delivery system includes a proximal housing connected to a hemostatic delivery device hub with flush port connected to a distal outer tubular member that is connected at its distal end to a housing for the lock body. The housing is configured and adapted to maintain the lock body in rotational registration with respect to the lock delivery system, such that turning the delivery system will cause the lock body to turn with it. Device 1110 further includes a rotatable release knob, or lever, 1154. When in a locked position, a tether routed around the distal end of device 1110 is held fast and locked in place via frictional forces, holding the lock in place against the distal end of the device 1110. When the knob or lever 1154 is rotated by a predetermined amount about its rotation axis within the housing, such as 90 degrees, the tether is movable, and tension can be applied to the tether, if desired, or the tether can be withdrawn from the device.

The illustrated embodiment of the lock delivery system further includes one or more additional spring loaded push buttons, or tension controls, for controlling grasping of either end of the outer sheath (e.g., 450) of the implant. In a default position where the button is not depressed, the tether passing through a capture mechanism associated with the push button will grip the implant tether (e.g., sheath 450 described elsewhere herein) and maintain it under tension. When each push button (individually and/or both) is pressed down, it will allow for release of one or both tethers associated with the implant. It will be appreciated that both ends of the tether can be routed through the same control button for purposes of simplicity.

Figure 12A:
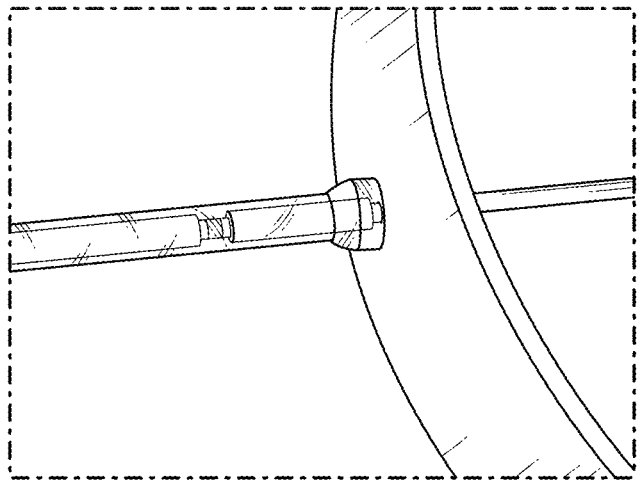
FIGS. 12A-12D illustrate aspects of a first embodiment of a limb of adjustable length for attachment to a lock and lock delivery system in accordance with the present disclosure.
Figure 12B:
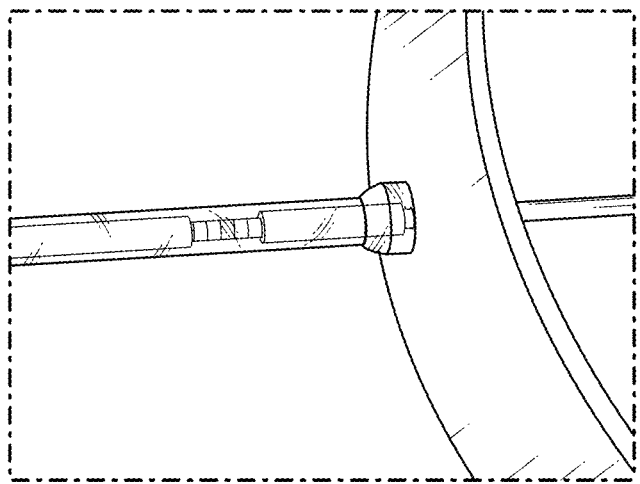
Figure 12C:
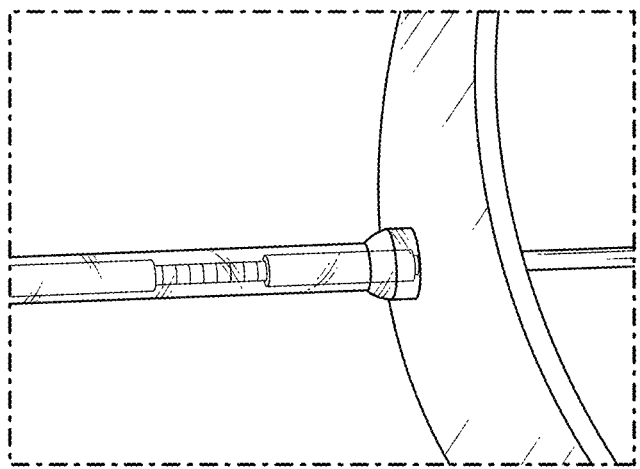
Figure 12D:
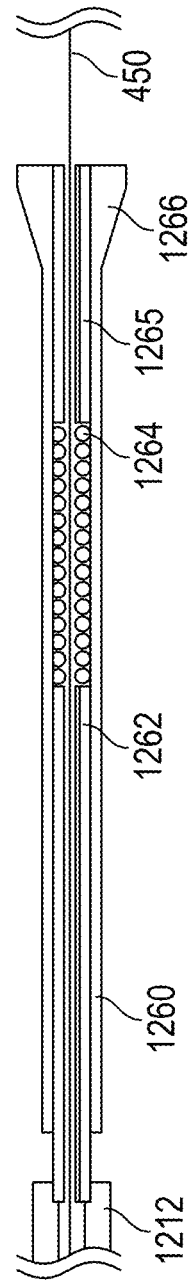

As set forth in FIGS. 12A-12D, a further embodiment of a limb for attachment to a lock body in accordance with the present disclosure with an adjustable length is presented. FIG. 12D presents a cross sectional view of an implant (e.g., tether 450) passing through a limb of adjustable length that is attached at a proximal end to lock body 1212. The limb includes an outer tubular member 1260 that can include a bell-shaped atraumatic distal tip 1266, preferably integral thereto, for abutting a septal wall. Outer tubular member 1260 is also preferably attached to a distal section 1265 of an inner tubular member that extends from the distal tip 1266 along a proximal direction to a location where a compression spring 1264 is disposed underneath the outer tubular member 1260. The distal end of spring abuts the proximal end of the distal section 1265. A proximal inner tubular member 1262 is slidably disposed within a proximal section of tubular member 1260. A proximal end of proximal inner tubular member 1262 is attached to the lock body 1212, and a distal end of the proximal inner tubular member 1262 abuts a proximal end of the spring 1264. Thus, spring 1264 is contained in a compartment defined by an inner cylindrical surface of outer tubular member 1260 the proximal end of tubular member 1265 and the distal end of tubular member 1262. Spring 1264 defines and surrounds an interior lumen along its length that permits the passage of sheath 450.

In operation, when the distal tip 1266 abuts the septal wall, the overall length of the limb can be reduced by pushing distally on the lock body, which in turn pushes against the proximal inner tubular member 1262 that in turn slides distally within (and with respect to) the outer tubular member 1260, compressing the spring 1264. The proximal portion of inner tubular member 1262 that is not surrounded by outer tubular member 1260 defines the amount that the spring can compress, which can be arranged as desired. The spring can be configured to compress completely, or only partially. It will be appreciated that FIG. 12D is a representative cross section, and is not intended to be to dimensional scale. To further illustrate this embodiment, FIG. 12A illustrates the limb in a lengthened state wherein the spring 1264 is not compressed. FIG. 12B shows the spring partially compressed, and FIG. 12C shows the spring fully compressed.

Figure 12E:
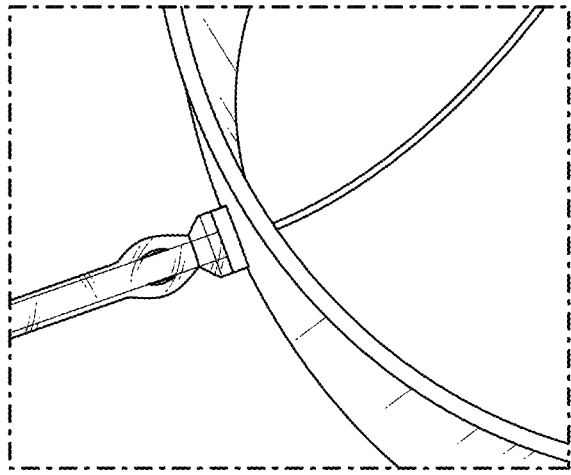
FIGS. 12E-12H illustrate aspects of a first embodiment of a limb of adjustable length for attachment to a lock and lock delivery system in accordance with the present disclosure.
Figure 12F:
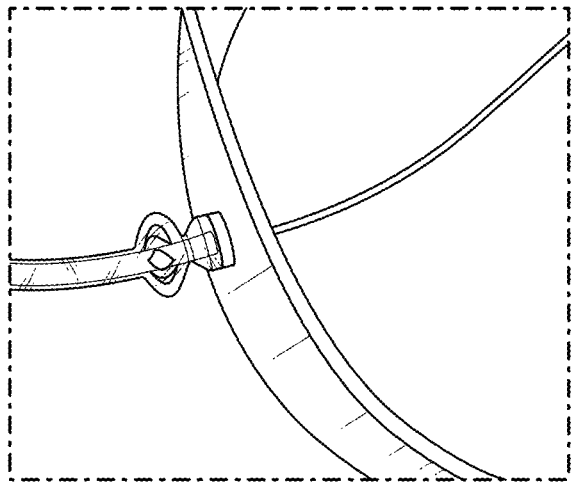
Figure 12G:
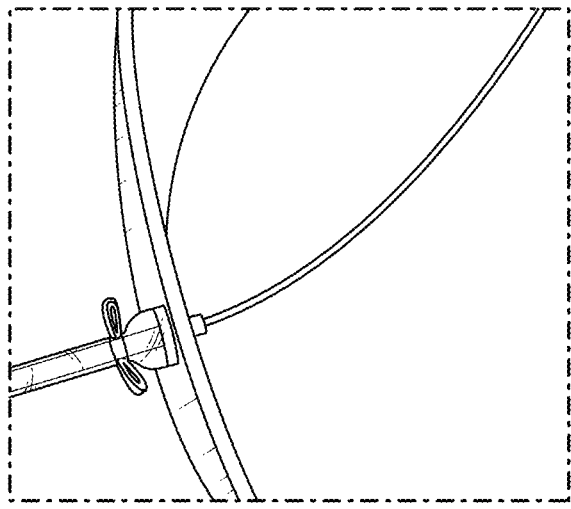
Figure 12H:
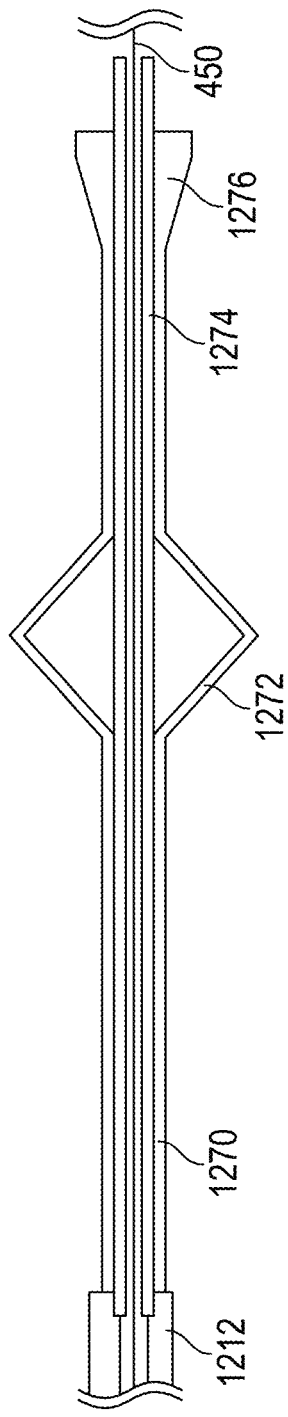

As set forth in FIGS. 12E-12H, a further embodiment of a limb with an adjustable length is presented. FIG. 12H presents a cross sectional view (not to dimensional scale) of an implant (e.g., tether 450) passing through a limb of adjustable length that is attached at a proximal end to lock body 1212. The limb includes an outer tubular member 1270 that can include a bell-shaped atraumatic distal tip 1276, preferably integral thereto, for abutting a septal wall. Outer tubular member 1270 includes a distal section and a proximal section separated by a compression section 1272.

Compression section 1272 is defined by a plurality of parallel cuts passing from an outer surface of the outer tubular member to an inner surface of the outer tubular member. The cuts are arranged parallel to a central longitudinal axis of the limb, and (preferably uniformly) distributed circumferentially around the circumference of the outer tubular member 1270. The cuts are preferably of uniform length and lengthwise alignment (but this may be varied, as desired). Any suitable number of such cuts may be made around the tubular member 1270. The proximal section of the outer tubular member may be directly attached to lock 1212. As illustrated, the proximal section of tubular member 1270 is attached to a proximal section of an inner tubular member 1274, wherein the proximal end of tubular member 1274 is received within and attached to lock 1212. Tubular member 1274 is not attached to the section of tubular member 1270 that is located distally of the compression section 1272 to permit relative sliding contact between the tubular members 1270, 1274 in that section. In operation, and with reference to FIGS. 12E-12G, FIG. 12E illustrates the limb at full length, wherein the legs defined between the cuts in the compression section 1272 are beginning to separate from each other and bow radially outwardly as the outer tubular member 1270 shortens. FIG. 12F shows the legs bowed further outwardly as tubular member 1270 continues to shorten, and FIG. 12G shows member 1270 at its shortest length, wherein the resilient legs of the "spring" or compression section 1272 are fully compressed, forming a petal arrangement around the circumference of the limb.

Figure 13C:
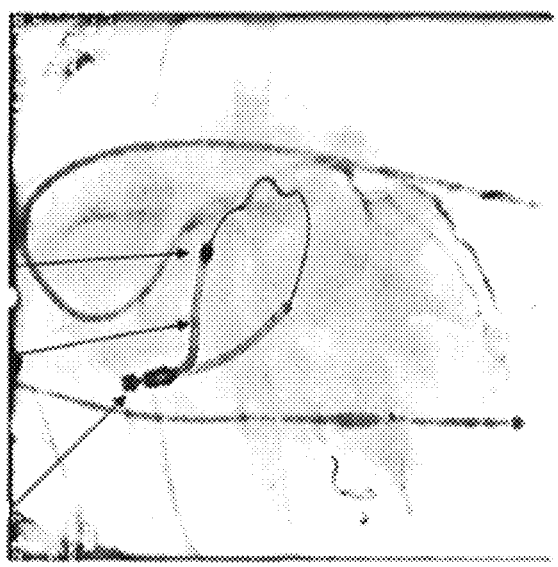
FIGS. 13A-13C illustrate deployment of the lock on the exemplary cerclage device in an animal.
Figure 13B:
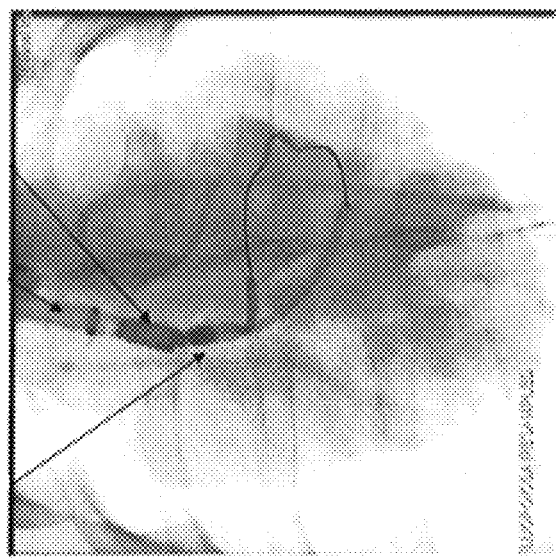
Figure 13A:
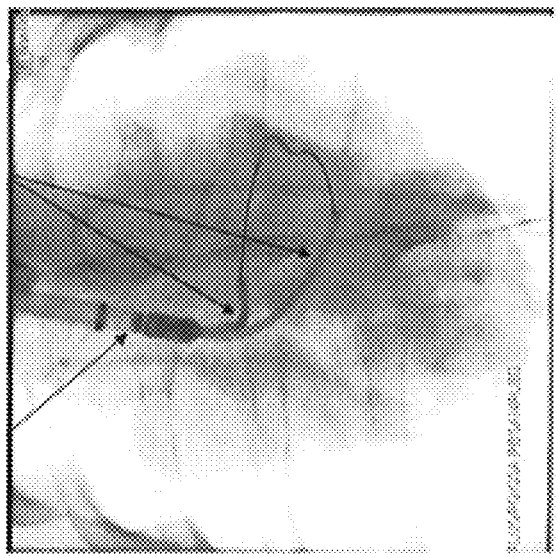

FIGS. 13A-3C illustrate deployment of the illustrated lock on the exemplary cerclage device in an animal. FIG. 13A illustrates an image of the lock delivery catheter 1110 delivered to a location where tension may be imposed on the sutures (e.g., 450) by pulling them proximally through the lock delivery system and locking the lock to maintain the tension. In FIG. 13B, the outer tubular member is released from the outer lock portion and withdrawn. In FIG. 13C, the inner tubular member is attached from the inner portion of the lock, leaving the deployed lock in place, tensioning the cerclage implant.

Figure 14A:
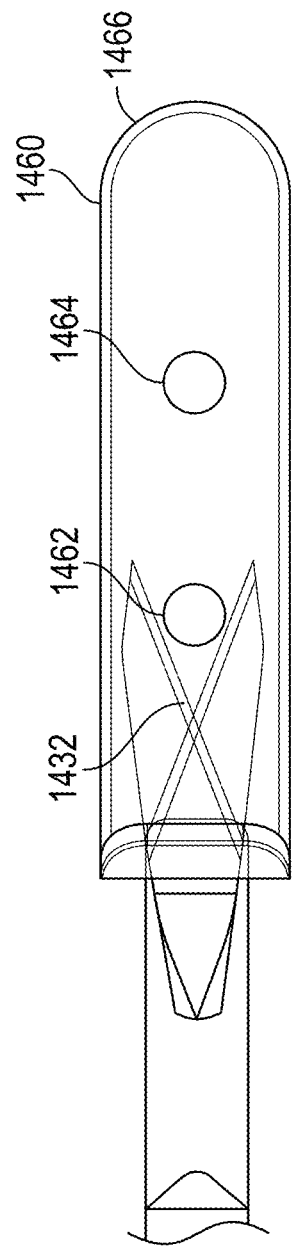
FIGS. 14A-14I illustrate aspects of a cutting instrument in accordance with the disclosure.

FIGS. 14A-14I illustrate portions of a cutting instrument 1400 in accordance with the disclosure for cutting the tethers/sheath material after the lock has been deployed. The cutting instrument 1400 includes an inner assembly with a blade that is slidably disposed within an outer assembly having a suture guide configured to hold suture/sheath material in position to facilitate cutting thereof while inside the heart, or other intracorporal location. FIG. 14A illustrates a distal portion of the inner assembly of the cutting instrument, which includes an elongate core shaft member (attached at a proximal end to a push hub) to a cutting blade holder at a distal end.

Figure 14B:
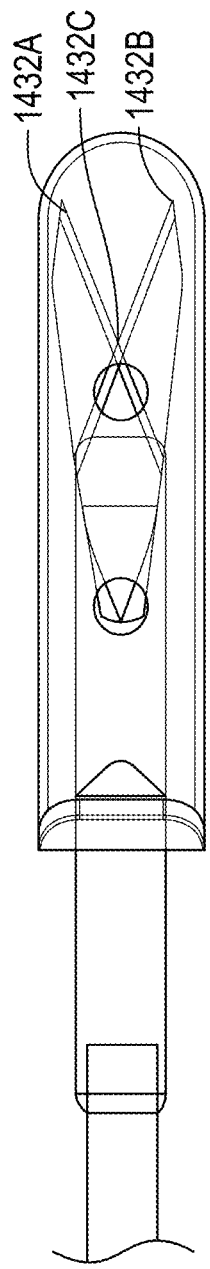
Figure 14C:
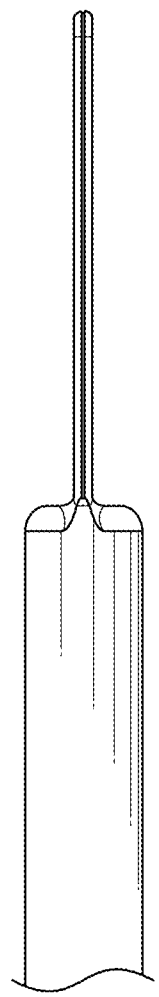
Figure 14D:
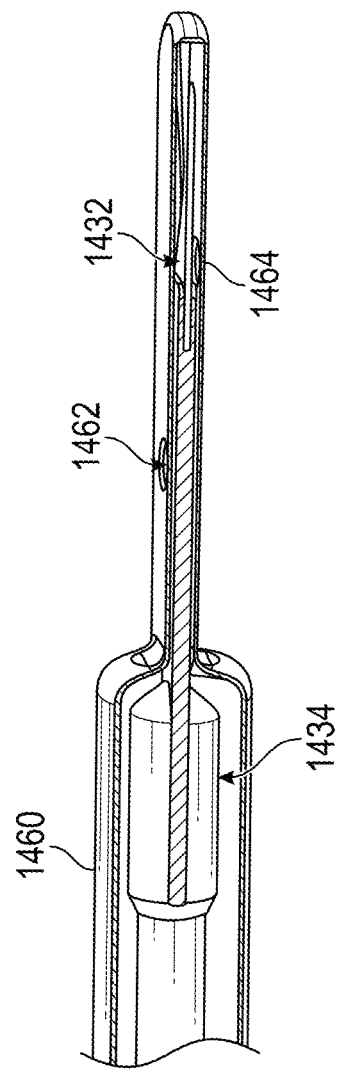
Figure 14E:
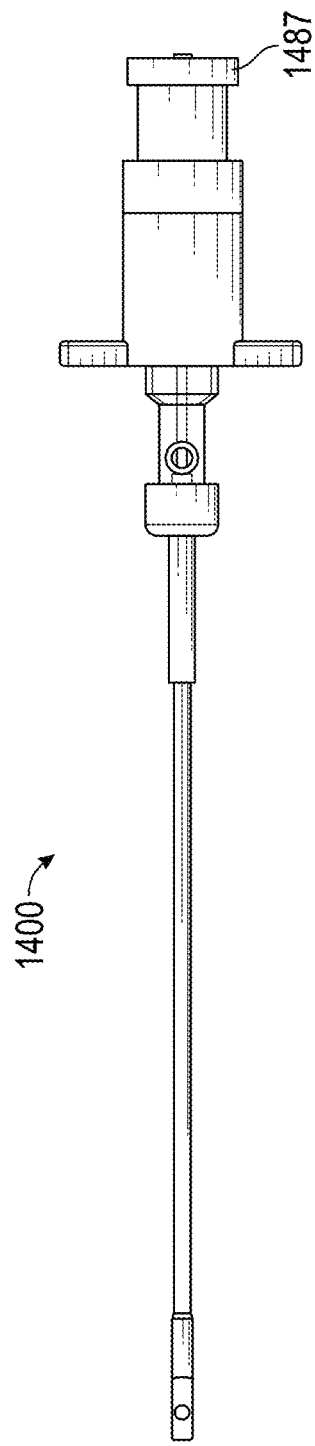
Figure 14F:

As illustrated in FIG. 14A, outer housing 1460 includes a rounded, atraumatic end 1466 and defines two axially spaced apart holes therethrough, wherein the distal hole 1464 accepts a sheath or suture (e.g., 450) therein as an entrance point or entrance hole, and the proximal hole 1462 provides an exit for the suture/sheath. In use, the cutting instrument 1400 is threaded over each tether of the implant in this manner through the holes 1462, 1464 after the lock delivery catheter is removed, and the sheath material (e.g., 450) is external to the patient or otherwise easily accessible. The cutting instrument is then delivered into the heart to a location near the lock that is already in place. The inner assembly of the cutting mechanism is then advanced distally with respect to the outer assembly of the cutting mechanism until the blade 1432 has advanced past both holes 1462, 1464, cutting the tether (e.g., 450) as illustrated in FIG. 14B. As illustrated in FIG. 14B, the blade 1432 is illustrated as having a first blade edge 1432A and a second blade edge 1432B forming a "V" shape and having an apex at 1432C. As illustrated in FIG. 14C, the flattened distal profile of the cutting instrument 1400 both reduces the profile of the instrument, as well as provide for superior alignment and smooth cutting operation. FIG. 14D provides a cutaway view of the distal end of the cutting instrument showing the relative placement of the inner and outer assemblies after the inner assembly has been fully extended distally to accomplish the cutting operation. FIG. 14D further illustrates that proximal hole 1462 is on a first side of the device, and distal hole 1464 is on a second, opposing side of the device.

Figure 14I:
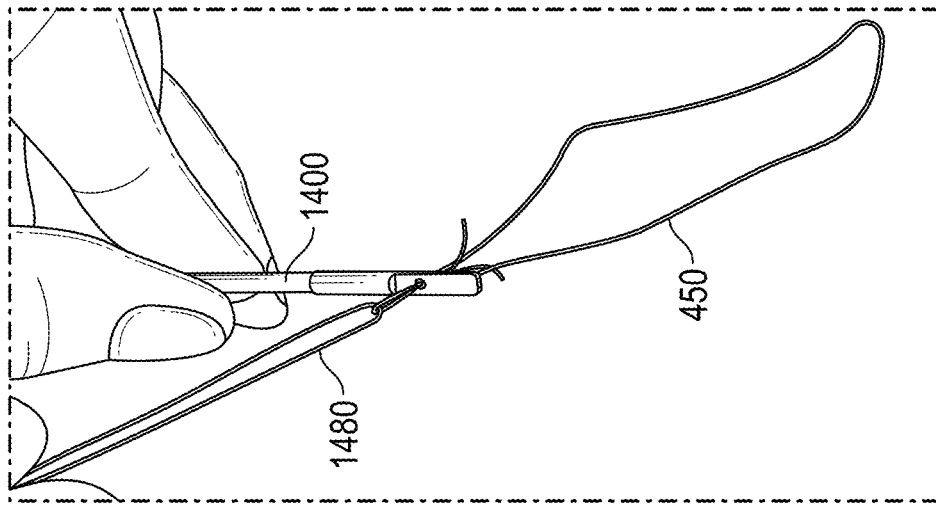
Figure 14H:
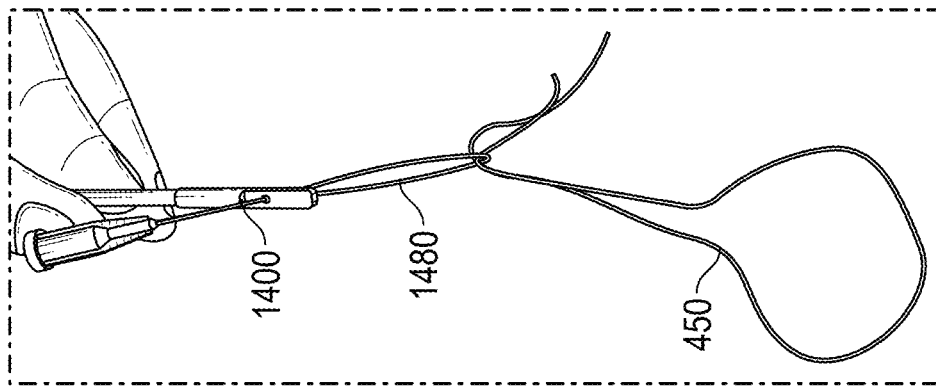
Figure 14G:
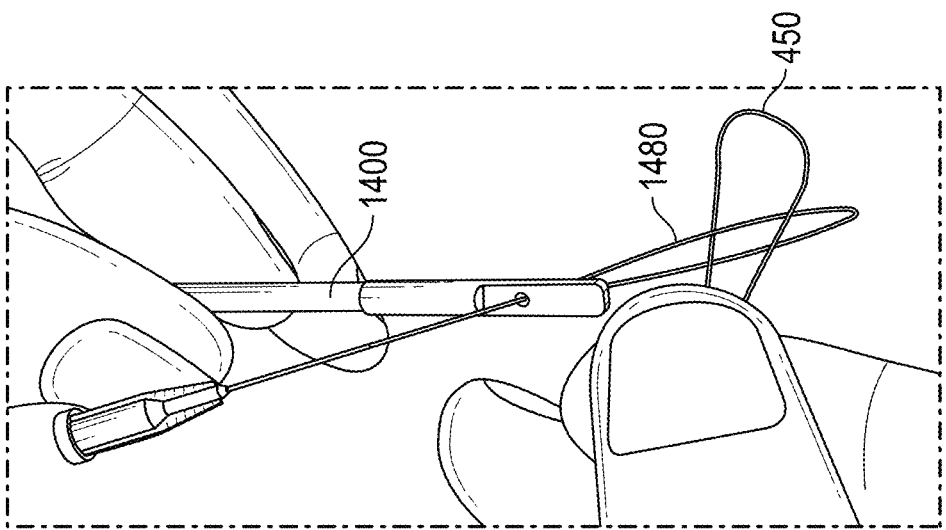

FIGS. 14E-14I illustrate use of the loading snare 1480. As illustrated in FIG. 22E, the catheter 1400 includes a distal end and internal mechanisms as set forth above, and including a proximal handle having a spring loaded push button trigger 1487, wherein the button is biased in a proximal direction by the spring (not shown). The button is connected to the inner movable shaft of the cutting catheter at the proximal end of the shaft, which is in turn connected at its distal end to the cutting blade. When the button is depressed by a user, the blade advances distally past openings 1462, 1464 to cut any tether spanning the openings through the cutting catheter 1400. The snare is utilized by initially passing the elongate loop portion of the snare diagonally through the distal portion of catheter 1400 by way of openings 1462, 1464. As illustrated in FIGS. 14G-14I, after the loop of snare 1480 is positioned through catheter 1400, ends of loop tether/sheath 450 are passed through the snare 1480, and the snare is withdrawn through catheter 1400, carrying tethers 450 therewith, effectuating threading of the cutting catheter with the loop tether/sheath 450.

It will be appreciated that other structures can be cut or severed using the cutting catheters of FIGS. 14A-14I. For example, in a further implementation, the cutting catheter as disclosed can be used to cut a cardiac lead previously attached to a pacemaker. Removal of cardiac leads is typically dangerous, but the presently disclosed embodiment can be threaded down the cardiac lead, for example, into the left ventricle or other cardiac location. The lead can then be severed near or at the anchoring point, leaving the anchor in place, but removing the wire.

Figure 15C:
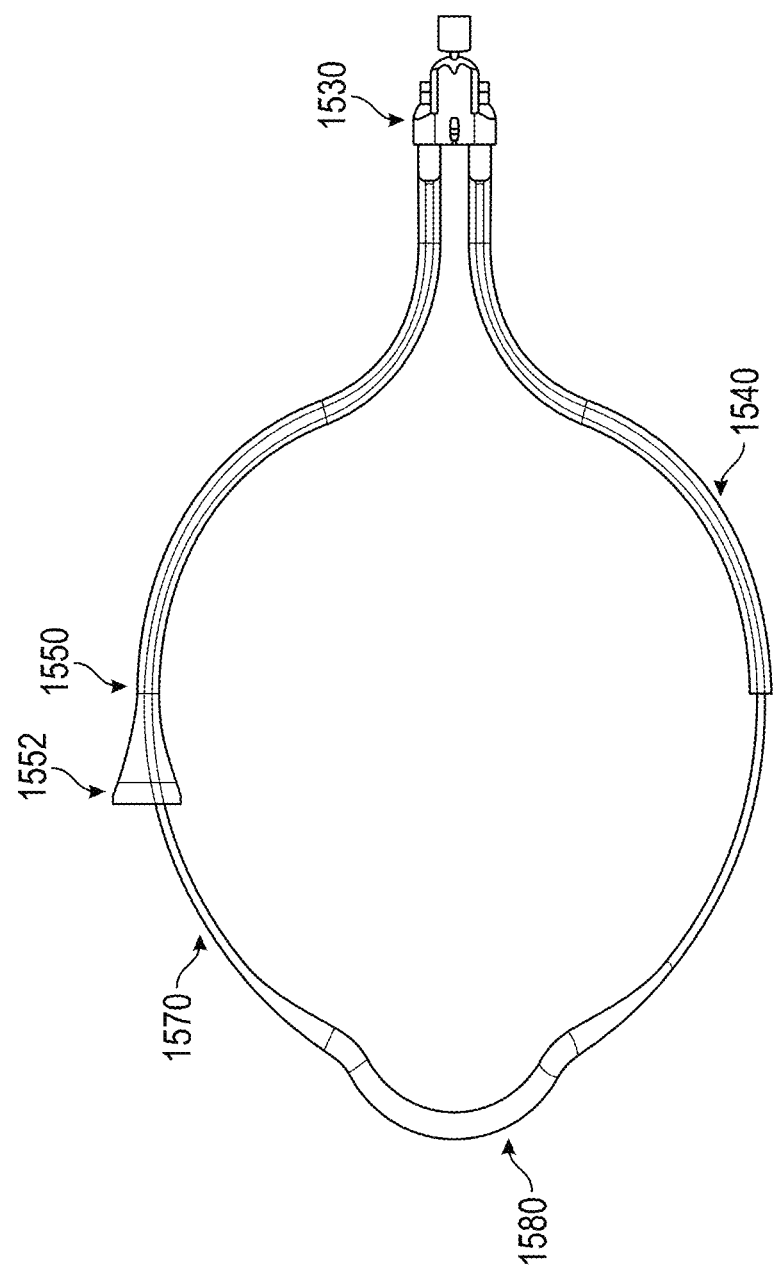
Figure 15E:
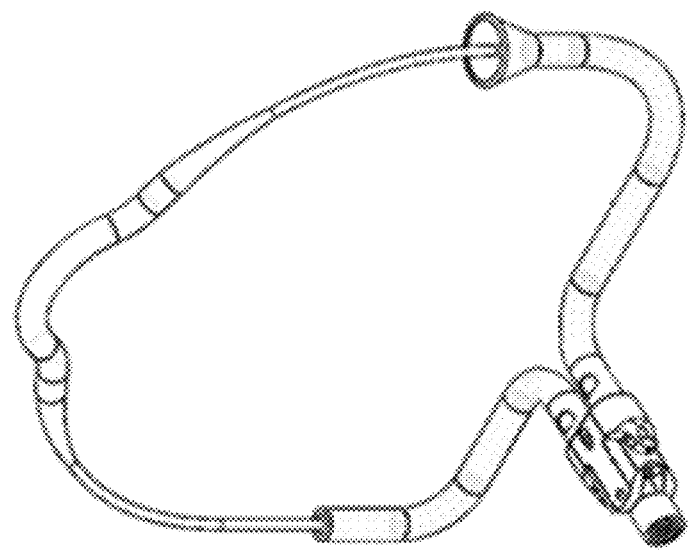
Figure 15D:
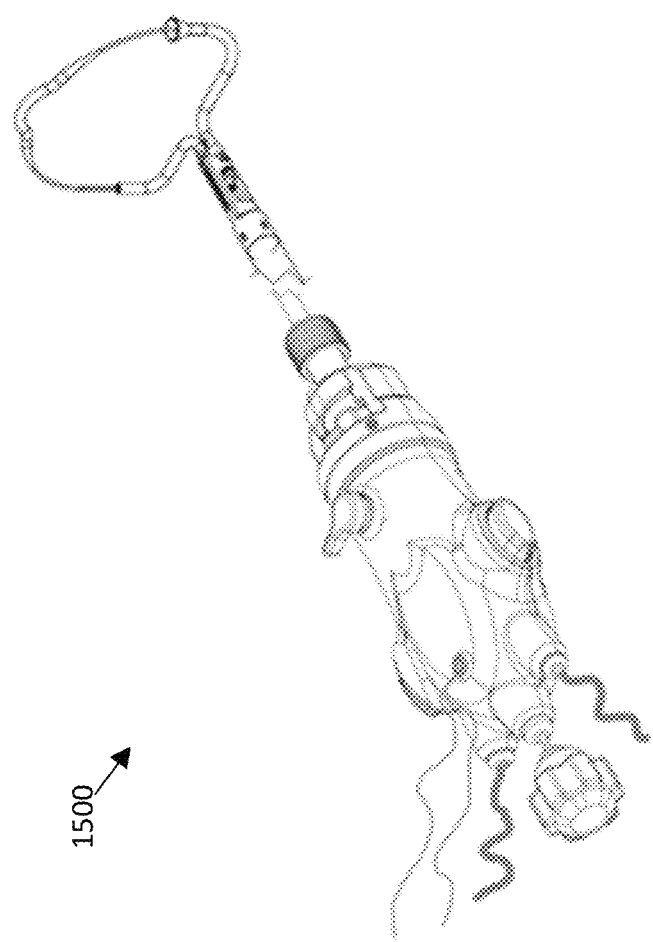

FIGS. 15A-15E illustrate a further embodiment of a lock delivery catheter 1500 including a handle 1502 similar to previous embodiments. Catheter 1500 includes a handle 1502 that has the same functionality as previous embodiments with a tensioning tether control as described above with reference to FIGS. 11A-11B. Catheter 1500 includes a lock release knob for advancing the lock mechanism proximally or distally with respect to the handle 1502, as well as for releasably engaging the lock body (e.g., via threaded connection) as set forth above. Catheter 1500 further includes a removable sheath 1510 that surrounds the lock body 1530, the coronary sinus limb 1540, the tricuspid valve limb 1550 that may include a bumper 1552 (for spreading out axial force applied to the septal wall), and may provide a conduit for guiding placement of the tether loading snares. The catheter including the sheath 1510 can be introduced into the patient's vasculature over the outer sheath (e.g., 450) of the implant after the delivery tubes (or core wires, depending on the embodiment) are removed. The sheath can be withdrawn proximally, for example, via a pull wire (not shown) routed through handle 1502 or peeled off, ruptured, or the like at a suitable time, such as when the distal end of the sheath is near the patient's heart. The limbs are then exposed, which can be directed into the vasculature of the heart, and placed where desired. The sheath (e.g., 450) can then be locked inside of the lock body 1530, and the excess sheath extending proximally from the lock body 1530 can be severed using embodiments of the cutting catheter disclosed herein. FIG. 15C shows a schematic view of the installed implant and lock body with limbs, which may include the coronary protection element 1580 (if desired) surrounded by the sheath 1570, which may be radiopaque as discussed above. Also illustrated are the tricuspid valve limb 1550 with the bumper 1552, as well as the coronary sinus limb 1540. FIG. 15D presents an isometric view of the lock delivery system 1500 prior to deployment (release) of the lock body, whereas FIG. 15E illustrates a perspective view of the lock and implant after deployment. As illustrated, the limbs are presented as not being planar, but instead having a three dimensional curvature wherein the limbs curve out of plane toward the lock. As will be appreciated, the proximal ends of the limbs are preferably attached to the lock body.

Figure 16B:
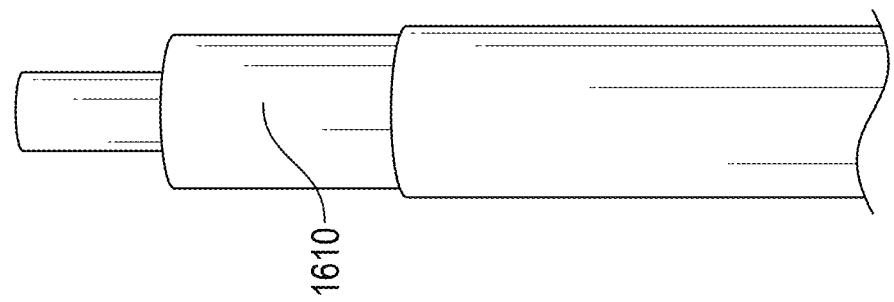
FIGS. 16A-16D illustrate a particular embodiment of a lock in accordance with the present disclosure.
Figure 16A:
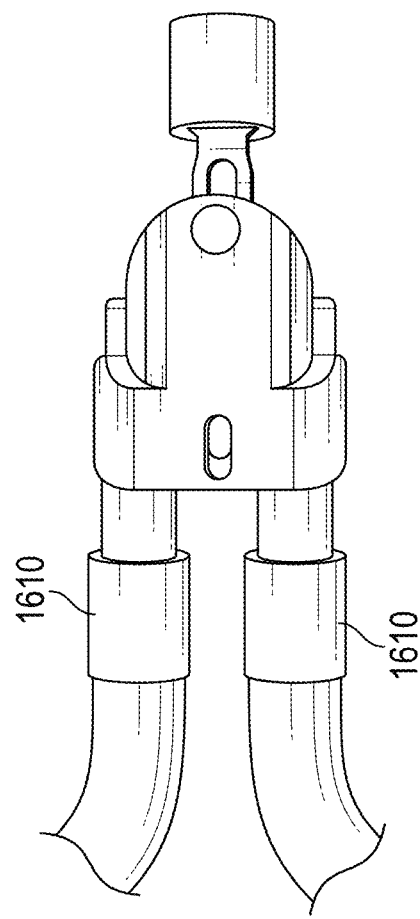
Figure 16D:
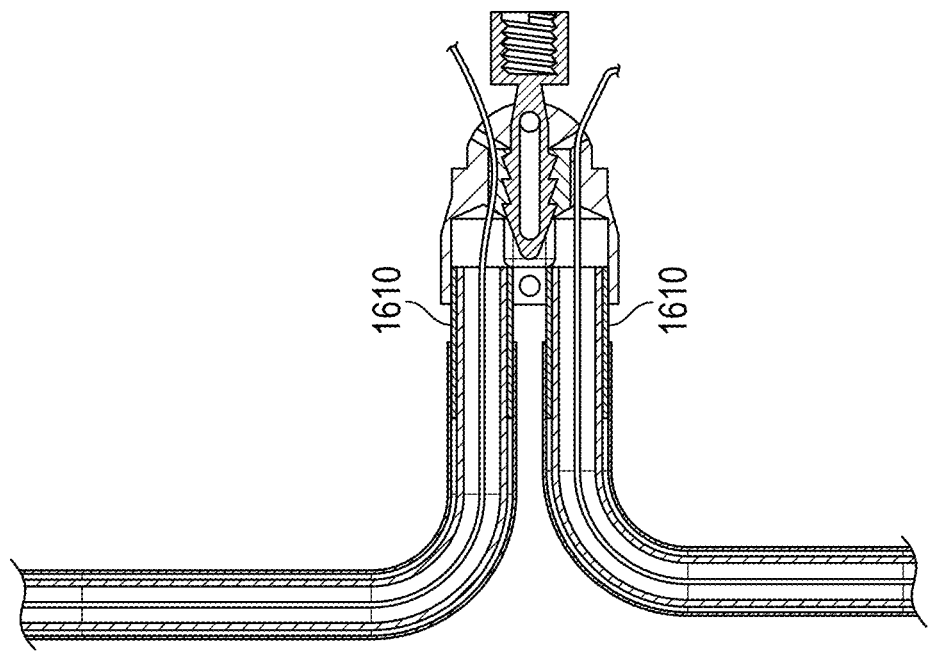
Figure 16C:
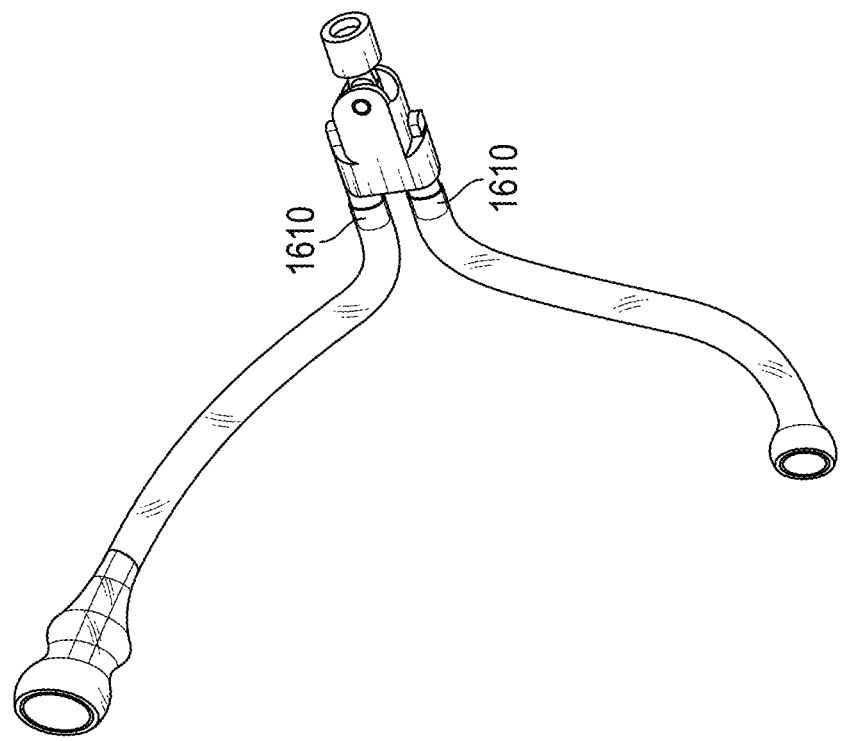

FIGS. 16A-16D illustrate a further embodiment of a lock body and protruding limbs to be routed over the implant 400 during the implantation procedure as described elsewhere herein. In particular, FIGS. 16A-16D detail the precise construction used to build this embodiment. The limbs have a proximal end that attach to the lock body, and a distal end. As set forth in FIGS. 16A-16D, the proximal ends of the limbs are constructed by providing inner and outer concentric polymeric tubes, wherein a distal end of a metallic (e.g., titanium) tube is inserted between the tubes at the proximal end of the tubes. One or more windows 1610, or holes, are defined in the portion of the metallic tube that is inserted between the tubes. The assembly is then heated and formed in order to cause the polymeric material of the tubes to flow through the window(s) defined in the metallic tube, causing the inner and outer tubes to fuse to each other through the window(s) in the sidewall of the metallic tubular member. The opposing proximal end of the tubular member is then welded (e.g., laser welded) to the lock body (FIG. 16B). This procedure is used to form the proximal ends of both limbs and to attach them to the lock body. The metallic tubes and lock body can be any suitable material (e.g., titanium, stainless steel, nickel-titanium alloys, and the like) formed, for example, into a hypotube. Preferably, the lock body and tubes are made from the same or similar materials to permit bonding by welding. As illustrated in FIG. 16C, the polymeric limbs can be heat set to a shape that approximates the expected position of the device in the patient's anatomy. The polymeric limbs can be formed from polyether block amide or other suitable material. FIG. 16D provides an illustrative cross section of the lock and limbs with the tether of the implant directed therethrough.

Figure 17:
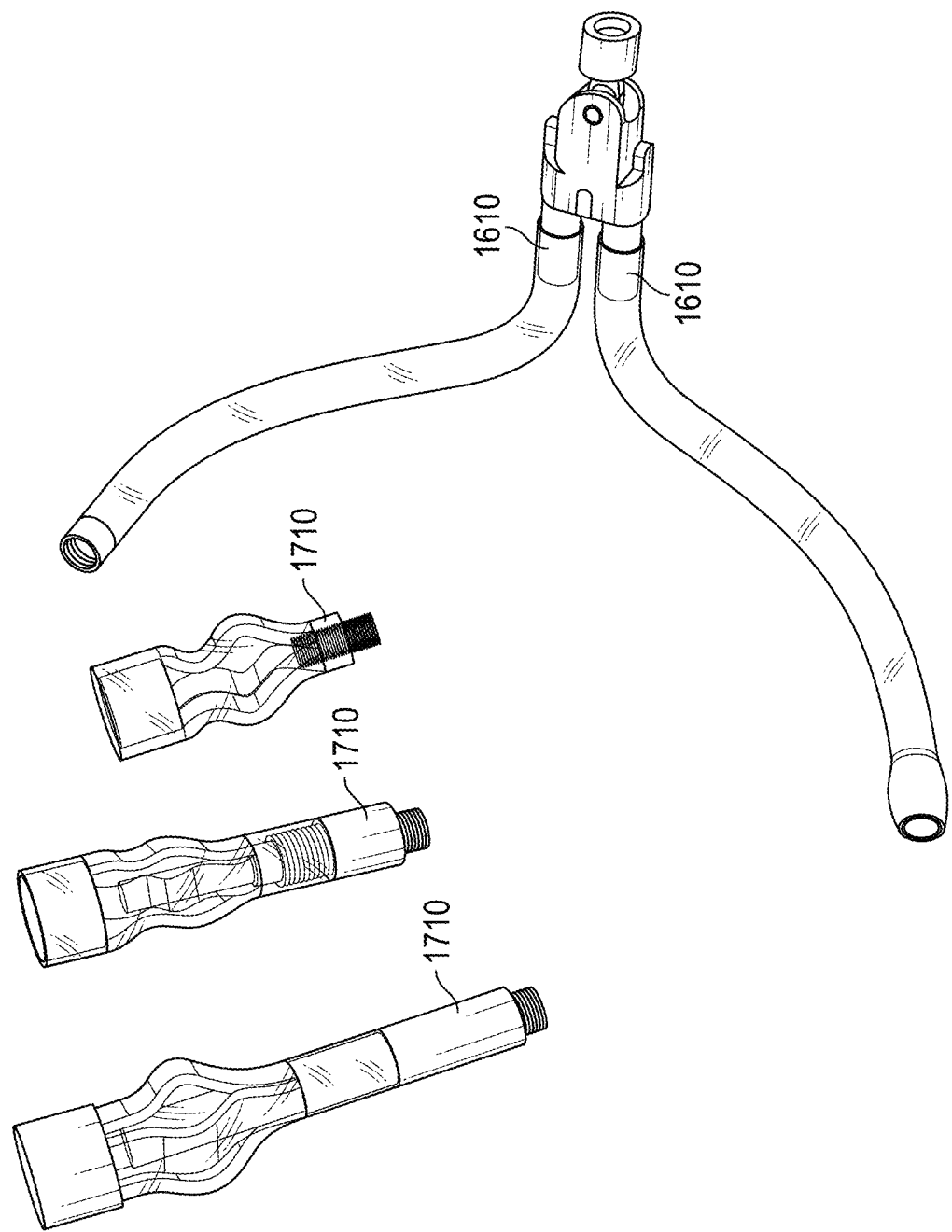
FIG. 17 illustrates a further embodiment of a lock in accordance with the present disclosure having at least one limbs with interchangeable ends of different lengths, wherein the ends are also of adjustable length.

FIG. 17 presents a further embodiment of the lock and limb assembly, wherein the RVOT limb is illustrated as having interchangeable limbs 1710 of different lengths to accommodate different sized vasculatures. Thus, a kit can be provided having limbs of varying lengths, and the pertinent medical professional can make an evaluation of which size limb extension to use. Limbs 1710 can be removably attached to the remainder of the structure, for example, by a threaded connection. It will be appreciated that the limb extensions can themselves be provided with features as set forth elsewhere herein to provide adjustable length.

Figure 18:
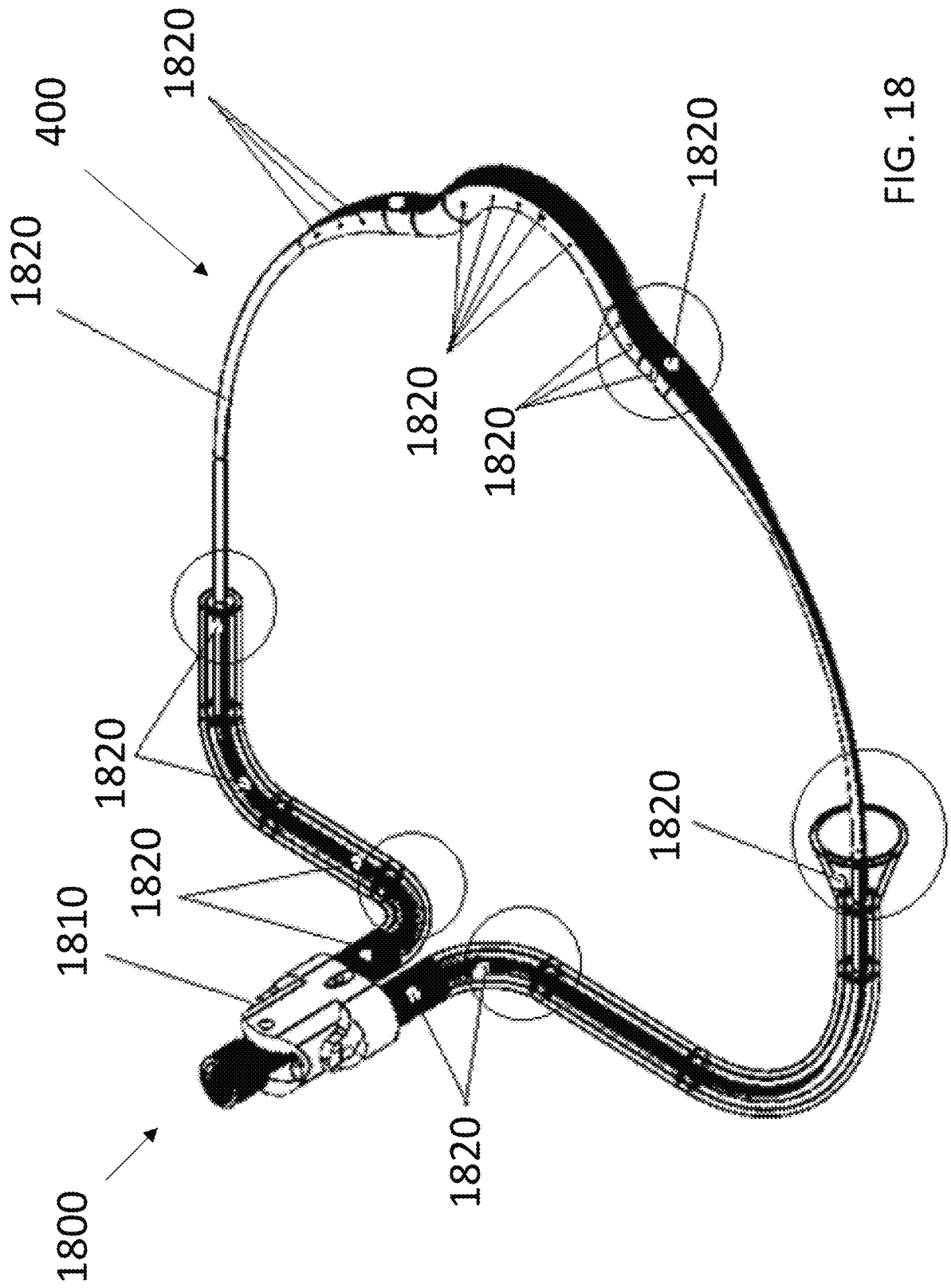
FIG. 18 illustrates an embodiment of a system for delivering cardiac pacing and/or a beneficial agent in accordance with the present disclosure.

In accordance with further aspects, FIG. 18 illustrates an implementation 1800 of an implantable pacing system configured and arranged to circumnavigate a loop path in a heart. For example, U.S. Ser. No. 15/328,046 sets forth one technique for implanting a pacemaker lead via the septal vein using an approach through the coronary sinus, in a manner similar to making a path to implant devices in accordance with the present disclosure. Thus, an initial lead (preferably a bipolar lead) is anchored in the septal wall in a location where signals originating therefrom can provide a minimum QRS. Once suitably anchored, if desired, a proximal end of the lead, or an extension thereof, can be externalized from the patient, and a specially configured implant similar in structure to implant 400 can be delivered over the cardiac lead, using the cardiac lead as a delivery rail at least in part. Alternatively, the lead can be externalized, and the implant can be delivered after being crimped to a proximal end of an externalized guidewire as disclosed herein, and the implant can be installed. When it comes time to install the lock, the lock can be threaded over the implant (e.g., 400) as well as the cardiac lead, and when the lock is locked in place, the lock can be configured to complete an electrical contact with the lead. For example, the lock can include a controller having a power supply and a signal generator. The inner elongate tether can also be caused to complete an electrical circuit with the lock, and appropriate control circuitry can be provided in the lock for the loop of platinum or other wire in the inner tether to function as an antenna for sending or receiving signals, or for receiving a charging pulse to charge a battery in the lock for powering the pacemaker.

However, embodiment 1800 can also be configured to contain all of its sensors and electrodes (referred to in combination as 1820) on board. Thus, the implant 1800 can be delivered and assembled in place, and can be programmed to stimulate cardiac tissue and/or sense biological conditions (e.g., electrical mechanical and chemical conditions) within the heart.

Thus, the pacing system 1800 can include an elongate inner tether as set forth herein having a proximal end and a distal end, an outer sheath material surrounding the elongate inner tether having a proximal end and a distal end, at least one electrical conductor disposed along or within at least one of the elongate inner tether and the outer sheath, a cardiac pacing controller 1810, which may be integrated into the lock of the implant, may include a power source, a pulse generator, and control circuitry operably coupled to the at least one electrical conductor, at least one cardiac pacing electrode configured and arranged to be implanted in or on top of cardiac tissue, the at least one cardiac pacing electrode being electrically coupled to the cardiac pacing controller by way of the at least one electrical conductor, and a lock securing the proximal end and distal end of the outer sheath material.

In some implementations, the lock can be coupled to the cardiac pacing controller. The at least one electrical conductor is disposed at least partially within the elongate inner tether. If desired, the lock/controller 1810 can include one or more cardiac pacing leads routed therethrough terminating at electrodes indicated a locations 1820, or any other desired location. Electrical communication can be established with the cardiac pacing lead by engaging a portion of the lock. Or, the lock/controller 1810 can be pre-connected to cardiac leads and electrodes integrally formed into the curved tubular limbs of the implant that connect to the lock/controller 1810. If desired, the portion 400 of the implant received by the lock limbs can also be provided with sensors 820. If desired, electrical power can be directly transferred to implant 400 via a core platinum wire described elsewhere herein. Components integrated into the portion 400, such as sensors and electrodes, can then draw power off of the core wire (e.g., 410a') in order to operate. Electrical connections between the power supply/lock 1810 and pacing electrodes 1820 or other sensors can be direct conductive pathways wherein conductors are placed between inner and outer tubular polymeric layers of the limbs attached to the lock/controller 1820, or nested within the layers of the implant 400. If desired, the sensors or electrodes can be formed over the surface of the implant lock/limbs and portion 400, and then be overlaid with an additional layer of heat shrunk polymeric tubing. If desired, that outer layer of tubing can include windows formed therein for exposing the sensors or electrodes 1820.

In some implementations, the pacing system 1800 can further include at least one lumen along a length of the outer sheath for receiving a pacing lead, wherein the pacing system can be slid along the pacing lead into the coronary sinus. The at least one lumen can be configured to direct the pacing lead toward the cardiac pacing controller. In some embodiments, the system can include a protective bridge for spanning the LCx artery when in the coronary sinus near the septal wall as described elsewhere herein. In some embodiments, at least a portion of the cardiac pacing controller can be disposed within the outer sheath.

The pacing system can further include an electrical battery disposed within components 1810 and/or 400 that is at least partially disposed within the outer sheath. The pacing system can further include a circuit board that is at least partially disposed within the outer sheath. The pacing system can further include communications circuitry that is at least partially disposed within the outer sheath. The communications circuitry can be hard wired, and/or wireless (e.g., via Bluetooth communication).

If desired, the pacing system 1800 can further include at least one sensor circuit that is at least partially disposed within the outer sheath, the at least one sensor module 1820 including at least one sensor (e.g., sensing circuitry) for sensing at least one biological parameter. For example, the at least one sensor circuit/module can include at least one pressure sensor for detecting blood pressure, or at least one of a chemical sensor, a distance sensor, a sensor having circuitry to detect electro physiological data, a movement sensor, and a location sensor.

In some implementations, the at least one electrical conductor can terminate at the lock/controller 1810. If desired, the system can further include at least one pacing lead (and/or electrical sensor for sensing cardiac electrical signals) formed into a surface of the outer sheath. The at least one pacing lead can be configured and arranged to interface with the Right Atrium. If desired, a further pacing lead can be configured and arranged to interface with the Right Ventricle, or a cardiac vein such as the septal vein, and be located, for example, in the regions denoted by circles in FIG. 18. If desired, the controller 1810 can be configured and arranged to provide at least one of pacing, defibrillation, measurement and control.

In some implementations of the pacing system the inner elongate tether can include a loop antenna that conducts signals to and from the controller. In further implementations, the pacing system (or other system) can further include a reservoir for containing a beneficial agent coupled to a dispenser controlled by the controller. For example, the beneficial agent can include a medication, a gene therapy material, and/or living cells for seeding at least one location of the heart that is damaged.

The heart's intrinsic electrical activity (i.e. the P wave or QRS complex) transmits a small electrical current (a few millivolts), through the pacemaker leads, to the pulse generator. This current can be registered or sensed by the pacemaker circuitry. The pacemaker sensing can be used to formulate a response of a pacemaker to intrinsic heartbeats. The P waves, or atrial activity, are transmitted through an atrial lead (if present) to an atrial channel of the pacemaker, and sensed as atrial activity. Ventricular activity (the QRS complex) can be transmitted through the ventricular lead (if present, such as via the septal vein) to the ventricular channel of the pacemaker, and this is sensed as ventricular activity.

For electrical activity to be transmitted from the heart to the pacemaker, a closed electrical circuit must be present, just the same as for an electrical impulse to be transmitted from the pacemaker to the heart. Thus, just as with pacing, sensing can be unipolar or bipolar. Bipolar sensing detects the intrinsic electrical activity occurring between the tip electrode and the ring electrode of the lead. Unipolar sensing detects electrical activity occurring between the tip of the lead, and the metal shell of the pulse generator. Because this is a much larger area, other electrical signals, such as might be generated by the muscles of the diaphragm or sources outside the body, are more likely to be detected (and therefore incorrectly interpreted by the pacemaker as heart beats). It is important to note that the only way the pacemaker can determine which chamber a signal originates from is by which lead transmits the signal to the pacemaker. For example, the pacemaker could interpret any electrical signal transmitted through the atrial lead to the atrial channel as a P wave, even if the signal is in fact a QRS complex large enough in amplitude to be sensed by the atrial channel. Note also that the time at which the pacemaker senses the atrial or ventricular signal is not necessarily the beginning of the P wave or QRS. The pacemaker cannot sense activity in a chamber until the electrical activity actually reaches the pacemaker lead.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

The invention claimed is:

1. A cutting catheter, comprising:
a) an elongate inner member having a proximal end and a distal end with a distally facing blade mounted on the distal end; and
b) an elongate outer tubular member having a proximal end, a distal end and defining an elongate lumen therethrough for slidably receiving the elongate inner tubular member therein, wherein the elongate outer tubular member defines a pair of laterally offset holes therethrough near the blade for receiving a suture material therethrough, wherein distal advancement of the elongate inner member with respect to the elongate outer tubular member passes the blade past the suture to cut the suture, wherein the distally facing blade is configured to slide within a flattened distal portion of the elongate outer tubular member.

2. The cutting catheter of claim 1, wherein the distal end of the elongate outer tubular member is rounded and atraumatic.

3. The cutting catheter of claim 1, wherein the pair of holes includes two axially spaced apart holes defined through a distal end region of the cutting catheter, wherein a distal hole of the pair of holes accepts a suture therethrough as an entrance port, and a proximal hole of the pair of holes provides an exit port for the suture.

4. The cutting catheter of claim 1, further comprising a proximal handle having a spring loaded push button trigger, wherein the push button trigger is coupled to the elongate inner member.

5. The cutting catheter of claim 4, wherein the distally facing blade advances distally past the openings when the trigger is depressed.

6. The cutting catheter of claim 1, wherein the distally facing blade is "V" shaped, and the distally facing blade is configured to capture a suture in an apex of the distally facing blade, wherein the suture passes through the pair of holes.

7. A cutting catheter, comprising:
a) an elongate inner member having a proximal end and a distal end with a distally facing blade mounted on the distal end;
b) an elongate outer tubular member having a proximal end, a distal end and defining an elongate lumen therethrough for slidably receiving the elongate inner tubular member therein, wherein the elongate outer tubular member defines first and second holes on first and second opposing sides of a distal end region of the elongate outer tubular member, wherein a suture passing through the distal end region of the cutting catheter can be used as a guide rail to slide the distal end region of the cutting catheter percutaneously through a patient's vasculature to an target location near the patient's heart; and
c) a proximal handle including an actuator having a push-button trigger that is movably disposed with respect to the proximal handle, the actuator being coupled to the elongate inner member, wherein actuating the actuator causes the distally facing blade to move distally past at least one of the first hole and the second hole.

8. The cutting catheter of claim 7, wherein the distally facing blade is "V" shaped, and to cause the distally facing blade to capture a suture in an apex of the distally facing blade, wherein the suture passes through the first and second openings.

9. A method of using the cutting catheter of claim 7, including, threading an elongate member to be severed that extends outside of a patient through the first and second holes of the cutting catheter, introducing the distal end region of the cutting catheter over the elongate member into the vasculature of the patient, advancing the catheter to a target location within the patient's vasculature, and advancing the blade distally with respect to the outer tubular member to sever the elongate member.

10. A method of using the cutting catheter of claim 7, including threading a proximal end of a cardiac lead coupled to an anchoring point inside a patient's vasculature through the first and second holes of the cutting catheter, introducing the distal end region of the cutting catheter over the cardiac lead into the vasculature of the patient, advancing the catheter to a target location within the patient's vasculature near the anchoring point, and advancing the blade distally with respect to the outer tubular member to sever the cardiac lead.

11. The cutting catheter of claim 7, wherein the distal end of the elongate outer tubular member is rounded and atraumatic.

12. The cutting catheter of claim 7, wherein the first and second holes includes two axially spaced apart holes defined through a distal end region of the cutting catheter, wherein a distal hole of first and second holes accepts a suture therethrough as an entrance port, and a proximal hole of the first and second holes provides an exit port for the suture.

13. The cutting catheter of claim 7, wherein the distally facing blade advances distally past the first and second holes when the actuator is actuated.

14. A cutting catheter, comprising:
an elongate inner member having a proximal end and a distal end with a distally facing blade mounted on the distal end; and
an elongate outer tubular member having a proximal end, a distal end and defining an elongate lumen therethrough for slidably receiving the elongate inner tubular member therein, wherein the elongate outer tubular member defines first and second holes on first and second opposing sides of a distal end region of the elongate outer tubular member; and
a loading snare directed through the first and second holes to receive an elongate member to be pulled through the first and second holes to load the cutting catheter, tubular member is rounded and atraumatic.

15. The cutting catheter of claim 14, wherein the distal end of the elongate outer tubular member is rounded and atraumatic.

16. The cutting catheter of claim 14, wherein the first and second holes include two axially spaced apart holes defined through a distal end region of the cutting catheter, wherein a distal hole of the first and second holes accepts a suture therethrough as an entrance port, and a proximal hole of the first and second holes provides an exit port for the suture.

17. The cutting catheter of claim 14, wherein the distally facing blade is "V" shaped, and the distally facing blade is configured to capture a suture in an apex of the distally facing blade, wherein the suture passes through the pair of holes.

\* \* \* \* \*